US006995018B1

(12) United States Patent
Fisher et al.

(10) Patent No.: US 6,995,018 B1
(45) Date of Patent: Feb. 7, 2006

(54) COMPLEX FORMED BY N-LINKED GLYCOPROTEINS (SIBLINGS)AND FACTOR H

(75) Inventors: Larry W. Fisher, Derwood, MD (US); Neal S. Fedarko, Columbia, MD (US); Marian F. Young, Silver Springs, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/958,617

(22) PCT Filed: Apr. 7, 2000

(86) PCT No.: PCT/US00/09349

§ 371 (c)(1), (2), (4) Date: Jan. 18, 2002

(87) PCT Pub. No.: WO00/62065

PCT Pub. Date: Oct. 19, 2000

Related U.S. Application Data

(60) Provisional application No. 60/128,468, filed on Apr. 9, 1999.

(51) Int. Cl.
*G01N 33/536* (2006.01)
*G01N 33/574* (2006.01)
*G01N 33/68* (2006.01)

(52) U.S. Cl. .................... 435/701; 435/7.21; 435/7.23; 435/961; 435/962; 436/501; 436/518; 436/536; 436/821; 436/825; 436/64; 436/87; 436/161; 436/175; 436/177

(58) Field of Classification Search ................. 435/7.1, 435/7.21, 7.23, 961–962; 436/501, 518, 436/536, 821, 825, 64, 87, 161, 175, 177
See application file for complete search history.

(56) References Cited

U.S. PATENT DOCUMENTS

| | | | | |
|---|---|---|---|---|
| 5,049,659 | A | 9/1991 | Cantor et al. | 530/351 |
| 5,180,808 | A | 1/1993 | Ruoslahti | 530/350 |
| 5,306,305 | A | 4/1994 | Lee | 623/16 |
| 5,340,934 | A | 8/1994 | Termine et al. | |
| 5,453,492 | A | 9/1995 | Butzow et al. | 530/413 |
| 5,545,534 | A | 8/1996 | Akita et al. | 435/7.92 |
| 5,693,511 | A | 12/1997 | Harris et al. | 435/172.3 |
| 6,753,314 | B1 * | 6/2004 | Giot et al. | 514/12 |

FOREIGN PATENT DOCUMENTS

| | | |
|---|---|---|
| JP | 09138213 | 5/1997 |
| WO | WO94/13310 | 6/1994 |
| WO | WO 99/50666 | 10/1999 |

OTHER PUBLICATIONS

Bellahcéne et al., "Bone sialoprotein expression in primary human breast cancer is associated with bone metastases development," *Journal of Bone and Mineral Research* 11:665-670, 1996a.

Bellahcéne et al., "Detection of bone sialoprotein in human breast cancer tissue and cell lines at both protein and messenger ribonucleic acid levels," *Laboratory Investigation* 75:203-210, 1996b.

Bellahcéne et al., "Ectopic expression of bone sialoprotein in human thyroid cancer," *Thyroid* 8:637-641, 1998.

Bellahcéne et al., "Expression of bone matrix proteins in human breast cancer: Potential roles in microcalcification formation and in the genesis of bone metastases," *Bulletin du Cancer* 84(1):17-24, 1997a.

Bellahcéne et al., "Expression of bone sialoprotein, a bone matrix protein, in human breast cancer," *Cancer Research* 54:2823-2826, 1994.

Bellahcéne et al., "Expression of bone sialoprotein in human lung cancer," *Calcified Tissue International* 61:183-188, 1997b.

Bellahcéne et al., "Expression of bone sialoprotein in primary human breast cancer is associated with poor survival," *International Journal of Cancer* (*Pred. Oncol.*) 69:350-353, 1996c.

Bianco et al, "Expression of bone sialoprotein (BSP) in developing human tissues," *Calcified Tissue International* 49:421-426, 1991.

Bresalier et al., "Cell surface sialoprotein alterations in metastatic murine colon cancer cell lines selected in an animal model for colon cancer metastasis," *Cancer Research* 50:1299-1307, 1990.

Ecarot-Charrier et al., "Bone sialoprotein II synthesized by cultured osteoblasts contains tyrosine sulfate," *The Journal of Biological Chemistry* 264:20049-20053, 1989.

Fisher et al., "Matrix sialoprotein of developing bone," *The Journal of Biological Chemistry* 258:12723-12727, 1983.

Fisher et al., "Noncollagenous proteins influencing the local mechanisms of calcification," *Clinical Orthopaedics and Related Research* 200:362-385, 1985.

(Continued)

*Primary Examiner*—David Saunders
(74) *Attorney, Agent, or Firm*—Klarquist Sparkman, LLP

(57) ABSTRACT

The invention provides methods and compositions for exploiting the discovery that members of the small integrin-binding ligand, n-linked glycoproteins family termed SIBLINGS bind to complement Factor H, and moreover that SIBLINGS proteins, such as BSP, exist in relatively acidic forms. The methods provided can be used to detect SIBLINGS proteins in samples from subjects that are suspected of having tumors or abnormal bone turnover. The invention also provides methods of using SIBLINGS proteins to protect cells from complement mediated lysis. Finally, the discovery allows for the creation of specific binding agents that facilitate the detection of SIBLINGS proteins when they are associated with Factor H.

31 Claims, 11 Drawing Sheets

OTHER PUBLICATIONS

Fisher et al, "Purification and partial characterization of small proteoglycans I and II, bone sialoproteins I and II, and osteonectin from the mineral compartment of developing human bone," *The Journal of Biological Chemistry* 262: 9702-9708, 1987.

Gillespie et al., "Calcitonin receptors, bone sialoprotein and osteopontin are expressed in primary breast cancers," *International Journal of Cancer* 73:812-815, 1997.

Karmatschek et al., "Improved purification of human bone sialoprotein and development of a homologous radioimmunoassay," *Clin Chem* 43(11):2076-2082, Nov. 1997.

Midura et al., "A rat osteogenic cell line (UMR 106-01) synthesizes a highly sulfated form of bone sialoprotein," *The Journal of Biological Chemistry* 265:5285-5291, 1990.

Mintz et al., "Chlorate-induced inhibition of tyrosine sulfation on bone sialoprotein synthesized by a rat osteoblast-like cell line (UMR 106-01 BSP)," *The Journal of Biological Chemistry* 269:4845-4852, 1994.

Oldberg et al., "The primary structure of a cell-binding bone sialoprotein," *The Journal of Biological Chemistry* 263: 19430-19432, 1998.

Seibel et al., "Serum immunoreactive bone sialoprotein as a new marker of bone turnover in metabolic and malignant bone disease," *Journal of Clinical Endocrinology and Metabolism* 81:3289-3294, 1996.

Senger et al., "Purification of a human milk protein closely similar to tumor-secreted phosphoproteins and osteopontin," *Biochimica et Biophysica Acta* 996:43-48, 1989.

Stubbs et al., "Characterization of native and recombinant bone sialoprotein: delineation of the mineral-binding and cell adhesion domains and structural analysis of the RGD domain," *Journal of Bone and Mineral Research* 12:1210-1222, 1997.

van der Pluijm et al., "Bone sialoprotein peptides are potent inhibitors of breast cancer cell adhesion to bone," *Cancer Research* 56:1948-1955, 1996.

Waltregny et al., "Prognostic value of bone sialoprotein expression in clinically localized human prostate cancer," *J Natl Cancer Inst* 90(13):1000-1008, Jul. 1998.

Withold et al., "Bone sialoprotein in serum of patients with malignant bone diseases," *Clinical Chemistry* 43:85-91, 1997.

Fedarko et al., "Factor H binding to bone sialoprotein and osteopontin enables tumor cells evasion of complement-mediated attach," *J. Biol. Chem.,* vol. 275, No. 22, pp. 16666-16672 (2000).

Fedarko et al., "Integrins and factor H mediate bone sialoprotein's and osteopontin's protective properties in complement attach on susceptible cancer cells," *Journal of Bone and Mineral Research,* Twenty First Annual Meeting of the American Society for Bone and Mineral Research, St. Louis, Missouri (Sep. 30-Oct. 4, 1999), vol. 14, No. Suppl. 1, pp. S187 (1999).

Fisher et al., "Antisera and cDNA probes to human and certain animal model bone matrix noncollagenous proteins," *Acta Orthopaedica Scaninavica,* vol. 266, pp. 61-65 (1995).

Pritchard et al., "Is the expression of osteopontin and bone sialoprotein greater in breast cancer bone metastases compared to other metastatic sites," *European Symposium on Calcified Tissues,* vol. 20, No. 4S, p. 63S (1997).

* cited by examiner

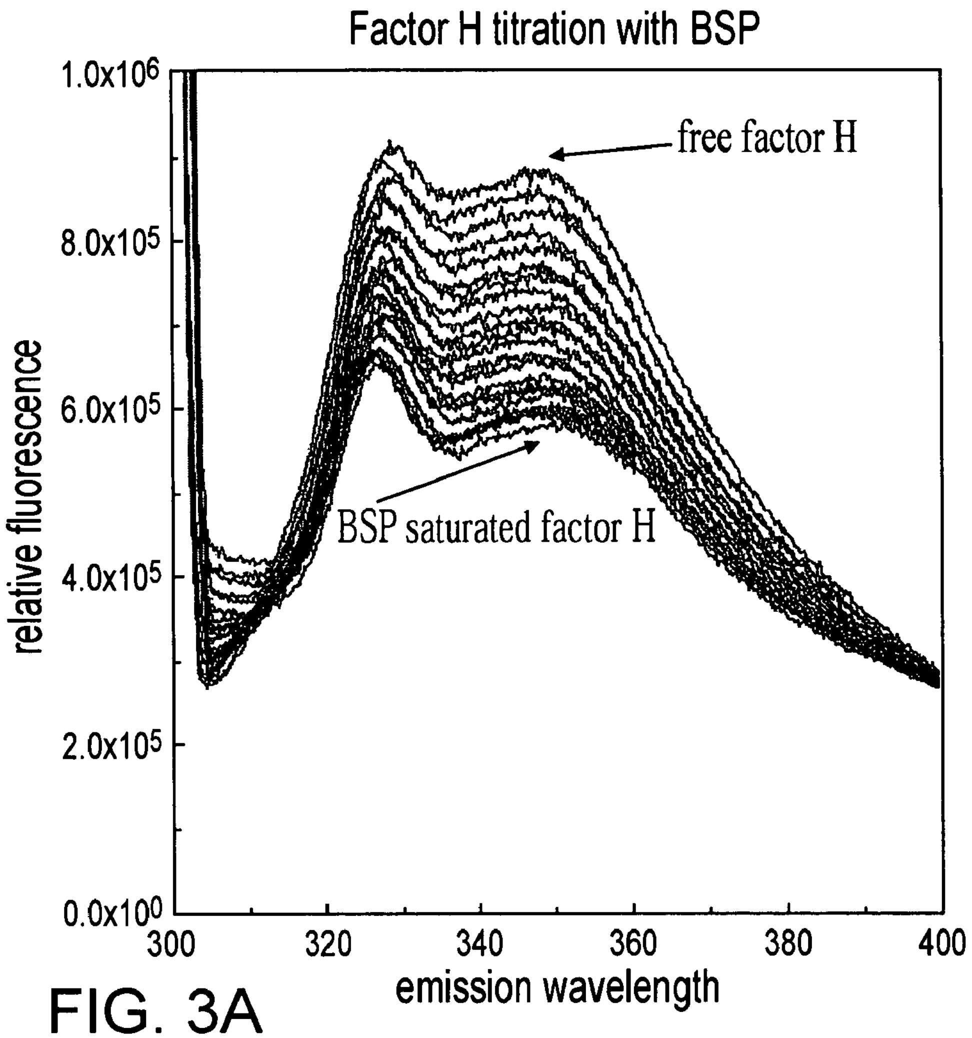
FIG. 3A
FIG. 3B
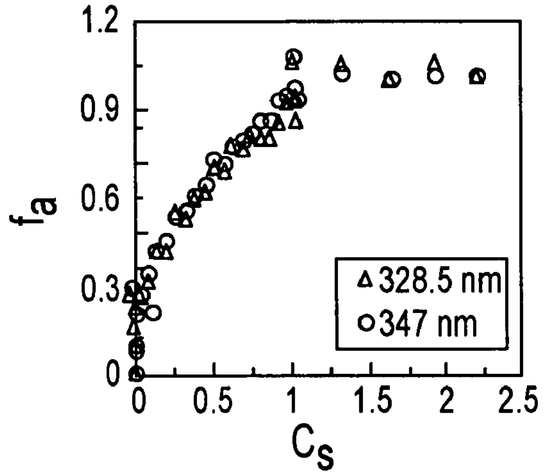

FIG. 5A
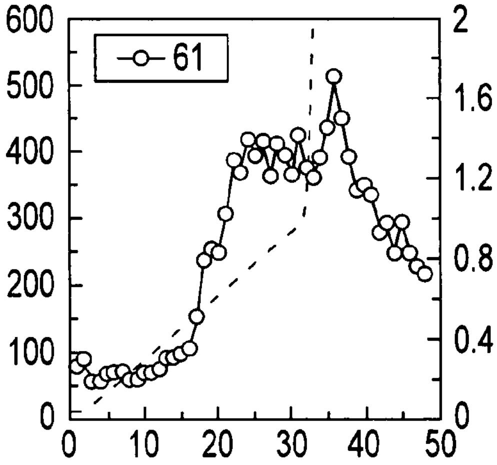
FIG. 5B
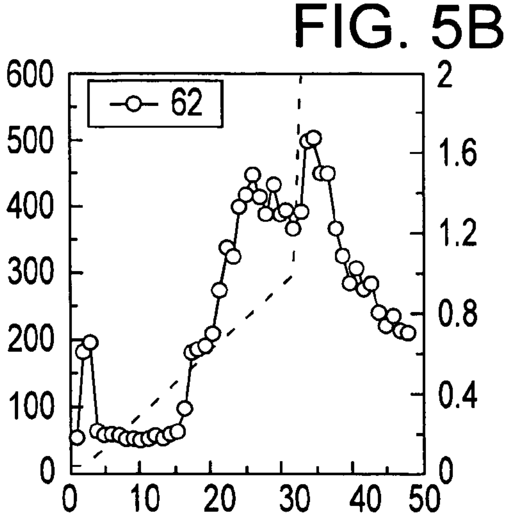
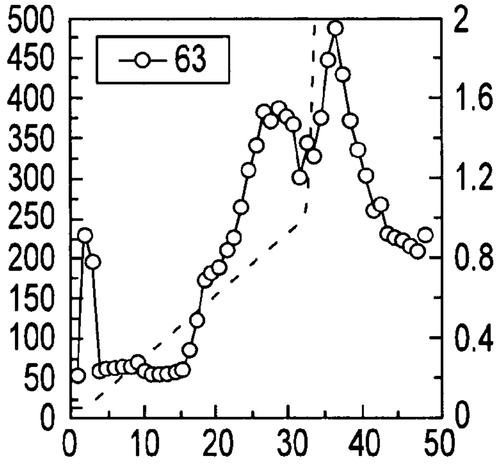
FIG. 5C
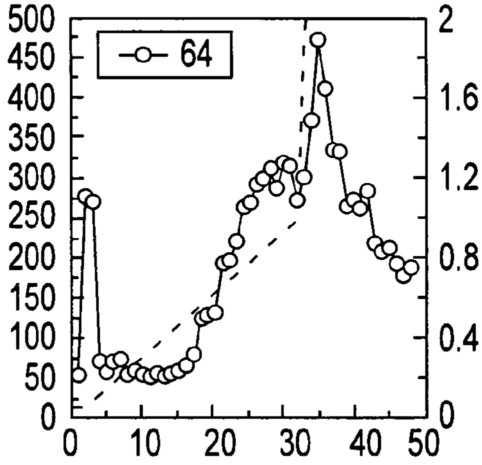
FIG. 5D
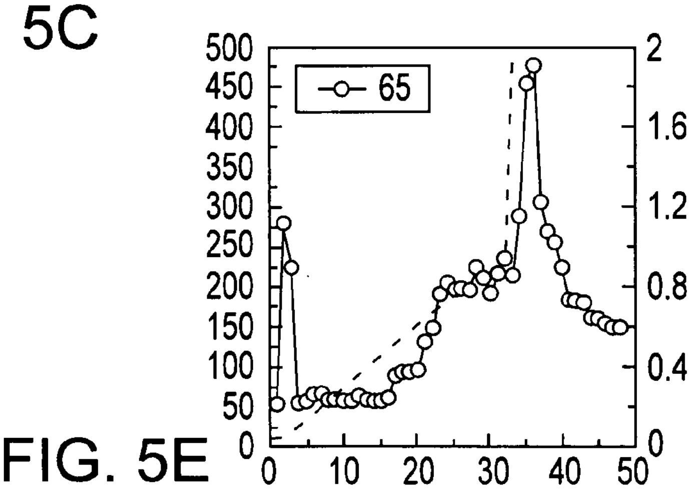
FIG. 5E

SEQUENCE LISTING

<160> NUMBER OF SEQ ID NOS: 18

<210> SEQ ID NO 1
<211> LENGTH: 317
<212> TYPE: PRT
<213> ORGANISM: Homo sapiens

<400> SEQUENCE: 1

Met Lys Thr Ala Leu Ile Leu Leu Ser Ile Leu Gly Met Ala Cys Ala
1 5 10 15

Phe Ser Met Lys Asn Leu His Arg Arg Val Lys Ile Glu Asp Ser Glu
20 25 30

Glu Asn Gly Val Phe Lys Tyr Arg Pro Arg Tyr Tyr Leu Tyr Lys His
35 40 45

Ala Tyr Phe Tyr Pro His Leu Lys Arg Phe Pro Val Gln Gly Ser Ser
50 55 60

Asp Ser Ser Glu Glu Asn Gly Asp Asp Ser Ser Glu Glu Glu Glu Glu
65 70 75 80

Glu Glu Glu Thr Ser Asn Glu Gly Glu Asn Asn Glu Glu Ser Asn Glu
85 90 95

Asp Glu Asp Ser Glu Ala Glu Asn Thr Thr Leu Ser Ala Thr Thr Leu
100 105 110

Gly Tyr Gly Glu Asp Ala Thr Pro Gly Thr Gly Tyr Thr Gly Leu Ala
115 120 125

Ala Ile Gln Leu Pro Lys Lys Ala Gly Asp Ile Thr Asn Lys Ala Thr
130 135 140

Lys Glu Lys Glu Ser Asp Glu Glu Glu Glu Glu Glu Glu Glu Gly Asn
145 150 155 160

Glu Asn Glu Glu Ser Glu Ala Glu Val Asp Glu Asn Glu Gln Gly Ile
165 170 175

Asn Gly Thr Ser Thr Asn Ser Thr Glu Ala Glu Asn Gly Asn Gly Ser
180 185 190

Ser Gly Gly Asp Asn Gly Glu Glu Gly Glu Glu Glu Ser Val Thr Gly
195 200 205

Ala Asn Ala Glu Gly Thr Thr Glu Thr Gly Gly Gln Gly Lys Gly Thr
210 215 220

Ser Lys Thr Thr Thr Ser Pro Asn Gly Gly Phe Glu Pro Thr Thr Pro
225 230 235 240

Pro Gln Val Tyr Arg Thr Thr Ser Pro Pro Phe Gly Lys Thr Thr Thr
245 250 255

Val Glu Tyr Glu Gly Glu Tyr Glu Tyr Thr Gly Val Asn Glu Tyr Asp
260 265 270

Asn Gly Tyr Glu Ile Tyr Glu Ser Glu Asn Gly Glu Pro Arg Gly Asp
275 280 285

Asn Tyr Arg Ala Tyr Glu Asp Glu Tyr Ser Tyr Phe Lys Gly Gln Gly
290 295 300

Tyr Asp Gly Tyr Asp Gly Gln Asn Tyr Tyr His His Gln
305 310 315

<210> SEQ ID NO 2
<211> LENGTH: 18
<212> TYPE: PRT
<213> ORGANISM: Artificial Sequence
<220> FEATURE:
<223> OTHER INFORMATION: Description of Artificial Sequence:immunogen -continued

<400> SEQUENCE: 2

```
Tyr Glu Ser Glu Asn Gly Glu Pro Arg Gly Asp Asn Tyr Arg Ala Tyr
  1               5                  10                  15

Glu Asp
```

```
<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence:immunogen

<400> SEQUENCE: 3

Ala Ile Gln Leu Pro Lys Lys Ala Gly Asp Ile Cys
  1               5                  10


<210> SEQ ID NO 4
<211> LENGTH: 60
<212> TYPE: PRT
<213> ORGANISM: Artificial Sequence
<220> FEATURE:
<223> OTHER INFORMATION: Description of Artificial Sequence:immunogen

<400> SEQUENCE: 4

Glu Tyr Glu Gly Glu Tyr Glu Tyr Thr Gly Val Asn Glu Tyr Asp Asn
  1               5                  10                  15

Gly Tyr Glu Ile Tyr Glu Ser Glu Asn Gly Glu Pro Arg Gly Asp Asn
             20                  25                  30

Tyr Arg Ala Tyr Glu Asp Glu Tyr Ser Tyr Phe Lys Gly Gln Gly Tyr
         35                  40                  45

Asp Gly Tyr Asp Gly Gln Asn Tyr Tyr His His Gln
     50                  55                  60


<210> SEQ ID NO 5
<211> LENGTH: 152
<212> TYPE: PRT
<213> ORGANISM: Artificial Sequence
<220> FEATURE:
<223> OTHER INFORMATION: Description of Artificial Sequence:immunogen

<400> SEQUENCE: 5

Ile Gln Leu Pro Lys Lys Ala Gly Asp Ile Thr Asn Lys Ala Thr Lys
  1               5                  10                  15

Glu Lys Glu Ser Asp Glu Glu Glu Glu Glu Glu Glu Glu Gly Asn Glu
             20                  25                  30

Asn Glu Glu Ser Glu Ala Glu Val Asp Glu Asn Glu Gln Gly Ile Asn
         35                  40                  45

Gly Thr Ser Thr Asn Ser Thr Glu Ala Glu Asn Gly Asn Gly Ser Ser
     50                  55                  60

Gly Gly Asp Asn Gly Glu Glu Gly Glu Glu Glu Ser Val Thr Gly Ala
 65                  70                  75                  80

Asn Ala Glu Gly Thr Thr Glu Thr Gly Gly Gln Gly Lys Gly Thr Ser
                 85                  90                  95

Lys Thr Thr Thr Ser Pro Asn Gly Gly Phe Glu Pro Thr Thr Pro Pro
            100                 105                 110

Gln Val Tyr Arg Thr Thr Ser Pro Pro Phe Gly Lys Thr Thr Thr Val
        115                 120                 125

Glu Tyr Glu Gly Glu Tyr Glu Tyr Thr Gly Val Asn Glu Tyr Asp Asn
    130                 135                 140
```

-continued

```
Gly Tyr Glu Ile Tyr Glu Ser Glu
145                 150


<210> SEQ ID NO 6
<211> LENGTH: 25
<212> TYPE: PRT
<213> ORGANISM: Artificial Sequence
<220> FEATURE:
<223> OTHER INFORMATION: Description of Artificial Sequence:immunogen

<400> SEQUENCE: 6

Val Phe Lys Tyr Arg Pro Arg Tyr Tyr Leu Tyr Lys His Ala Tyr Phe
  1               5                  10                  15

Tyr Pro His Leu Lys Arg Phe Pro Val
             20                  25


<210> SEQ ID NO 7
<211> LENGTH: 28
<212> TYPE: PRT
<213> ORGANISM: Artificial Sequence
<220> FEATURE:
<223> OTHER INFORMATION: Description of Artificial Sequence:immunogen
<220> FEATURE:
<221> NAME/KEY: VARIANT
<222> LOCATION: (5)
<223> OTHER INFORMATION: Sulfated
<220> FEATURE:
<221> NAME/KEY: VARIANT
<222> LOCATION: (9)
<223> OTHER INFORMATION: sulfated
<220> FEATURE:
<221> NAME/KEY: VARIANT
<222> LOCATION: (11)
<223> OTHER INFORMATION: sulfated
<220> FEATURE:
<221> NAME/KEY: VARIANT
<222> LOCATION: (17)
<223> OTHER INFORMATION: Sulfated
<220> FEATURE:
<221> NAME/KEY: VARIANT
<222> LOCATION: (21)
<223> OTHER INFORMATION: sulfated
<220> FEATURE:
<221> NAME/KEY: VARIANT
<222> LOCATION: (24)
<223> OTHER INFORMATION: sulfated

<400> SEQUENCE: 7

Cys Thr Val Glu Tyr Glu Gly Glu Tyr Glu Tyr Thr Gly Ala Asn Asp
  1               5                  10                  15

Tyr Asp Asn Gly Tyr Glu Ile Tyr Glu Ser Glu Asn
             20                  25


<210> SEQ ID NO 8
<211> LENGTH: 1037
<212> TYPE: DNA
<213> ORGANISM: Homo sapiens

<400> SEQUENCE: 8

ccttctctgc cctctcactc ccttgagcct gcttcctcac tccaggactg ccagaggaag     60

caatcaccaa aatgaagact gctttaattt tgctcagcat tttgggaatg gcctgtgctt    120

tctcaatgaa aaatttgcat cgaagagtca aaatagagga ttctgaagaa aatggggtct    180

ttaagtacag gccacgatat tatctttaca agcatgccta cttttatcct catttaaaac    240

gatttccagt tcagggcagt agtgactcat ccgaagaaaa tggagatgac agttcagaag    300

aggaggagga agaagaggag acttcaaatg aaggagaaaa caatgaagaa tcgaatgaag    360
```

-continued

```
atgaagactc tgaggctgag aataccacac tttctgctac aacactgggc tatggagagg    420

acgccacgcc tggcacaggg tatacagggt tagctgcaat ccagcttccc aagaaggctg    480

gggatataac aaacaaagct acaaaagaga aggaaagtga tgaagaagaa gaggaggaag    540

aggaaggaaa tgaaaacgaa gaaagcgaag cagaagtgga tgaaaacgaa caaggcataa    600

acggcaccag taccaacagc acagaggcag aaaacggcaa cggcagcagc ggaggagaca    660

atggagaaga aggggaagaa gaaagtgtca ctggagccaa tgcagaaggc accacagaga    720

ccggagggca gggcaagggc acctcgaaga caacaacctc tccaaatggt gggtttgaac    780

ctacaacccc accacaagtc tatagaacca cttccccacc ttttgggaaa accaccaccg    840

ttgaatacga gggggagtac gaatacacgg gcgtcaatga atacgacaat ggatatgaaa    900

tctatgaaag tgagaacggg gaacctcgtg ggacaattta ccgagcctat gaagatgagt    960

acagctactt taaaggacaa ggctacgatg gctatgatgg tcagaattac taccaccacc   1020

agtgaagctc cagcctg                                                  1037


<210> SEQ ID NO 9
<211> LENGTH: 24
<212> TYPE: PRT
<213> ORGANISM: Artificial Sequence
<220> FEATURE:
<221> NAME/KEY: THIOETH
<222> LOCATION: (2)..(17)
<220> FEATURE:
<223> OTHER INFORMATION: Description of Artificial Sequence: Immunogen

<400> SEQUENCE: 9

Glu Tyr Glu Tyr Thr Gly Val Asn Glu Tyr Asp Asn Gly Tyr Glu Ile
  1               5                  10                  15

Tyr Glu Ser Glu Asn Gly Glu Pro
             20


<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Competitor
      peptide

<400> SEQUENCE: 10

Gly Arg Gly Asp Ser
  1               5


<210> SEQ ID NO 11
<211> LENGTH: 1447
<212> TYPE: DNA
<213> ORGANISM: Homo sapiens
<220> FEATURE:
<221> NAME/KEY: CDS
<222> LOCATION: (109)..(1011)

<400> SEQUENCE: 11

gaggcagcag cagcaggagg aggcagacac agcatcgtcg ggaccagact cgtctcaggc     60

cagttgcagc cttctcagcc aaacgccgac caaggaaaac tcactacc atg aga att     117
                                                     Met Arg Ile
                                                       1

gca gtg att tgc ttt tgc ctc cta ggc atc acc tgt gcc ata cca gtt      165
Ala Val Ile Cys Phe Cys Leu Leu Gly Ile Thr Cys Ala Ile Pro Val
      5                  10                  15
```

-continued

```
aaa cag gct gat tct gga agt tct gag gaa aag cag ctt tac aac aaa       213
Lys Gln Ala Asp Ser Gly Ser Ser Glu Glu Lys Gln Leu Tyr Asn Lys
 20                  25                  30                  35

tac cca gat gct gtg gcc aca tgg cta aac cct gac cca tct cag aag       261
Tyr Pro Asp Ala Val Ala Thr Trp Leu Asn Pro Asp Pro Ser Gln Lys
                 40                  45                  50

cag aat ctc cta gcc cca cag acc ctt cca agt aag tcc aac gaa agc       309
Gln Asn Leu Leu Ala Pro Gln Thr Leu Pro Ser Lys Ser Asn Glu Ser
             55                  60                  65

cat gac cac atg gat gat atg gat gat gaa gat gat gat gac cat gtg       357
His Asp His Met Asp Asp Met Asp Asp Glu Asp Asp Asp Asp His Val
         70                  75                  80

gac agc cag gac tcc att gac tcg aac gac tct gat gat gta gat gac       405
Asp Ser Gln Asp Ser Ile Asp Ser Asn Asp Ser Asp Asp Val Asp Asp
     85                  90                  95

act gat gat tct cac cag tct gat gag tct cac cat tct gat gaa tct       453
Thr Asp Asp Ser His Gln Ser Asp Glu Ser His His Ser Asp Glu Ser
100                 105                 110                 115

gat gaa ctg gtc act gat ttt ccc acg gac ctg cca gca acc gaa gtt       501
Asp Glu Leu Val Thr Asp Phe Pro Thr Asp Leu Pro Ala Thr Glu Val
                120                 125                 130

ttc act cca gtt gtc ccc aca gta gac aca tat gat ggc cga ggt gat       549
Phe Thr Pro Val Val Pro Thr Val Asp Thr Tyr Asp Gly Arg Gly Asp
            135                 140                 145

agt gtg gtt tat gga ctg agg tca aaa tct aag aag ttt cgc aga cct       597
Ser Val Val Tyr Gly Leu Arg Ser Lys Ser Lys Lys Phe Arg Arg Pro
        150                 155                 160

gac atc cag tac cct gat gct aca gac gag gac atc acc tca cac atg       645
Asp Ile Gln Tyr Pro Asp Ala Thr Asp Glu Asp Ile Thr Ser His Met
    165                 170                 175

gaa agc gag gag ttg aat ggt gca tac aag gcc atc ccc gtt gcc cag       693
Glu Ser Glu Glu Leu Asn Gly Ala Tyr Lys Ala Ile Pro Val Ala Gln
180                 185                 190                 195

gac ctg aac gcg cct tct gat tgg gac agc cgt ggg aag gac agt tat       741
Asp Leu Asn Ala Pro Ser Asp Trp Asp Ser Arg Gly Lys Asp Ser Tyr
                200                 205                 210

gaa acg agt cag ctg gat gac cag agt gct gaa acc cac agc cac aag       789
Glu Thr Ser Gln Leu Asp Asp Gln Ser Ala Glu Thr His Ser His Lys
            215                 220                 225

cag tcc aga tta tat aag cgg aaa gcc aat gat gag agc aat gag cat       837
Gln Ser Arg Leu Tyr Lys Arg Lys Ala Asn Asp Glu Ser Asn Glu His
        230                 235                 240

tcc gat gtg att gat agt cag gaa ctt tcc aaa gtc agc cgt gaa ttc       885
Ser Asp Val Ile Asp Ser Gln Glu Leu Ser Lys Val Ser Arg Glu Phe
    245                 250                 255

cac agc cat gaa ttt cac agc cat gaa gat atg ctg gtt gta gac ccc       933
His Ser His Glu Phe His Ser His Glu Asp Met Leu Val Val Asp Pro
260                 265                 270                 275

aaa agt aag gaa gaa gat aaa cac ctg aaa ttt cgt att tct cat gaa       981
Lys Ser Lys Glu Glu Asp Lys His Leu Lys Phe Arg Ile Ser His Glu
                280                 285                 290

tta gat agt gca tct tct gag gtc aat taa aaggagaaaa aatacaattt        1031
Leu Asp Ser Ala Ser Ser Glu Val Asn
            295                 300

ctcactttgc atttagtcaa aagaaaaaat gctttatagc aaaatgaaag agaacatgaa   1091

atgcttcttt ctcagtttat tggttgaatg tgtatctatt tgagtctgga aataactaat   1151

gtgtttgata attagtttag tttgtggctt catggaaact ccctgtaaac taaaagcttc   1211

agggttatgt ctatgttcat tctatagaag aaatgcaaac tatcactgta ttttaatatt   1271
```

-continued

```
tgttattctc tcatgaatag aaatttatgt agaagcaaac aaaatacttt tacccactta   1331

aaaagagaat ataacatttt atgtcactat aatcttttgt tttttaagtt agtgtatatt   1391

ttgttgtgat tatctttttg tggtgtgaat aaatctttta tcttgaatgt aataag       1447


<210> SEQ ID NO 12
<211> LENGTH: 300
<212> TYPE: PRT
<213> ORGANISM: Homo sapiens

<400> SEQUENCE: 12

Met Arg Ile Ala Val Ile Cys Phe Cys Leu Leu Gly Ile Thr Cys Ala
  1               5                  10                  15

Ile Pro Val Lys Gln Ala Asp Ser Gly Ser Ser Glu Glu Lys Gln Leu
             20                  25                  30

Tyr Asn Lys Tyr Pro Asp Ala Val Ala Thr Trp Leu Asn Pro Asp Pro
         35                  40                  45

Ser Gln Lys Gln Asn Leu Leu Ala Pro Gln Thr Leu Pro Ser Lys Ser
     50                  55                  60

Asn Glu Ser His Asp His Met Asp Asp Met Asp Asp Glu Asp Asp Asp
 65                  70                  75                  80

Asp His Val Asp Ser Gln Asp Ser Ile Asp Ser Asn Asp Ser Asp Asp
                 85                  90                  95

Val Asp Asp Thr Asp Asp Ser His Gln Ser Asp Glu Ser His His Ser
            100                 105                 110

Asp Glu Ser Asp Glu Leu Val Thr Asp Phe Pro Thr Asp Leu Pro Ala
        115                 120                 125

Thr Glu Val Phe Thr Pro Val Val Pro Thr Val Asp Thr Tyr Asp Gly
    130                 135                 140

Arg Gly Asp Ser Val Val Tyr Gly Leu Arg Ser Lys Ser Lys Lys Phe
145                 150                 155                 160

Arg Arg Pro Asp Ile Gln Tyr Pro Asp Ala Thr Asp Glu Asp Ile Thr
                165                 170                 175

Ser His Met Glu Ser Glu Glu Leu Asn Gly Ala Tyr Lys Ala Ile Pro
            180                 185                 190

Val Ala Gln Asp Leu Asn Ala Pro Ser Asp Trp Asp Ser Arg Gly Lys
        195                 200                 205

Asp Ser Tyr Glu Thr Ser Gln Leu Asp Asp Gln Ser Ala Glu Thr His
    210                 215                 220

Ser His Lys Gln Ser Arg Leu Tyr Lys Arg Lys Ala Asn Asp Glu Ser
225                 230                 235                 240

Asn Glu His Ser Asp Val Ile Asp Ser Gln Glu Leu Ser Lys Val Ser
                245                 250                 255

Arg Glu Phe His Ser His Glu Phe His Ser His Glu Asp Met Leu Val
            260                 265                 270

Val Asp Pro Lys Ser Lys Glu Glu Asp Lys His Leu Lys Phe Arg Ile
        275                 280                 285

Ser His Glu Leu Asp Ser Ala Ser Ser Glu Val Asn
    290                 295                 300


<210> SEQ ID NO 13
<211> LENGTH: 1424
<212> TYPE: DNA
<213> ORGANISM: Homo sapiens
<220> FEATURE:
<221> NAME/KEY: CDS
```

-continued

```
<222> LOCATION: (68)..(1012)

<400> SEQUENCE: 13

gaccagactc gtctcaggcc agttgcagcc ttctcagcca aacgccgacc aaggaaaact      60

cactacc atg aga att gca gtg att tgc ttt tgc ctc cta ggc atc acc      109
        Met Arg Ile Ala Val Ile Cys Phe Cys Leu Leu Gly Ile Thr
          1               5                  10

tgt gcc ata cca gtt aaa cag gct gat tct gga agt tct gag gaa aag      157
Cys Ala Ile Pro Val Lys Gln Ala Asp Ser Gly Ser Ser Glu Glu Lys
 15                  20                  25                  30

cag ctt tac aac aaa tac cca gat gct gtg gcc aca tgg cta aac cct      205
Gln Leu Tyr Asn Lys Tyr Pro Asp Ala Val Ala Thr Trp Leu Asn Pro
                 35                  40                  45

gac cca tct cag aag cag aat ctc cta gcc cca cag aat gct gtg tcc      253
Asp Pro Ser Gln Lys Gln Asn Leu Leu Ala Pro Gln Asn Ala Val Ser
             50                  55                  60

tct gaa gaa acc aat gac ttt aaa caa gag acc ctt cca agt aag tcc      301
Ser Glu Glu Thr Asn Asp Phe Lys Gln Glu Thr Leu Pro Ser Lys Ser
         65                  70                  75

aac gaa agc cat gac cac atg gat gat atg gat gat gaa gat gat gat      349
Asn Glu Ser His Asp His Met Asp Asp Met Asp Asp Glu Asp Asp Asp
     80                  85                  90

gac cat gtg gac agc cag gac tcc att gac tcg aac gac tct gat gat      397
Asp His Val Asp Ser Gln Asp Ser Ile Asp Ser Asn Asp Ser Asp Asp
 95                 100                 105                 110

gta gat gac act gat gat tct cac cag tct gat gag tct cac cat tct      445
Val Asp Asp Thr Asp Asp Ser His Gln Ser Asp Glu Ser His His Ser
                115                 120                 125

gat gaa tct gat gaa ctg gtc act gat ttt ccc acg gac ctg cca gca      493
Asp Glu Ser Asp Glu Leu Val Thr Asp Phe Pro Thr Asp Leu Pro Ala
            130                 135                 140

acc gaa gtt ttc act cca gtt gtc ccc aca gta gac aca tat gat ggc      541
Thr Glu Val Phe Thr Pro Val Val Pro Thr Val Asp Thr Tyr Asp Gly
        145                 150                 155

cga ggt gat agt gtg gtt tat gga ctg agg tca aaa tct aag aag ttt      589
Arg Gly Asp Ser Val Val Tyr Gly Leu Arg Ser Lys Ser Lys Lys Phe
    160                 165                 170

cgc aga cct gac atc cag tac cct gat gct aca gac gag gac atc acc      637
Arg Arg Pro Asp Ile Gln Tyr Pro Asp Ala Thr Asp Glu Asp Ile Thr
175                 180                 185                 190

tca cac atg gaa agc gag gag ttg aat ggt gca tac aag gcc atc ccc      685
Ser His Met Glu Ser Glu Glu Leu Asn Gly Ala Tyr Lys Ala Ile Pro
                195                 200                 205

gtt gcc cag gac ctg aac gcg cct tct gat tgg gac agc cgt ggg aag      733
Val Ala Gln Asp Leu Asn Ala Pro Ser Asp Trp Asp Ser Arg Gly Lys
            210                 215                 220

gac agt tat gaa acg agt cag ctg gat gac cag agt gct gaa acc cac      781
Asp Ser Tyr Glu Thr Ser Gln Leu Asp Asp Gln Ser Ala Glu Thr His
        225                 230                 235

agc cac aag cag tcc aga tta tat aag cgg aaa gcc aat gat gag agc      829
Ser His Lys Gln Ser Arg Leu Tyr Lys Arg Lys Ala Asn Asp Glu Ser
    240                 245                 250

aat gag cat tcc gat gtg att gat agt cag gaa ctt tcc aaa gtc agc      877
Asn Glu His Ser Asp Val Ile Asp Ser Gln Glu Leu Ser Lys Val Ser
255                 260                 265                 270

cgt gaa ttc cac agc cat gaa ttt cac agc cat gaa gat atg ctg gtt      925
Arg Glu Phe His Ser His Glu Phe His Ser His Glu Asp Met Leu Val
                275                 280                 285

gta gac ccc aaa agt aag gaa gaa gat aaa cac ctg aaa ttt cgt att      973
```

-continued

```
Val Asp Pro Lys Ser Lys Glu Glu Asp Lys His Leu Lys Phe Arg Ile
            290                 295                 300

tct cat gaa tta gat agt gca tct tct gag gtc aat taa aaggagaaaa      1022
Ser His Glu Leu Asp Ser Ala Ser Ser Glu Val Asn
        305                 310                 315

aatacaattt ctcactttgc atttagtcaa aagaaaaaat gctttatagc aaaatgaaag   1082

agaacatgaa atgcttcttt ctcagtttat tggttgaatg tgtatctatt tgagtctgga   1142

aataactaat gtgtttgata attagtttag tttgtggctt catggaaact ccctgtaaac   1202

taaaagcttc agggttatgt ctatgttcat tctatagaag aaatgcaaac tatcactgta   1262

ttttaatatt tgttattctc tcatgaatag aaatttatgt agaagcaaac aaaatacttt   1322

tacccactta aaaagagaat ataacatttt atgtcactat aatcttttgt tttttaagtt   1382

agtgtatatt ttgttgtgat tatctttttg tggtgtgaat aa                      1424


<210> SEQ ID NO 14
<211> LENGTH: 314
<212> TYPE: PRT
<213> ORGANISM: Homo sapiens

<400> SEQUENCE: 14

Met Arg Ile Ala Val Ile Cys Phe Cys Leu Leu Gly Ile Thr Cys Ala
  1               5                  10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Asn Ala Val Ser Ser Glu
     50                  55                  60

Glu Thr Asn Asp Phe Lys Gln Glu Thr Leu Pro Ser Lys Ser Asn Glu
 65                  70                  75                  80

Ser His Asp His Met Asp Asp Met Asp Asp Glu Asp Asp Asp Asp His
                 85                  90                  95

Val Asp Ser Gln Asp Ser Ile Asp Ser Asn Asp Ser Asp Asp Val Asp
            100                 105                 110

Asp Thr Asp Asp Ser His Gln Ser Asp Glu Ser His His Ser Asp Glu
        115                 120                 125

Ser Asp Glu Leu Val Thr Asp Phe Pro Thr Asp Leu Pro Ala Thr Glu
    130                 135                 140

Val Phe Thr Pro Val Val Pro Thr Val Asp Thr Tyr Asp Gly Arg Gly
145                 150                 155                 160

Asp Ser Val Val Tyr Gly Leu Arg Ser Lys Ser Lys Lys Phe Arg Arg
                165                 170                 175

Pro Asp Ile Gln Tyr Pro Asp Ala Thr Asp Glu Asp Ile Thr Ser His
            180                 185                 190

Met Glu Ser Glu Glu Leu Asn Gly Ala Tyr Lys Ala Ile Pro Val Ala
        195                 200                 205

Gln Asp Leu Asn Ala Pro Ser Asp Trp Asp Ser Arg Gly Lys Asp Ser
    210                 215                 220

Tyr Glu Thr Ser Gln Leu Asp Asp Gln Ser Ala Glu Thr His Ser His
225                 230                 235                 240

Lys Gln Ser Arg Leu Tyr Lys Arg Lys Ala Asn Asp Glu Ser Asn Glu
                245                 250                 255

His Ser Asp Val Ile Asp Ser Gln Glu Leu Ser Lys Val Ser Arg Glu
            260                 265                 270
```

-continued

```
Phe His Ser His Glu Phe His Ser His Glu Asp Met Leu Val Val Asp
        275                 280                 285

Pro Lys Ser Lys Glu Glu Asp Lys His Leu Lys Phe Arg Ile Ser His
    290                 295                 300

Glu Leu Asp Ser Ala Ser Ser Glu Val Asn
305                 310


<210> SEQ ID NO 15
<211> LENGTH: 2682
<212> TYPE: DNA
<213> ORGANISM: Homo sapiens
<220> FEATURE:
<221> NAME/KEY: CDS
<222> LOCATION: (100)..(1641)

<400> SEQUENCE: 15

tgggcataga tttcctcttt gagaacatca acctgatttt tgagactttt tgaaaaaatt      60

ctttgtgaac tacggagggt agaggtatca cacccaact atg aag atc agc atc       114
                                           Met Lys Ile Ser Ile
                                            1               5

ctg ctc atg ttc ctt tgg gga tta tcc tgt gct ctc cca gta acc agg      162
Leu Leu Met Phe Leu Trp Gly Leu Ser Cys Ala Leu Pro Val Thr Arg
                10                  15                  20

tat caa aat aat gaa tct gag gat tct gaa gaa tgg aag ggt cat ttg      210
Tyr Gln Asn Asn Glu Ser Glu Asp Ser Glu Glu Trp Lys Gly His Leu
            25                  30                  35

gct cag gca cca aca cca ccc ttg gag agc agt gag tca tca gaa ggc      258
Ala Gln Ala Pro Thr Pro Pro Leu Glu Ser Ser Glu Ser Ser Glu Gly
        40                  45                  50

agt aaa gtt agc tca gag gaa cag gca aat gaa gac ccc agt gac agc      306
Ser Lys Val Ser Ser Glu Glu Gln Ala Asn Glu Asp Pro Ser Asp Ser
    55                  60                  65

act cag tca gag gag ggc ctg ggc tct gat gat cat caa tac att tat      354
Thr Gln Ser Glu Glu Gly Leu Gly Ser Asp Asp His Gln Tyr Ile Tyr
 70                  75                  80                  85

agg cta gct ggt ggc ttc tcc agg agc aca gga aaa gga gga gat gat      402
Arg Leu Ala Gly Gly Phe Ser Arg Ser Thr Gly Lys Gly Gly Asp Asp
                90                  95                 100

aaa gat gac gat gaa gat gac agt gga gat gac acc ttt ggt gac gat      450
Lys Asp Asp Asp Glu Asp Asp Ser Gly Asp Asp Thr Phe Gly Asp Asp
            105                 110                 115

gac agt ggc cca ggg ccc aaa gac aga caa gaa gga gga aac tcc aga      498
Asp Ser Gly Pro Gly Pro Lys Asp Arg Gln Glu Gly Gly Asn Ser Arg
        120                 125                 130

ctg gga agt gat gag gac tct gat gac acc ata caa gcc agt gaa gag      546
Leu Gly Ser Asp Glu Asp Ser Asp Asp Thr Ile Gln Ala Ser Glu Glu
    135                 140                 145

agt gcc cca caa ggg caa gac agt gcc caa gat acc acc agt gag agc      594
Ser Ala Pro Gln Gly Gln Asp Ser Ala Gln Asp Thr Thr Ser Glu Ser
150                 155                 160                 165

agg gaa ctt gac aat gag gac cgg gtg gac agc aag cct gag gga ggt      642
Arg Glu Leu Asp Asn Glu Asp Arg Val Asp Ser Lys Pro Glu Gly Gly
                170                 175                 180

gac tcc act caa gag agt gag agt gaa gag cac tgg gtg gga ggt ggc      690
Asp Ser Thr Gln Glu Ser Glu Ser Glu Glu His Trp Val Gly Gly Gly
            185                 190                 195

agt gat ggg gag agc agc cat gga gac ggc tcc gag ttg gac gat gag      738
Ser Asp Gly Glu Ser Ser His Gly Asp Gly Ser Glu Leu Asp Asp Glu
        200                 205                 210
```

-continued

```
gga atg cag agt gat gac cca gag agc atc agg agt gaa agg gga aac      786
Gly Met Gln Ser Asp Asp Pro Glu Ser Ile Arg Ser Glu Arg Gly Asn
    215                 220                 225

tcc aga atg aac agt gca ggc atg aaa tca aaa gaa tct gga gaa aac      834
Ser Arg Met Asn Ser Ala Gly Met Lys Ser Lys Glu Ser Gly Glu Asn
230                 235                 240                 245

agt gag caa gca aac act caa gat tca ggt ggc agc caa ttg ctg gag      882
Ser Glu Gln Ala Asn Thr Gln Asp Ser Gly Gly Ser Gln Leu Leu Glu
                250                 255                 260

cat ccc agt agg aaa att ttt agg aag tct cgc atc tca gag gaa gat      930
His Pro Ser Arg Lys Ile Phe Arg Lys Ser Arg Ile Ser Glu Glu Asp
            265                 270                 275

gac aga agc gag ctt gat gac aac aac aca atg gaa gaa gtc aag agt      978
Asp Arg Ser Glu Leu Asp Asp Asn Asn Thr Met Glu Glu Val Lys Ser
        280                 285                 290

gac tct aca gaa aac agc aac tcc aga gac act ggc ctc agc caa ccc     1026
Asp Ser Thr Glu Asn Ser Asn Ser Arg Asp Thr Gly Leu Ser Gln Pro
    295                 300                 305

agg aga gac agc aag ggt gac tct caa gaa gac agc aag gag aat ctg     1074
Arg Arg Asp Ser Lys Gly Asp Ser Gln Glu Asp Ser Lys Glu Asn Leu
310                 315                 320                 325

tcc cag gaa gag agc caa aac gta gat ggt ccc agc agt gag tcc agc     1122
Ser Gln Glu Glu Ser Gln Asn Val Asp Gly Pro Ser Ser Glu Ser Ser
                330                 335                 340

caa gag gcc aac ctg tca tct caa gag aac agc agt gag tct cag gaa     1170
Gln Glu Ala Asn Leu Ser Ser Gln Glu Asn Ser Ser Glu Ser Gln Glu
            345                 350                 355

gag gtg gtg agt gag tcc agg gga gat aac ccc gac ccc aca act agt     1218
Glu Val Val Ser Glu Ser Arg Gly Asp Asn Pro Asp Pro Thr Thr Ser
        360                 365                 370

tat gta gaa gac cag gaa gac agt gac tcc agc gag gag gac agc tcg     1266
Tyr Val Glu Asp Gln Glu Asp Ser Asp Ser Ser Glu Glu Asp Ser Ser
    375                 380                 385

cac aca ctc tcc cac tca aaa agt gaa tcc aga gag gag caa gca gac     1314
His Thr Leu Ser His Ser Lys Ser Glu Ser Arg Glu Glu Gln Ala Asp
390                 395                 400                 405

agc gaa tcc agt gag agc ctc aac ttc tca gag gaa agc ccg gag tcc     1362
Ser Glu Ser Ser Glu Ser Leu Asn Phe Ser Glu Glu Ser Pro Glu Ser
                410                 415                 420

cct gag gat gag aac agc tcc agc cag gag ggc ctc cag tct cac agc     1410
Pro Glu Asp Glu Asn Ser Ser Ser Gln Glu Gly Leu Gln Ser His Ser
            425                 430                 435

agc tca gca gag agt cag agc gag gaa agc cat tct gag gaa gac gac     1458
Ser Ser Ala Glu Ser Gln Ser Glu Glu Ser His Ser Glu Glu Asp Asp
        440                 445                 450

agt gac tct caa gac agc agc aga tcc aaa gaa gat agc aac tcc acg     1506
Ser Asp Ser Gln Asp Ser Ser Arg Ser Lys Glu Asp Ser Asn Ser Thr
    455                 460                 465

gag agc aaa tca agc agt gag gaa gat ggc cag ttg aaa aac att gag     1554
Glu Ser Lys Ser Ser Ser Glu Glu Asp Gly Gln Leu Lys Asn Ile Glu
470                 475                 480                 485

ata gag agc cgg aaa tta aca gtt gat gcc tat cac aac aaa ccc att     1602
Ile Glu Ser Arg Lys Leu Thr Val Asp Ala Tyr His Asn Lys Pro Ile
                490                 495                 500

ggg gac caa gat gac aat gac tgc caa gac ggc tat tag catcagctgt      1651
Gly Asp Gln Asp Asp Asn Asp Cys Gln Asp Gly Tyr
            505                 510

cctaagaagc agttgtcaca taaaggagtc ttagggactt gaaaatgtat catgataact   1711

ataatttatt gatgttttga tcaaaagaat aaccagatgc catatttttc ctgaaaggaa   1771
```

-continued

```
ttgctggaca ttacacttgt ttttagggtg tcatcatttc acagaggttt aaatactgtg   1831

gagtgacacc agtaacacag ccaaagaggc tagtaagcaa gaaaggatct gcatgataac   1891

tttgcagctg agatagttcc taattcatca acgtaacaaa caaagctatt gggtgtccat   1951

gtatatacca ggcactatgc taggtgttga gaatgtaaag caggttaaga cttgtttctt   2011

gctcctgagg agcgtataga ggggacccac gtagctaaca gagttaacag aggggtatgt   2071

ataagagaaa cgtgaatagt tacaacccag tatgctgagt gccaaggcca gtgaggctat   2131

gaacacgata tcaatctggg gacactgaga aggataacca atgcgttgga gaacgaggga   2191

ggacttcata gcagaagaat tggagttgga aggttgcata gggtttcctc attggagacc   2251

ggggaattct attcttggga taaataatag taaattctat aggattcaat acttagtttg   2311

caaaagcact ttgaaattat ggcacagtga gttgttttgg ataagaaaat ctttttctcc   2371

caattaattt accaattcat catttttttt ttttgtagaa ctcccataaa catcacctta   2431

ctaatcactg gtgatgataa gaaggattgg gtcaggaaga gtgggagaaa gaaattcctc   2491

tttacgtaga tactttttag ctttattttt tctaaaatca gtttgcgtgc aatgctagaa   2551

aaaaactgtt ctctgagtcc tttacagagc aaaattctgt atgtaagatt caattgattt   2611

ttgacaaata ccatttgaaa tattacctca acataaaata cttgttttgt aataaagatt   2671

ataataccca g                                                        2682
```

<210> SEQ ID NO 16
<211> LENGTH: 513
<212> TYPE: PRT
<213> ORGANISM: Homo sapiens

<400> SEQUENCE: 16

```
Met Lys Ile Ser Ile Leu Leu Met Phe Leu Trp Gly Leu Ser Cys Ala
  1               5                  10                  15

Leu Pro Val Thr Arg Tyr Gln Asn Asn Glu Ser Glu Asp Ser Glu Glu
             20                  25                  30

Trp Lys Gly His Leu Ala Gln Ala Pro Thr Pro Pro Leu Glu Ser Ser
         35                  40                  45

Glu Ser Ser Glu Gly Ser Lys Val Ser Ser Glu Glu Gln Ala Asn Glu
     50                  55                  60

Asp Pro Ser Asp Ser Thr Gln Ser Glu Glu Gly Leu Gly Ser Asp Asp
 65                  70                  75                  80

His Gln Tyr Ile Tyr Arg Leu Ala Gly Gly Phe Ser Arg Ser Thr Gly
                 85                  90                  95

Lys Gly Gly Asp Asp Lys Asp Asp Asp Glu Asp Asp Ser Gly Asp Asp
            100                 105                 110

Thr Phe Gly Asp Asp Asp Ser Gly Pro Gly Pro Lys Asp Arg Gln Glu
        115                 120                 125

Gly Gly Asn Ser Arg Leu Gly Ser Asp Glu Asp Ser Asp Asp Thr Ile
    130                 135                 140

Gln Ala Ser Glu Glu Ser Ala Pro Gln Gly Gln Asp Ser Ala Gln Asp
145                 150                 155                 160

Thr Thr Ser Glu Ser Arg Glu Leu Asp Asn Glu Asp Arg Val Asp Ser
                165                 170                 175

Lys Pro Glu Gly Gly Asp Ser Thr Gln Glu Ser Glu Ser Glu Glu His
            180                 185                 190

Trp Val Gly Gly Gly Ser Asp Gly Glu Ser Ser His Gly Asp Gly Ser
        195                 200                 205
```

```
Glu Leu Asp Asp Glu Gly Met Gln Ser Asp Asp Pro Glu Ser Ile Arg
    210                 215                 220

Ser Glu Arg Gly Asn Ser Arg Met Asn Ser Ala Gly Met Lys Ser Lys
225                 230                 235                 240

Glu Ser Gly Glu Asn Ser Glu Gln Ala Asn Thr Gln Asp Ser Gly Gly
                245                 250                 255

Ser Gln Leu Leu Glu His Pro Ser Arg Lys Ile Phe Arg Lys Ser Arg
            260                 265                 270

Ile Ser Glu Glu Asp Asp Arg Ser Glu Leu Asp Asp Asn Asn Thr Met
        275                 280                 285

Glu Glu Val Lys Ser Asp Ser Thr Glu Asn Ser Asn Ser Arg Asp Thr
    290                 295                 300

Gly Leu Ser Gln Pro Arg Arg Asp Ser Lys Gly Asp Ser Gln Glu Asp
305                 310                 315                 320

Ser Lys Glu Asn Leu Ser Gln Glu Glu Ser Gln Asn Val Asp Gly Pro
                325                 330                 335

Ser Ser Glu Ser Ser Gln Glu Ala Asn Leu Ser Ser Gln Glu Asn Ser
            340                 345                 350

Ser Glu Ser Gln Glu Glu Val Val Ser Glu Ser Arg Gly Asp Asn Pro
        355                 360                 365

Asp Pro Thr Thr Ser Tyr Val Glu Asp Gln Glu Asp Ser Asp Ser Ser
    370                 375                 380

Glu Glu Asp Ser Ser His Thr Leu Ser His Ser Lys Ser Glu Ser Arg
385                 390                 395                 400

Glu Glu Gln Ala Asp Ser Glu Ser Ser Glu Ser Leu Asn Phe Ser Glu
                405                 410                 415

Glu Ser Pro Glu Ser Pro Glu Asp Glu Asn Ser Ser Ser Gln Glu Gly
            420                 425                 430

Leu Gln Ser His Ser Ser Ser Ala Glu Ser Gln Ser Glu Glu Ser His
        435                 440                 445

Ser Glu Glu Asp Asp Ser Asp Ser Gln Asp Ser Ser Arg Ser Lys Glu
    450                 455                 460

Asp Ser Asn Ser Thr Glu Ser Lys Ser Ser Ser Glu Glu Asp Gly Gln
465                 470                 475                 480

Leu Lys Asn Ile Glu Ile Glu Ser Arg Lys Leu Thr Val Asp Ala Tyr
                485                 490                 495

His Asn Lys Pro Ile Gly Asp Gln Asp Asp Asn Asp Cys Gln Asp Gly
            500                 505                 510

Tyr
```

<210> SEQ ID NO 17
<211> LENGTH: 8201
<212> TYPE: DNA
<213> ORGANISM: Homo sapiens
<220> FEATURE:
<221> NAME/KEY: exon
<222> LOCATION: (2387)..(2437)
<220> FEATURE:
<221> NAME/KEY: exon
<222> LOCATION: (3577)..(3660)
<220> FEATURE:
<221> NAME/KEY: exon
<222> LOCATION: (3794)..(4780)
<220> FEATURE:
<221> NAME/KEY: exon
<222> LOCATION: (5257)..(7896)

<400> SEQUENCE: 17

-continued

```
attgtcatgc aaaagtccag gacagtgggc cactttcagt cttcaaagag aaagataaga     60
aattctggat tttcaaaatc cttttgaagc cttttaaggt aagatgaaat atccttttta    120
ctcagaacca actgattcat ttagaaagaa ctttgaattt caaagatgaa gccagtttga    180
ttttaagaag cgagtacccc ttaatgatta gattgtatgc ttcctttttg acttgtcata    240
ttgatagtat gtataaaaga taacggacga ttacgaccta aggaagagat agattgggaa    300
gaagaaagac ctcgtactga aaaattggcc aactgaggtg gaaatttgac aattaactat    360
ctgggcactt tgattagttt tgataaaaaa tgagataact cagatttcaa aaatccacct    420
tgggctttca aacaaggctt caattaggct ttgcttttta gtattttatt acttactatt    480
acttattatt tattgtccca catgaaatga aatttagcaa tcactaatga tgccaaatct    540
aattgctaaa tgaaatgaag ctaaatctca tttcattagt aacaataaat gaaataatct    600
gatggagctt cacaaattct gaagtctttg tttcatgctg aggtcacctg ggccattttt    660
attgtagtct tcgaagtcat tcacctgcct tggaaacggt gataaccatc atggaattgt    720
tcaggagtgg agctgaaaga gagatgtagt ggtcagattt ctgaactgta gctcagaaac    780
tggacacgta tcactctggc cttggctgca ggtacctttc cagtatgctg aggctcttcc    840
aaatcacagt gcagacgggc cttctgcaga gctatgtaat gattaggctt gggactgcaa    900
agtacaggat aactgtggct tagtaaacag ctggccttca acatctgtgc cccagagctc    960
tgcatgatac ttgtcctggt gtcacctcag cctcacttga atctatggca tttcagaagg   1020
agctctagct gttcttggct ttctgttgaa cagctataag aatgagcact tttttccctc   1080
tcagtagctc tggaactgtg tcatctctcc tgtgagaaaa cgccagtaat tctcatgaca   1140
gttgatattc agtgaagttt tattatattt tcactaccac cattaaattc aatcaaagcc   1200
attttatgac atgcagcatt ataatctata catctggtgg gagttcatga aataggagta   1260
aaactctcct ttctatcatt acttcaagaa atccaacttg caatataaat taattttttt   1320
actcacacag attataaaat gtctattcca acttatcaga aacatgtttt agaccatttc   1380
tgaatttgaa ttctaacagg gatgaagaat catgatttta gaagtcccat aaaataattg   1440
ctatcattta ttcaaaaatt gcaaagtgcc tgaagcaatg ctagatattg ctgatagtca   1500
taaatattta tcaacaacat tcagaaaacg tttttttctg tgctttgcat tggaatacaa   1560
taatcaccaa gacactctcc tgggcctcag gagcttacag gaaatcaggg caacacataa   1620
gtaactaggc aattttaaac agtgcaatgc gttaccagtg agacgtgcaa acttccttgg   1680
tataaaaagg aaagagatac caaataccct ttgaagtggc gtcagagagg gcgtctcaga   1740
gataattcta ccaaacttca ggataatcct gaggtgcagg tgttgttatt attccaggtg   1800
gagggataat aaacctactt aaatttctca agcttacaca gcaagtagca ggggtaacat   1860
ttgaacccag gtctctgaat acaaaccccg tattctttcc actagcgtag gctccctcat   1920
gttagtaatt tctttctctt aaagtctggt atagctcaat tctatagatt tggagtaagg   1980
atgacaagtg ttttaccttt gaagcacaat ttcagcagaa ttagttagta cttgattaaa   2040
gctattcaga agagaaatag atgtttttac acccaagaat tgcagaagaa caaagttaca   2100
gctatgccct ttgtacctat tatggtgttt tccttcattg gcacaggcag aaaaaaatct   2160
aggaagctac attagtgctg agcctggtga tgtccccata accacaccag gtatgttctg   2220
gaccatcgta tgtcttctcg tgttagatac atgcttcttg tccaggaaaa gggcaaatgc   2280
ttacacatca aaataatata gtactatgat tttcccttta ctttataagt aattttgtgc   2340
```

-continued

```
tgttcctttt ttatacagcc attgattatt attattccta aagaaaatga agataattac   2400
atatttttgc atttgggcag tagcatgggc cattccagta agtatgcctt tcttagaaaa   2460
cctcttcact ttgttatctt ttttaaccta acattaatac aaaatgtagt gtgtgtgtgt   2520
gtgtgtgtgt gtgtgtgtgt gtgcatgtac atgtgtgtat atatgtgtgt gtgtatatat   2580
gtttccttaa tttttttttaa caggctgagt ctaaacattt agatttgcac taagggcttt   2640
atgtgatatc tgtgaggttt caacaaaacc actccaattc atcgtctcat tcctctatag   2700
aaactcatat ctcgtctgaa ggattattat tatttaaaac atttattcag attaatttac   2760
acttaatgcc cagaagtcat ggagactttg tccatctttg cttcatactc tgtgaatttc   2820
attctaatac gaacaaagtc tgtgctgttt aggaagtttc caagaaagaa taataagaaa   2880
aagtagattt tttttcaaca tataggagac taatttttca ctcagagtta ttatttatgt   2940
gctcactgtg gaaaatttgg aatatatgac gaaaaccaat aaaaaattga gaaaattcaa   3000
ccatttataa ttttactagc cagccatcat gtttaacatt ttcatatgct ttcataatac   3060
caaacatttg gtatttatgt agttgaaaat gttctcaagt atttcaaatg tgctcttgca   3120
gagcacagaa gtatactagc gtaatacttg attttgcttc tgtgcaggct ctggtcacgc   3180
ctcctgttct cttaagagtt ttcatcagga ttacacttag agcgggtttg tgctagtgca   3240
agaggctttt tgtagagaaa caccagaggt ctatcccctc gtctttctac aagactcttt   3300
ccttctacag ttgagataag tgggctgatc taacacgtcc ataaaattgg taataccaca   3360
gtgaaaaata tccatgtacc cagtttaaat tctacacaag ccctgtaaga agccacttct   3420
cttttctatc tgattagatc atactttggc ctttgtgtta aacctttctt cttcatggag   3480
ggaagaatat ttgtgtgtgt gtgtgtgtgt gtgcacgctc acacacatat tcacaaataa   3540
gaacctttttc aatagccagt attttctact tggcaggttc ctcaaagcaa accactggag   3600
agacatgtcg aaaaatccat gaatttgcat ctcctagcaa gatcaaatgt gtcagtacag   3660
gtataggatg taatatattt cattttattt cctatttctg agttgctaca ttccattaac   3720
ttctccaaga ttgcaatttg ctttccttca agatcattga cactcataat tgattgaatt   3780
gtttcttttt caggatgagt taaatgccag tggaaccatc aaagaaagtg gtgtcctggt   3840
gcatgaaggt gatagaggaa ggcaagagaa tacccaagat ggtcacaagg gagaagggaa   3900
tggctctaag tgggcagaag taggagggaa gagtttttct acatattcca cattagcaaa   3960
cgaagagggg aatattgagg gctggaatgg ggacacagga aaagcagaaa catatggtca   4020
tgatggaata catgggaaag aagaaaacat cacagcaaat ggcatccagg gacaagtaag   4080
catcattgac aatgctggag ccacaaacag aagcaacact aatggaaata ctgataagaa   4140
tacccaaaat ggggatgttg gcgatgcagg tcacaatgag gatgtcgctg ttgtccaaga   4200
agatggacct caagtagctg gaagcaataa cagtacagac aatgaggatg aaataattga   4260
gaattcctgt agaaacgagg gtaatacaag tgaaataaca cctcagatca acagcaagag   4320
aaatgggact aaggaagctg aggtaacacc aggcactgga gaagatgctg gcctggataa   4380
ttccgatggg agtcctagtg ggaatggagc agatgaggat gaagacgagg gttctggtga   4440
tgatgaagat gaagaagcag ggaatggaaa agacagtagt aataacagca agggccagga   4500
gggccaggac catgggaaag aagatgatca tgatagtagc ataggtcaaa attcggatag   4560
taaagaatat tatgaccctg aaggcaaaga agatccccat aatgaagttg atggagacaa   4620
gacctccaag agtgaggaga attctgctgg tattccagaa gacaatggca gccaaagaat   4680
agaggacacc cagaagctca accatagaga aagcaaacgc gtagaaaata gaatcaccaa   4740
```

-continued

```
agaatcagag acacatgctg ttgggaagag ccaagataag gttagtttgt aaagctgatt   4800
tctttcaatg gcagtttaaa ttcttcccct ccatctattg atgctagcac aaaaataaac   4860
catgacaagc atccatgtat ttttgtatcc atattacttg actatttaag gaaatctaga   4920
gtccttacta gacttcgaga tagaacaact ttaaacatct tacatttctg ataacttagt   4980
tataattcta gaaaagtctt atgtgaaatc atggatcccc atgtaattgt ttacaaaagt   5040
tcctactggg taggaatgtg gatgaatttt taaggaatct aagcaccagg atgctttcaa   5100
ttacagaata aagcacattt tcacaaataa ctgtgaagta ctagaaatgt aactcctatc   5160
cctatggcaa cttttcccag ttattcttcc tcagatcaat gcaattttgc agcaaatatt   5220
cactagttaa tcattctttc ctccatcctt ccatagggaa tagaaatcaa gggtcccagc   5280
agtggcaaca gaaatattac caaagaagtt gggaaaggca acgaaggtaa agaggataaa   5340
ggacaacatg gaatgatctt gggcaaaggc aatgtcaaga cacaaggaga ggttgtcaac   5400
atagaaggac ctggccaaaa atcagaacca ggaaataaag ttggacacag caatacaggt   5460
agtgacagca atagtgatgg atatgacagt tatgattttg atgataagtc catgcaagga   5520
gatgatccca atagcagtga tgaatctaat ggcaatgatg atgctaattc agaaagtgac   5580
aataacagca gtagccgagg agatgcttct tataactctg atgaatcaaa agataatggc   5640
aatggcagtg actcaaaagg agcagaagat gatgacagtg atagcacatc agacactaat   5700
aatagtgaca gtaatggcaa tggtaacaat gggaatgatg acaatgacaa atcagacagt   5760
ggcaaaggta aatcagatag cagtgacagt gatagtagtg atagcagcaa tagcagtgat   5820
agtagtgaca gcagtgacag tgacagcagt gatagcaaca gtagcagtga tagtgacagc   5880
agtgacagtg acagcagtga tagcagtgac agtgatagta gtgatagcag caatagcagt   5940
gacagtagtg acagcagtga tagcagtgac agtagtgata gtagtgacag cagtgacagc   6000
aagtcagaca gcagcaaatc agagagcgac agcagtgata gtgacagtaa gtcagacagc   6060
agtgacagca acagcagtga cagtagtgac aacagtgata gcagcgacag cagcaatagc   6120
agtaacagca gtgatagtag tgacagcagt gatagcagtg acagcagcag tagcagtgac   6180
agcagcagta gcagtgacag cagcaacagc agtgatagta gtgacagtag tgacagcagc   6240
aatagcagtg agagcagtga tagtagtgac agcagtgata gtgacagcag tgatagtagt   6300
gacagcagta atagtaacag cagcgatagt gacagcagca acagcagcga tagcagtgac   6360
agcagtgata gcagtgacag cagcaacagc agtgacagta gcgatagcag tgacagcagc   6420
aacagcagtg acagcagtga tagcagtgac agcagtgata gtagtgacag cagcaacagc   6480
agtgatagca acgacagcag caatagcagt gacagcagtg atagcagcaa cagcagtgat   6540
agcagcaaca gcagtgatag cagtgatagc agtgacagca gtgatagcga cagcagcaat   6600
agcagtgaca gcagtaatag tagtgacagc agcgatagca gcaacagcag tgatagcagc   6660
gacagcagcg atagcagtga cagcagtgat agcgacagca gcaatagaag tgacagtagt   6720
aatagtagtg acagcagcga tagcagtgac agcagcaaca gcagtgacag cagtgatagt   6780
agtgacagca gtgacagcaa cgaaagcagc aatagcagtg acagcagtga tagcagcaac   6840
agcagtgata gtgacagcag tgatagcagc aacagcagtg acagcagtga tagcagcaac   6900
agcagtgata gcagtgaaag cagtaatagt agtgacaaca gcaatagcag tgacagcagc   6960
aacagcagtg acagcagtga tagcagtgac agcagtaata gtagtgacag cagcaatagc   7020
ggtgacagca gcaacagcag tgacagcagt gatagcaata gcagcgacag cagtgacagc   7080
```

-continued

```
agcaacagca gcgatagcag tgacagcagt gatagcagtg acagcagtga cagcagtgat   7140

agcagcaaca gcagtgatag cagtgacagc agtgacagca gtgatagcag taatagtagt   7200

gacagcagca acagcagtga cagcagcgat agcagtgaca gcagcgatag cagtgacagc   7260

agtgacagca gcaatagcag tgacagcagt gacagcagcg acagcagtga tagcagtgac   7320

agcagtggca gcagcgacag cagtgatagc agtgacagca gtgatagcag cgatagcagt   7380

gacagcagcg acagcagtga cagcagtgac agcagtgaaa gcagcgacag cagcgatagc   7440

agcgacagca gtgacagcag cgacagcagt gacagcagcg atagcagcga cagcagcgac   7500

agcagcgata gcagtgacag cagcaatagc agtgatagca gcgacagcag tgatagcagt   7560

gacagcagcg acagcagcga tagcagcgac agcagtgata gtagtgatag cagtgacagc   7620

agtgacagca gcgacagcag tgacagcagc gacagcagtg acagcagcga cagcagtgac   7680

agcaatgaaa gcagcgacag cagtgacagc agcgatagca gtgacagcag caacagcagt   7740

gacagcagcg acagcagtga tagcagtgac agcacatctg acagcaatga tgagagtgac   7800

agccagagca agtctggtaa cggtaacaac aatggaagtg acagtgacag tgacagtgaa   7860

ggcagtgaca gtaaccactc aaccagtgat gattagaaca aaagaaaaac ccataagatt   7920

ccttttgtga aaagtttggt aatgggatag gaaaaaaaga tttccaagaa agtaaagaaa   7980

ggggagaaat aaacataaga cgtatgtaaa caaaaacaac tgggggaatc aaatcaaaca   8040

gttggattca gaaccaagac ctaactcctg cagagacaga ctctgaatgc atgacctttg   8100

gtacatgcct gttaatattc atgttctgaa aatattttgt taaaagtgta aatctaaaca   8160

taaaagaaca attaaaatat tctttaatac ttcacacaga a                       8201

<210> SEQ ID NO 18
<211> LENGTH: 1253
<212> TYPE: PRT
<213> ORGANISM: Homo sapiens

<400> SEQUENCE: 18

Met Lys Ile Ile Thr Tyr Phe Cys Ile Trp Ala Val Ala Trp Ala Ile
  1               5                  10                  15

Pro Val Pro Gln Ser Lys Pro Leu Glu Arg His Val Glu Lys Ser Met
             20                  25                  30

Asn Leu His Leu Leu Ala Arg Ser Asn Val Ser Val Gln Asp Glu Leu
         35                  40                  45

Asn Ala Ser Gly Thr Ile Lys Glu Ser Gly Val Leu Val His Glu Gly
     50                  55                  60

Asp Arg Gly Arg Gln Glu Asn Thr Gln Asp Gly His Lys Gly Glu Gly
 65                  70                  75                  80

Asn Gly Ser Lys Trp Ala Glu Val Gly Gly Lys Ser Phe Ser Thr Tyr
                 85                  90                  95

Ser Thr Leu Ala Asn Glu Glu Gly Asn Ile Glu Gly Trp Asn Gly Asp
            100                 105                 110

Thr Gly Lys Ala Glu Thr Tyr Gly His Asp Gly Ile His Gly Lys Glu
        115                 120                 125

Glu Asn Ile Thr Ala Asn Gly Ile Gln Gly Gln Val Ser Ile Ile Asp
    130                 135                 140

Asn Ala Gly Ala Thr Asn Arg Ser Asn Thr Asn Gly Asn Thr Asp Lys
145                 150                 155                 160

Asn Thr Gln Asn Gly Asp Val Gly Asp Ala Gly His Asn Glu Asp Val
                165                 170                 175
```

-continued

```
Ala Val Val Gln Glu Asp Gly Pro Gln Val Ala Gly Ser Asn Asn Ser
            180                 185                 190

Thr Asp Asn Glu Asp Glu Ile Ile Glu Asn Ser Cys Arg Asn Glu Gly
        195                 200                 205

Asn Thr Ser Glu Ile Thr Pro Gln Ile Asn Ser Lys Arg Asn Gly Thr
    210                 215                 220

Lys Glu Ala Glu Val Thr Pro Gly Thr Gly Glu Asp Ala Gly Leu Asp
225                 230                 235                 240

Asn Ser Asp Gly Ser Pro Ser Gly Asn Gly Ala Asp Glu Asp Glu Asp
                245                 250                 255

Glu Gly Ser Gly Asp Asp Glu Asp Glu Glu Ala Gly Asn Gly Lys Asp
            260                 265                 270

Ser Ser Asn Asn Ser Lys Gly Gln Glu Gly Gln Asp His Gly Lys Glu
        275                 280                 285

Asp Asp His Asp Ser Ser Ile Gly Gln Asn Ser Asp Ser Lys Glu Tyr
    290                 295                 300

Tyr Asp Pro Glu Gly Lys Glu Asp Pro His Asn Glu Val Asp Gly Asp
305                 310                 315                 320

Lys Thr Ser Lys Ser Glu Glu Asn Ser Ala Gly Ile Pro Glu Asp Asn
                325                 330                 335

Gly Ser Gln Arg Ile Glu Asp Thr Gln Lys Leu Asn His Arg Glu Ser
            340                 345                 350

Lys Arg Val Glu Asn Arg Ile Thr Lys Glu Ser Glu Thr His Ala Val
        355                 360                 365

Gly Lys Ser Gln Asp Lys Gly Ile Glu Ile Lys Gly Pro Ser Ser Gly
    370                 375                 380

Asn Arg Asn Ile Thr Lys Glu Val Gly Lys Gly Asn Glu Gly Lys Glu
385                 390                 395                 400

Asp Lys Gly Gln His Gly Met Ile Leu Gly Lys Gly Asn Val Lys Thr
                405                 410                 415

Gln Gly Glu Val Val Asn Ile Glu Gly Pro Gly Gln Lys Ser Glu Pro
            420                 425                 430

Gly Asn Lys Val Gly His Ser Asn Thr Gly Ser Asp Ser Asn Ser Asp
        435                 440                 445

Gly Tyr Asp Ser Tyr Asp Phe Asp Asp Lys Ser Met Gln Gly Asp Asp
    450                 455                 460

Pro Asn Ser Ser Asp Glu Ser Asn Gly Asn Asp Asp Ala Asn Ser Glu
465                 470                 475                 480

Ser Asp Asn Asn Ser Ser Ser Arg Gly Asp Ala Ser Tyr Asn Ser Asp
                485                 490                 495

Glu Ser Lys Asp Asn Gly Asn Gly Ser Asp Ser Lys Gly Ala Glu Asp
            500                 505                 510

Asp Asp Ser Asp Ser Thr Ser Asp Thr Asn Asn Ser Asp Ser Asn Gly
        515                 520                 525

Asn Gly Asn Asn Gly Asn Asp Asp Asn Asp Lys Ser Asp Ser Gly Lys
    530                 535                 540

Gly Lys Ser Asp Ser Ser Asp Ser Asp Ser Ser Asp Ser Ser Asn Ser
545                 550                 555                 560

Ser Asp Ser Ser Asp Ser Ser Asp Ser Asp Ser Ser Asp Ser Asn Ser
                565                 570                 575

Ser Ser Asp Ser Asp Ser Ser Asp Ser Asp Ser Ser Asp Ser Ser Asp
            580                 585                 590

Ser Asp Ser Ser Asp Ser Ser Asn Ser Ser Asp Ser Ser Asp Ser Ser
```

-continued

```
        595                 600                 605

Asp Ser Ser Asp Ser Ser Asp Ser Ser Asp Ser Ser Asp Ser Lys Ser
    610                 615                 620

Asp Ser Ser Lys Ser Glu Ser Asp Ser Ser Asp Ser Asp Ser Lys Ser
625                 630                 635                 640

Asp Ser Ser Asp Ser Asn Ser Ser Asp Ser Ser Asp Asn Ser Asp Ser
                645                 650                 655

Ser Asp Ser Ser Asn Ser Ser Asn Ser Ser Asp Ser Ser Asp Ser Ser
            660                 665                 670

Asp Ser Ser Asp Ser Ser Ser Ser Ser Asp Ser Ser Ser Ser Ser Asp
        675                 680                 685

Ser Ser Asn Ser Ser Asp Ser Ser Asp Ser Ser Asp Ser Ser Asn Ser
    690                 695                 700

Ser Glu Ser Ser Asp Ser Ser Asp Ser Ser Asp Ser Asp Ser Ser Asp
705                 710                 715                 720

Ser Ser Asp Ser Ser Asn Ser Asn Ser Ser Asp Ser Asp Ser Ser Asn
                725                 730                 735

Ser Ser Asp Ser Ser Asp Ser Ser Asp Ser Ser Asp Ser Ser Asn Ser
            740                 745                 750

Ser Asp Ser Ser Asp Ser Ser Asp Ser Ser Asn Ser Ser Asp Ser Ser
        755                 760                 765

Asp Ser Ser Asp Ser Ser Asp Ser Ser Asp Ser Ser Asn Ser Ser Asp
    770                 775                 780

Ser Asn Asp Ser Ser Asn Ser Ser Asp Ser Ser Asp Ser Ser Asn Ser
785                 790                 795                 800

Ser Asp Ser Ser Asn Ser Ser Asp Ser Ser Asp Ser Ser Asp Ser Ser
                805                 810                 815

Asp Ser Asp Ser Ser Asn Ser Ser Asp Ser Ser Asn Ser Ser Asp Ser
            820                 825                 830

Ser Asp Ser Ser Asn Ser Ser Asp Ser Ser Asp Ser Ser Asp Ser Ser
        835                 840                 845

Asp Ser Ser Asp Ser Asp Ser Ser Asn Arg Ser Asp Ser Ser Asn Ser
    850                 855                 860

Ser Asp Ser Ser Asp Ser Ser Asp Ser Ser Asn Ser Ser Asp Ser Ser
865                 870                 875                 880

Asp Ser Ser Asp Ser Ser Asp Ser Asn Glu Ser Ser Asn Ser Ser Asp
                885                 890                 895

Ser Ser Asp Ser Ser Asn Ser Ser Asp Ser Asp Ser Ser Asp Ser Ser
            900                 905                 910

Asn Ser Ser Asp Ser Ser Asp Ser Ser Asn Ser Ser Asp Ser Ser Glu
        915                 920                 925

Ser Ser Asn Ser Ser Asp Asn Ser Asn Ser Ser Asp Ser Ser Asn Ser
    930                 935                 940

Ser Asp Ser Ser Asp Ser Ser Asp Ser Ser Asn Ser Ser Asp Ser Ser
945                 950                 955                 960

Asn Ser Gly Asp Ser Ser Asn Ser Ser Asp Ser Ser Asp Ser Asn Ser
                965                 970                 975

Ser Asp Ser Ser Asp Ser Ser Asn Ser Ser Asp Ser Ser Asp Ser Ser
            980                 985                 990

Asp Ser Ser Asp Ser Ser Asp Ser Ser Asp Ser Ser Asn Ser Ser Asp
        995                1000                1005

Ser Ser Asp Ser Ser Asp Ser Ser Asp Ser Ser Asn Ser Ser Asp Ser
   1010                1015                1020
```

-continued

```
Ser Asn Ser Ser Asp Ser Ser Asp Ser Ser Asp Ser Ser Asp Ser Ser
1025                1030                1035                1040

Asp Ser Ser Asp Ser Ser Asn Ser Ser Asp Ser Ser Asp Ser Ser Asp
                1045                1050                1055

Ser Ser Asp Ser Ser Asp Ser Ser Gly Ser Ser Asp Ser Ser Asp Ser
            1060                1065                1070

Ser Asp Ser Ser Asp Ser Ser Asp Ser Ser Asp Ser Ser Asp Ser Ser
        1075                1080                1085

Asp Ser Ser Asp Ser Ser Glu Ser Ser Asp Ser Ser Asp Ser Ser Asp
    1090                1095                1100

Ser Ser Asp Ser Ser Asp Ser Ser Asp Ser Ser Asp Ser Ser Asp Ser
1105                1110                1115                1120

Ser Asp Ser Ser Asp Ser Ser Asp Ser Ser Asn Ser Ser Asp Ser Ser
                1125                1130                1135

Asp Ser Ser Asp Ser Ser Asp Ser Ser Asp Ser Ser Asp Ser Ser Asp
            1140                1145                1150

Ser Ser Asp Ser Ser Asp Ser Ser Asp Ser Ser Asp Ser Ser Asp Ser
        1155                1160                1165

Ser Asp Ser Ser Asp Ser Ser Asp Ser Ser Asp Ser Ser Asp Ser Asn
    1170                1175                1180

Glu Ser Ser Asp Ser Ser Asp Ser Ser Asp Ser Ser Asp Ser Ser Asn
1185                1190                1195                1200

Ser Ser Asp Ser Ser Asp Ser Ser Asp Ser Ser Asp Ser Thr Ser Asp
                1205                1210                1215

Ser Asn Asp Glu Ser Asp Ser Gln Ser Lys Ser Gly Asn Gly Asn Asn
            1220                1225                1230

Asn Gly Ser Asp Ser Asp Ser Asp Ser Glu Gly Ser Asp Ser Asn His
        1235                1240                1245

Ser Thr Ser Asp Asp
    1250
```

COMPLEX FORMED BY N-LINKED GLYCOPROTEINS (SIBLINGS)AND FACTOR H

PRIORITY CLAIM

This is a § 371 U.S. national stage of PCT/US00/09349 filed Apr. 7, 2000, which was published in English under PCT Article 21(2), which in turn claims the benefit of U.S. Provisional Application 60/128,468 filed Apr. 9, 1999.

FIELD OF THE INVENTION

The present invention relates to methods of detecting and utilizing small integrin-binding ligand, N-linked glycoproteins (SIBLNGS), as well as the production and use of recombinant SIBLINGS proteins that can be used as controls for such detection methods.

BACKGROUND OF THE INVENTION

A. Factor H

Factor H, a 150-kDa protein, is a key regulatory braking mechanism in normal and alternate complement-mediated cell lysis. It dissociates and thereby inactivates the assembled C3 convertase, serves as an essential accelerator of Factor I-mediated cleavage of C3b to iC3b, and sterically inhibits C5 binding to C3b (a prerequisite step for terminal pathway activation). The salient structural features of Factor H include 20 short consensus repeats (SCRs) that contain four cysteine residues forming two disulfide bonds per repeat. In addition, each SCR contains at least one conserved tryptophan residue per repeat, and Factor H is known to interact with several sialic acid-containing proteins.

B. Molecular Characterization of BSP, A Member of the SIBLINGS Protein Family Bone sialoprotein (BSP), also briefly known as BSPII, is a phosphorylated and sulfated glycoprotein that is associated with most normal and many pathological mineralized matrices. It is a small (approximate Mr=75,000) integrin-binding protein that supports cell attachment in vitro through both RGD-dependent and RGD-independent mechanisms and has a high affinity for hydroxyapatite. BSP is a member of the family of small integrin-binding ligand, N-linked glycoproteins (SIBLINGS) family that also includes osteopontin (OPN), dentin matrix protein (DMP1) and dentin sialophosphoprotein (DSPP). All have similar gene structures and are clustered on human chromosome 4.

Bone sialoprotein (BSP) constitutes about 10–15% of the non-collagenous proteins found in the mineralized compartment of young bone (Fisher et el., *J. Biol. Chem.* 258: 12723–727, 1983). Immunolocalization and in situ studies have shown BSP to be produced by osteoblasts, osteocytes, and osteoclasts (the multinucleated cells that resorb bone) (Bianco et al., *Calcif. Tissue Int.* 49:421–426, 1991). The areas richest in BSP are the collagen-poor matrix found between areas of new bone, where bone is developing or turning over. Outside of bone, BSP has been found in other mineralized tissues, such as dentin (Fisher et al., *J. Biol. Chem.* 258:12723–727. 1983), cementum (MacNeil et al., *J. Bone Min. Res.* 9:1597–1606, 1994), and calcifying cartilage of the growth plate (Bianco et al., *Calcif. Tissue Int.* 49:421–426, 1991). Trophoblasts of the developing placenta also express high levels of BSP (Bianco et al., *Calcified Tissue International,* 49:421–426, 1991). While placental tissue is not usually considered to be a mineralized tissue, late term human placentas have hydroxyapatite crystals associated with the aging trophoblasts.

Using human BSP as a model (Fisher et al., *J. Biol. Chem.* 265:2347–2351, 1990), the protein is first made as a 317 amino acid, 35,000 Da protein. A 16 amino acid leader peptide is removed during synthesis. BSP has no disulfide bonds and it is nearly uniformly hydrophilic along its length, indicating that the protein is likely to be an extended rod in solution. There are three regions particularly rich in glutamic acids residues ("polyglutamic acid domains") that have long been thought to govern the high affinity of this protein for hydroxyapatite. Recent work with recombinant fragments, however, shows that BSP's ability to bind strongly to apatite is found throughout its length (Stubbs et al., *Bone Miner. Res.* 12:1210–1222, 1997).

Human BSP contains four consensus sequences for N-inked oligosaccharides, three of which are conserved for all mammalian species known to date. These N-linked and the many O-linked oligosaccharides make up approximately 50% of the mass of BSP as it is secreted into the human bone matrix (Fisher et al., *J. Biol. Chem.* 258:12723–727, 1983). Tyrosine sulfation and serine/threonine phosphorylation make up the remainder of the known post translational modifications. There are three tyrosine-rich domains in BSP, the last two of which flank the RGD domain and are subject to sulfation. The presence or absence of the sulfate groups does not appear to change the ability of fibroblasts to attach in a simple in vitro assay (Mintz et al., *J. Biol. Chem.* 269:4845–4852, 1994).

The cDNA BSP sequences for rat (Oldberg et al., *J. Biol. Chem.* 263:19430–19432, 1988), human (Fisher et al., *J. Biol. Chem.* 265:2347–2351, 1990), mouse (Young et al., *Mamm. Genome* 5:108–111, 1994), cow (Chenu et al., *J. Bone Miner. Res.* 9:417–421, 1994), hamster (Sasaguri et al., Direct submission to GenBank, Accession number U65889, 1996) and chicken (Yang et al., *J. Bone Miner. Res.* 10:632–440, 1995) have been published. The human (Kerr, J. M., Fisher, L. W., Termine, J. D., Wang, M. G., McBride, O. W. and Young, M. F. *Genomics* 17:408–415, 1993) and chicken (Yang, R. and Gerstenfeld, L. C., *J. Cell. Biochem.* 64:77–93, 1997) genes have also been published. The human IBSP gene maps very close to two other members of this family, within 340 kb of SPPI (osteopontin), and within 150 kb of DMP1 with the order being: cen-DMP1-IBSP-SPPI-tel on chromosome 4 (Aplin et al., *Genomics* 30:347–349, 1995; Crosby et al., *Genome* 7:149–151, 1996). Mouse Tbsp is on the homologous region of chromosome 5 at 56.0 (Young et al., *Mamm. Genome* 5:108–111, 1994). Other members of the family are also encoded on chromosome 4, for example dentin phosphoprotein and dentin sialoprotein (DSPP) are cleavage products expressed from a single transcript coded by a gene on human chromosome 4 (MacDougall et al., J. Biol. Chem. 272(2):835, 1997).

C. Detection of Human BSP

The detection of human BSP in biological samples has been accomplished using polyclonal antibodies directed towards denatured whole BSP, non-denatured whole BSP, or synthetic fragments of BSP. Certain tumors have been found to ectopically express BSP. For example, BSP has been found to be expressed by breast cancer tissue, prostate cancer tissue, lung cancer tissue and thyroid cancer tissue (Bellahcene et al., *Cancer Research* 54:823–826, 1994; Bellahcene et al., *Calcif. Tissue Int.* 61:183–188, 1998; Bellahcene et al., *Calcif. Tissue Int.* 61:183–188, 1997; and Bellahcene et al., *Thyroid* 8:637–641, 1998 respectively). Additional studies have shown that BSP mRNA levels are increased in human breast cancer tissue as well as cell lines derived from breast cancer tissue (Bellachcene et al., *Laboratory Investigation* 75:203–210, 1996).

The detection of BSP in various tissue samples described above has been accomplished through the use of polyclonal antibodies directed to either whole human BSP (LF-6) or synthetic fragments of human BSP, such as the synthetic fragment comprising amino acids 277–294 (LF-83).

An increased level of BSP in serum has been correlated with the presence of hyperparathyroidism, Paget's disease, multiple myeloma and breast cancer (Seibel, et al., *J. Clinical Endocrinology and Metabolism,* 81:3289–294, 1996). Elevated levels of serum BSP have also been detected in subjects suffering from rheumatoid arthritis (Mansson et al., *J. Clin. Invest.* 95:1071–1077, 1995).

SUMMARY OF THE INVENTION

The present invention stems from the discovery that members of the SIBLINGS family of proteins bind to Factor H and that these proteins can confer resistance to complement mediated lysis. This discovery also allows for the creation of assays that more accurately determine the total quantity of SIBLINGS proteins in samples, and for the creation of methods of utilizing SIBLINGS proteins to inhibit complement formation.

The present invention also takes advantage of the recognition that the population of BSP (one member of the SIBLINGS family of proteins) in serum contains two distinct sub-populations. The first sub-population of BSP is relatively non-acidic, and it is the predominant sub-population found in normal subjects. The second sub-population of BSP is relatively acidic and it is found predominantly in subjects with various types of tumors. Accordingly, the invention also provides methods of detecting the relatively acidic BSP and the relatively non-acidic BSP. Furthermore, these methods can be practiced for example, by using monoclonal antibodies specific for either the relatively acidic BSP or by simply separating the different forms of BSP based upon their ionic charges.

One embodiment of the invention involves detecting at least one member of the SIBLINGS family of proteins in a manner that Factor H does not inhibit the detection of the SIBLINGS protein. The detection of the SIBLINGS protein can occur in vivo or in vito, for example in the context of a sample.

In another embodiment the invention provides methods of detecting the SIBLINGS protein by separating the SIBLINGS protein from the SIBLINGS/Factor H complex and then detecting the SIBLINGS protein. Separation of the SIBLINGS protein from Factor H can be accomplished in a variety of ways, for example by heating the sample in the presence of reducing agents such as DTT (1,4-dithiothreitol) and β-mercaptoethanol. These methods can also incorporate the use of denaturants such as urea, SDS, and formamide.

Factor H can also be separated from the SIBLINGS protein based upon the differences between the ionic charge of the SIBLINGS protein and Factor H. Factor H can also be separated from the SIBLINGS protein by reacting a SIBLINGS/Factor H complex with a specific binding agent.

The specific binding agent can be specific for the portion of the SIBLINGS protein that is exposed in the SIBLINGS/Factor H complex or it can be specific for the SIBLINGS/Factor H complex itself. When the specific binding agent is specific for the SIBLINGS/Factor H complex itself it is not necessary to separate the SIBLINGS protein from Factor H prior to detection. Furthermore, in some instances the specific binding agent can serve to separate and identify the SIBLINGS protein simultaneously.

The invention also provides methods of making specific binding agents that detect the exposed portion of SIBLINGS proteins when they are complexed to Factor H as well as specific binding agents that specifically detect the SIBLINGS/Factor H complex. Accordingly, the invention also provides compositions containing these specific binding agents.

The methods provided by the invention are particularly useful for screening for the presence or the recurrence of a tumor, such as a liquid tumor, prostate tumor, thyroid tumor, lung tumor, or breast tumor that is associated with abnormal SIBLINGS protein production. The methods can be practiced for example, by testing samples of body fluids, such as blood, serum, or saliva. In some instances the tumor may produce a relatively acidic SIBLINGS protein, such as BSP, and therefore, the invention provides methods of detecting the relatively acidic BSP population.

Accordingly, the invention provides transformed organisms that expresses recombinant SIBLINGS proteins such as BSP, OPN, DSPP, and DMP1 (rBSP, rOPN, rDSPP, and rDMP1, respectively). This organism can express full length SIBLINGS proteins or fragments thereof, more specifically the organism can express the BSP molecule encoded by the construct shown in SEQ ID NO: 8. This recombinantly produced BSP can then be purified for use in a variety of different applications.

In another embodiment the invention provides a method of conferring protection from a complement mediated immune response a subject. This method involves providing a reservoir or other supply in the subjects body from which a SIBLINGS protein can be dispersed to interfere with complement mediated lysis and inflammation. For example a cell or an implant can be contacted (for example coated) with a SIBLINGS protein. When such a coated implant is introduced into the body, it will provoke less of an inflammatory response. In the case of a cell, a recombinant nucleic acid sequence can be introduced via transformation and the cell will then express the SIBLINGS protein. This embodiment is useful for protecting cells that are grafted onto foreign tissue or for protecting bone marrow cells that are being introduced into a foreign host. Alternatively, a reservoir of SIBLINGS protein is placed in the body for metered dispensing of the protein in therapeutic dosages.

In another embodiment of the invention the SIBLINGS protein can be detected in a subject that is suspected of having abnormal bone turnover, for example abnormal bone turnover associated with osteoporosis.

These and other aspects of the invention will become readily apparent in light of the description provided below.

BRIEF DESCRIPTION OF THE FIGURES

FIG. 1A shows a chromatograph of biotinylated BSP. FIG. 1B shows biotinylated BSP preincubated with normal human serum, and FIG. 1C shows biotinylated BSP preincubated with Factor H.

FIG. 2A shows a chromatograph of normal human serum (NHS). FIG. 2B shows biotinylated BSP-(btBSP) incubated with normal human serum and FIG.

2C shows normal human serum after incubation with DTT in the presence of formamide and heat.

FIGS. 3A and 3B are graphs which show the result of a titration of Factor H with BSP. FIG. 3A shows relative fluorescence of Factor H, and Factor H complexed with BSP. FIG. 3B shows the fractional acceptor saturation ($f_a$) vs. the molar ratio of BSP to Factor H($C_s$), the latter of which was constant throughout the assay. This figure shows that BSP binds 1:1 with Factor H and has a binding constant of ≦1 nM. Similar results were seen with OPN and DMP1.

Figure 4A:
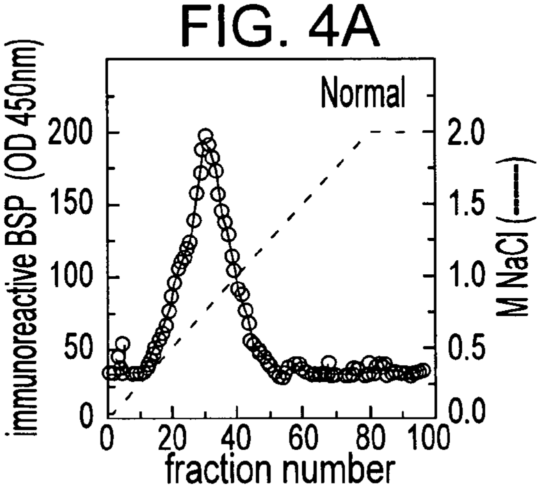
Figure 4B:
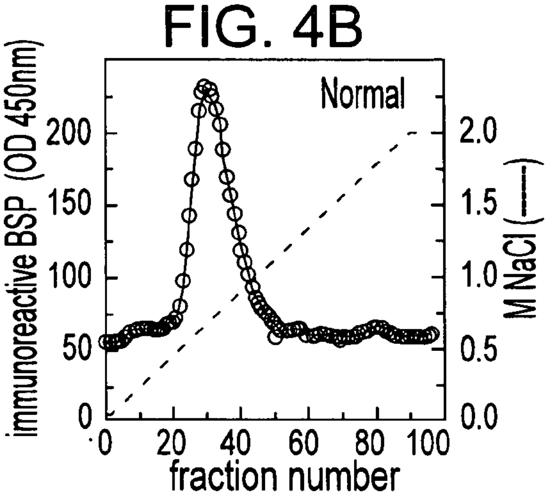
Figure 4C:
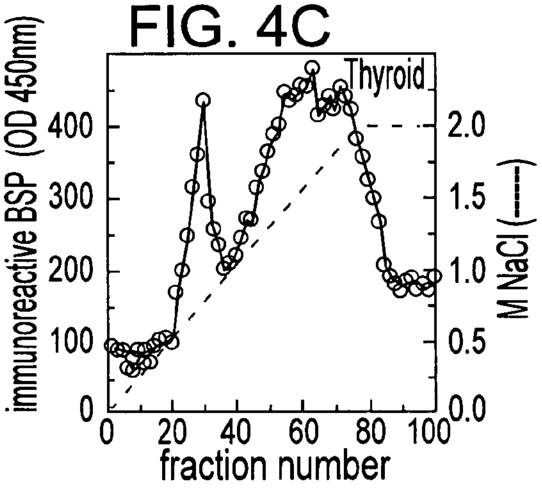
Figure 4D:
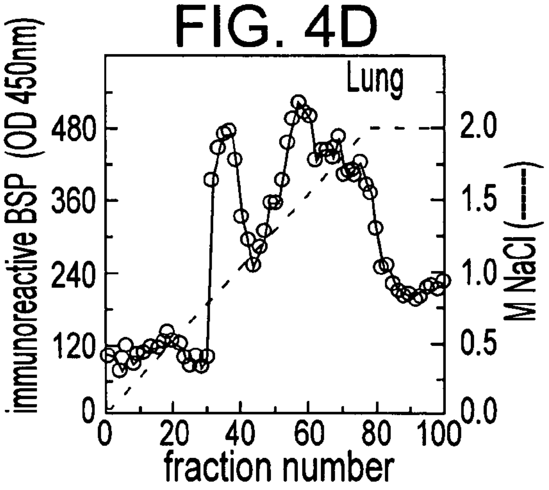
Figure 4E:
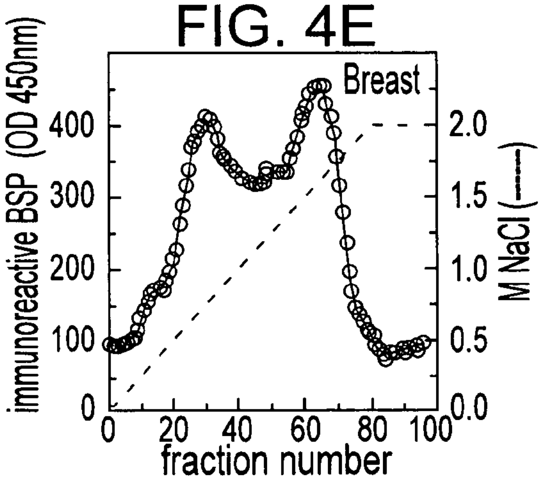
Figure 4F:
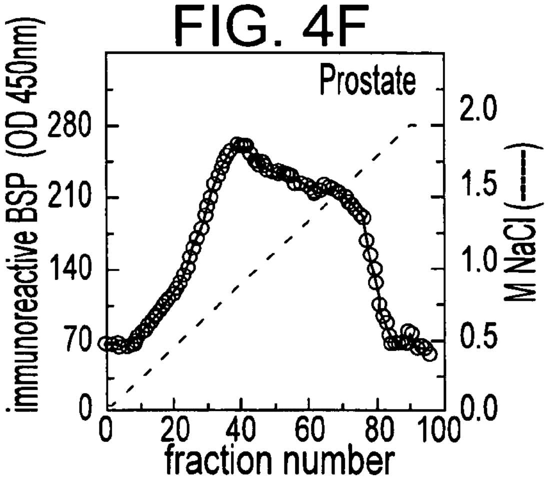

FIGS. 4A–F are graphs which show profiles of serum samples generated by separating the two sub-populations of BSP on a Toyopearl QAE column. FIGS. 4A and B show two normal sera, FIG. 4C shows the profile from a subject known to have a thyroid tumor. FIG. 4D shows the profile from a subject known to have a lung tumor. FIG. 4E shows the profile from a subject known have a breast tumor, and FIG. 4F shows the profile from a subject known to have a prostate tumor.

FIGS. 5A–E: show profiles from 5 different subjects that were known to have breast cancer.

Figure 6:
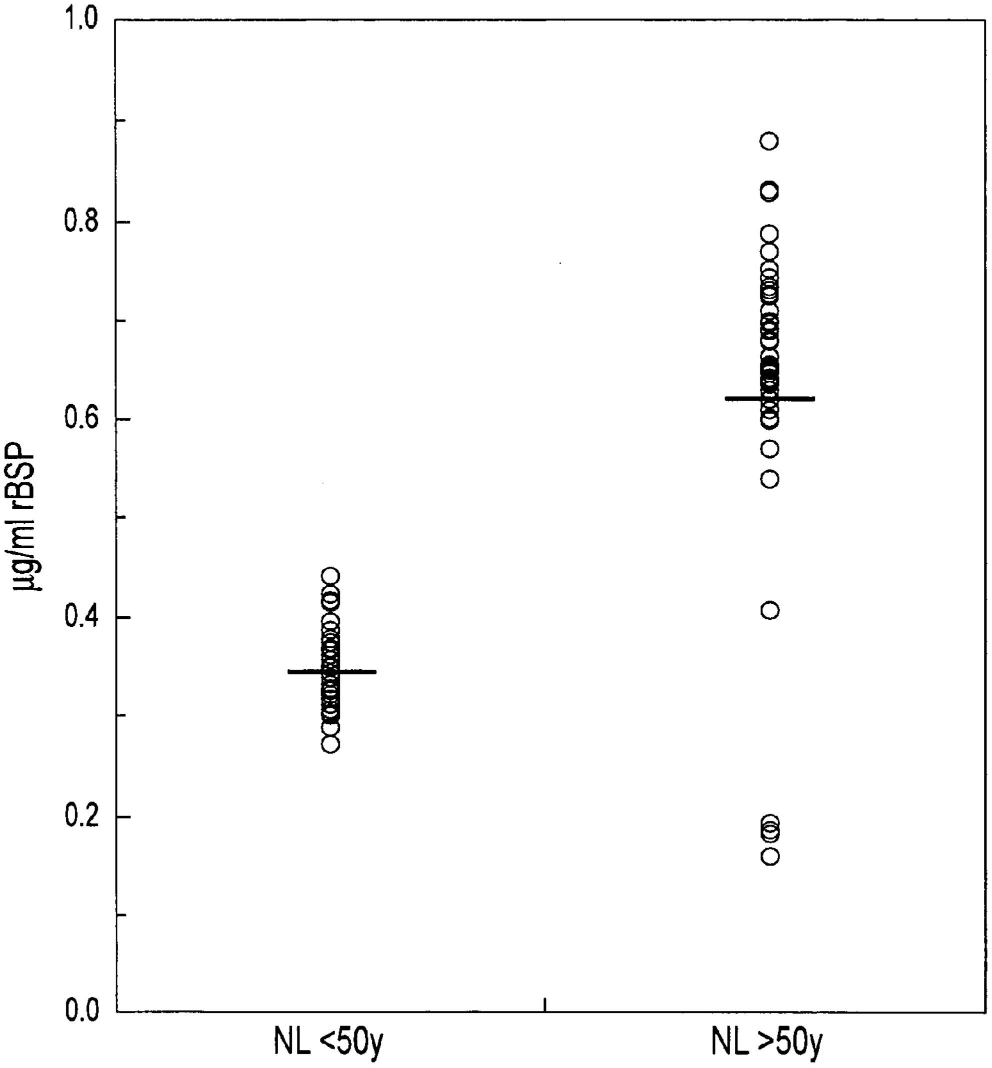

FIG. 6 shows the level of serum BSP detected in samples taken from 32 individuals under the age of 50, and the serum BSP levels from 36 individuals over the age of 50.

Figure 7:
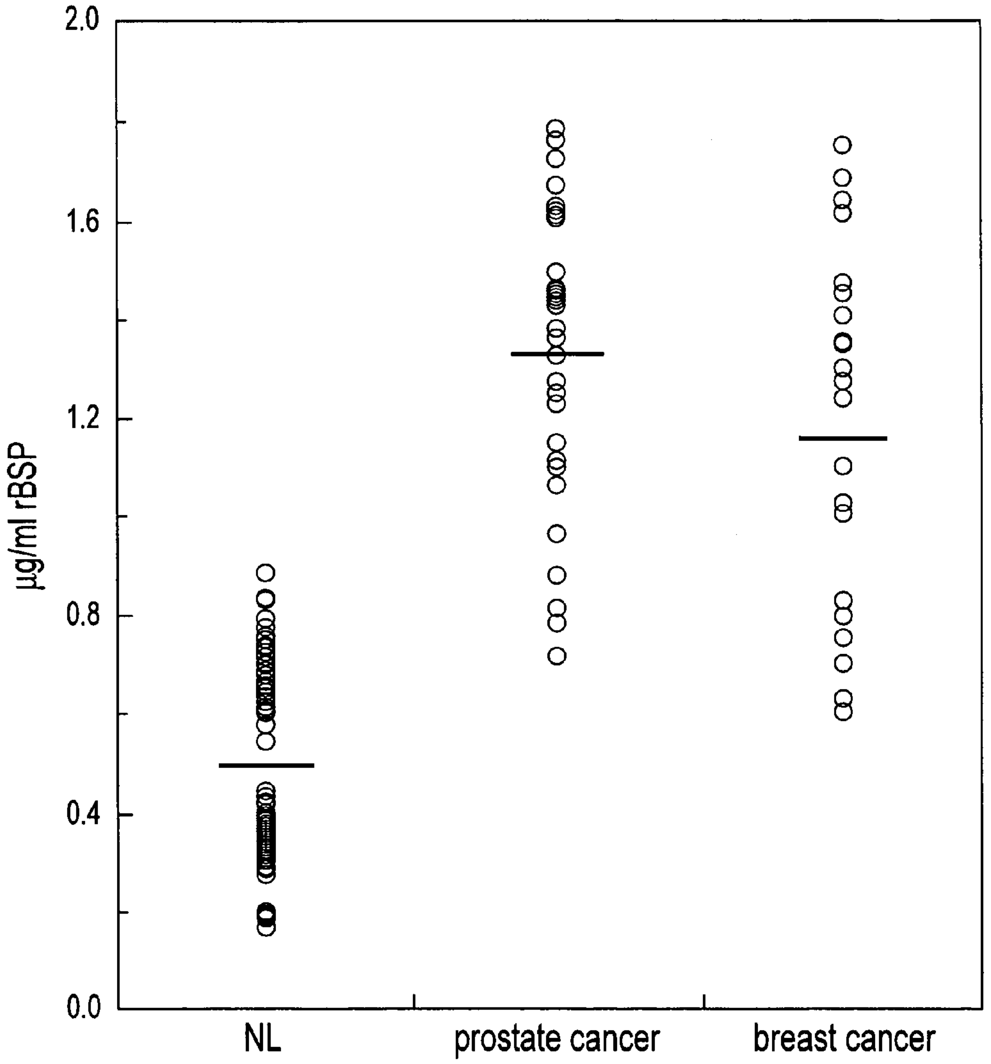

FIG. 7 shows the level of serum BSP detected in samples taken from normal subjects, subjects known to have prostate cancer, and subjects known to have breast cancer.

Figure 8A:
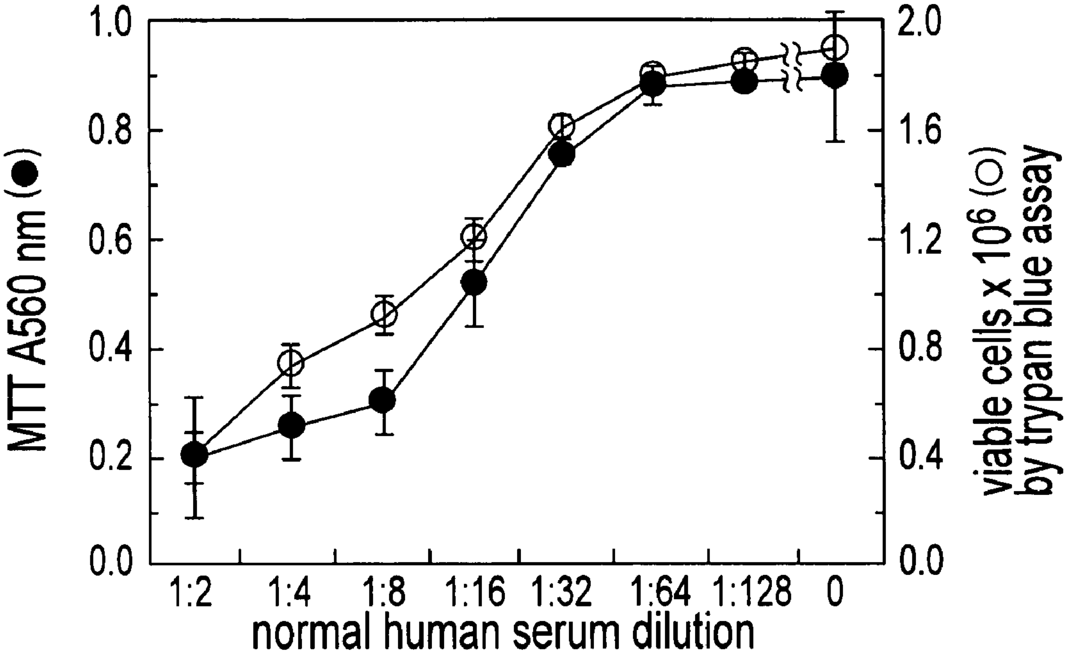
Figure 8B:
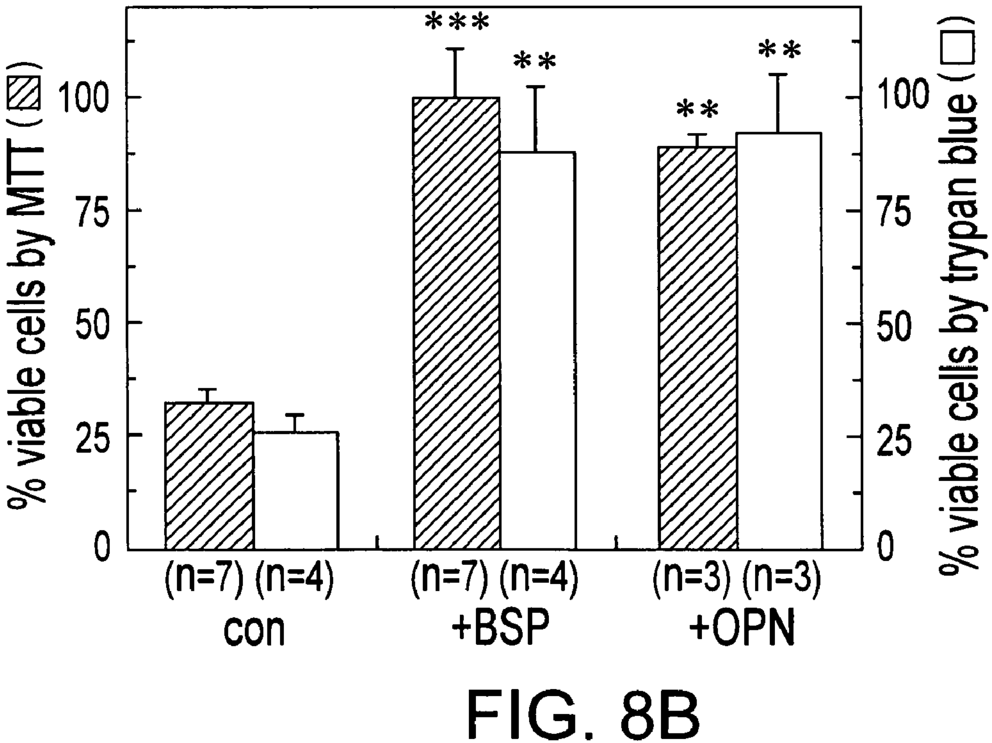

FIGS. 8A and 8B are graphs which show that recombinantly produced BSP and OPN protect MEL cells from complement mediated lysis. MEL cells were rinsed three times with GVB-MgEGTA buffer, resuspended in GVB-MgEGTA at a density of $5\times10^6$ cells/mL, and incubated at 37° C. with different concentrations of normal human serum. After 2 hrs, cells were harvested for trypan blue exclusion assay. The thiazolium blue assay was carried out at identical serum dilutions and cell viability was determined by absorbance at 560 nm. Each data point represents the average of three measurements. The error bars represent the standard deviation of the mean (A). MEL cells in GVB-MgEGTA buffer were incubated with 10 μg/mL of either rBSP or rOPN for 10 minutes at 37° C. Normal human serum was then added at a dilution of 1:10 and the cells were returned to 37° C., incubated for 2 hours and cell viability was determined by trypan blue and thiazolyl blue (MTT) reduction assays (B). Data from 3–7 separate experiments, with treatment replicates in triplicate, was combined to yield mean values. Error bars represent the standard error of the mean. N=number of experiments combined.

Figure 9A:
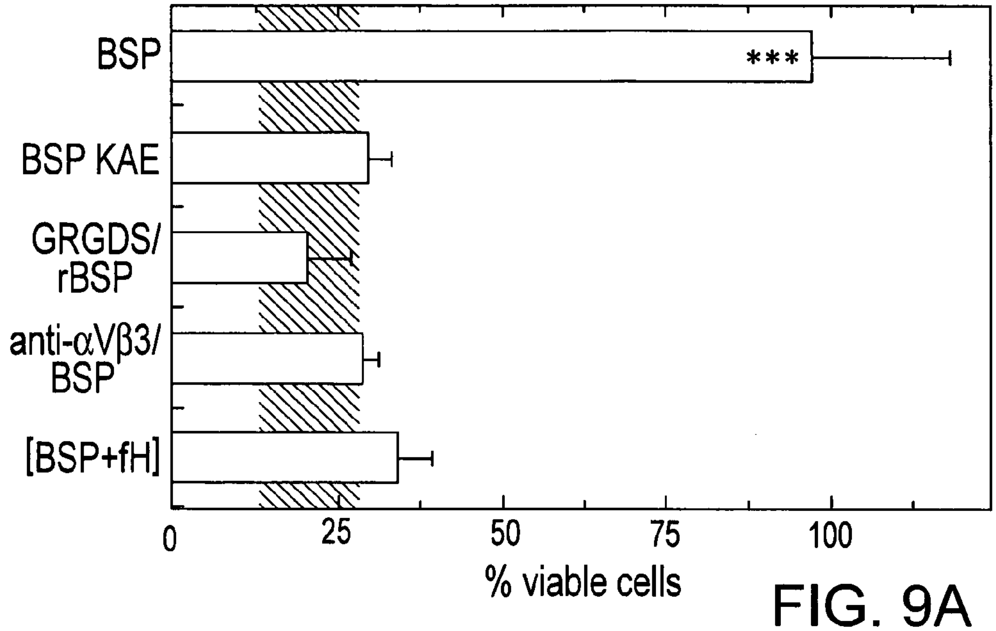

FIG. 9 is a bar graph which shows the involvement of integrin and CD44 in protection from complement mediated lysis. MEL cells prepared as in FIG. 8 were treated with normal rBSP (10 μg/mL), rBSP whose RGD sequence had been mutated to KAE (10 g/mL), and either GRGDS (SEQ ID NO: 10) peptide (400 μM) followed by rBSP or an αVβ3 antibody (1:4000) followed by rBSP for 10 minutes prior to the addition of normal human serum. The cells were then incubated for 10 minutes after which cell viability determined using the MTT assay (A). A cohort of MEL cells were pretreated with rOPN (10 μg/mL) alone, GRGDS (SEQ ID NO: 10) peptide followed by rOPN, the αVβ3 antibody followed by rOPN, or an anti-CD44 antibody (Chemicon, Co.) followed by rOPN, or hyaluronan (HA) followed by rOPN (B). Cells were then treated with normal human serum and viability assayed as in FIG. 8. Treatment of MEL cells with a pre-formed complex of either BSP-Factor H ([BSP+fH]) or OPN-Factor H ([OPN+fH]) abolished the protection from 23 complement-mediated lysis. The data represents the mean and standard error of the mean for three separate experiments. Statistical significance was determined by analysis of variance. Percent cell viability was determined using A560 absorbance values of various conditions and a control where no serum had been added (100% viable). The cross-hatched region represents that range of values observed when normal human serum (1:10) alone was added (maximal cell death).

Figure 10A:
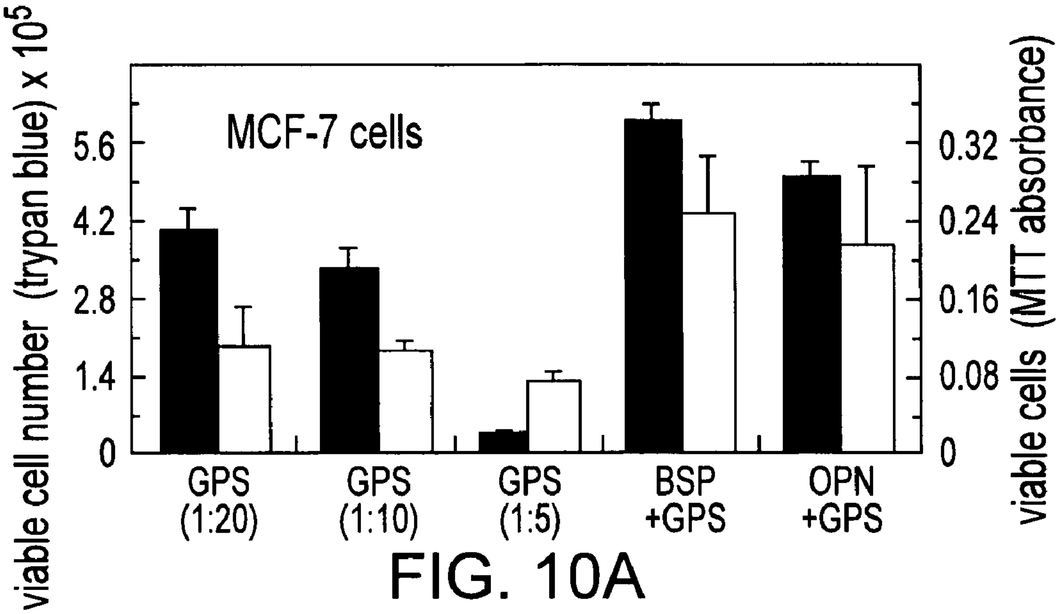
Figure 10B:
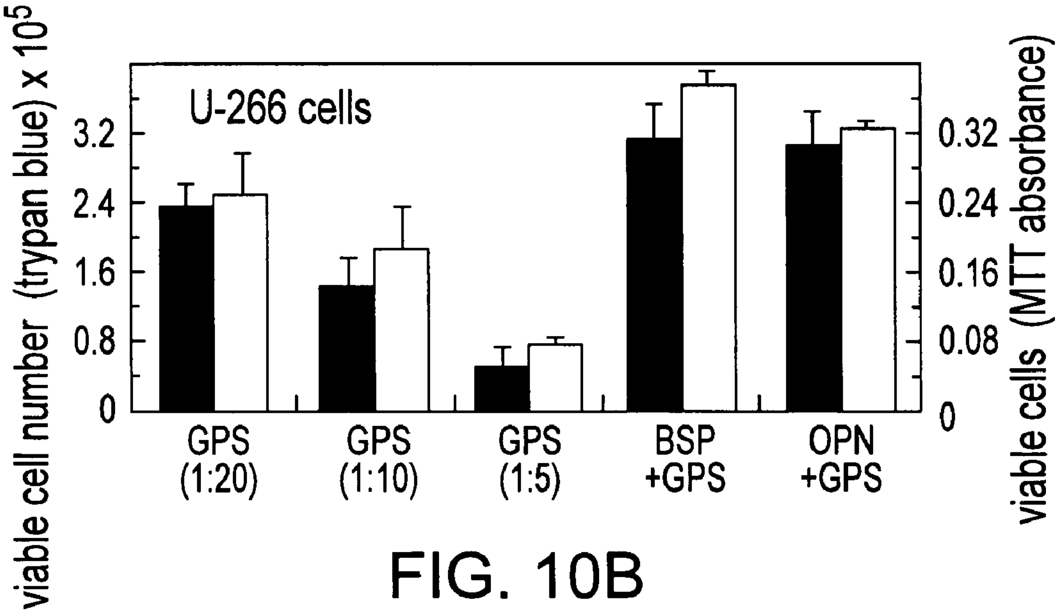

FIGS. 10A and 10B are bar graphs which show that human cancer cell lines can be protected from complement mediated lysis through the addition of SIBLINGS proteins. Human cancer cell lines, MCF-7 (A) and U-266 (B) cells were rinsed three time with GVB-MgEGTA buffer and subsequently treated exactly as in the MEL cell complement-mediated cell lysis assay described above except complement active guinea pig serum (GPS) was substituted for human serum. Three different dilutions of GPS were assayed. For cultures pretreated with 10 μg/mL BSP or OPN, the dilution of GPS used was 1:5. Cell viability was determined by both trypan blue exclusion (solid bar) and MTT (open bar) assay. The bars represent the mean values of triplicate samples and the error bars are the standard deviation values.

Figure 11A:
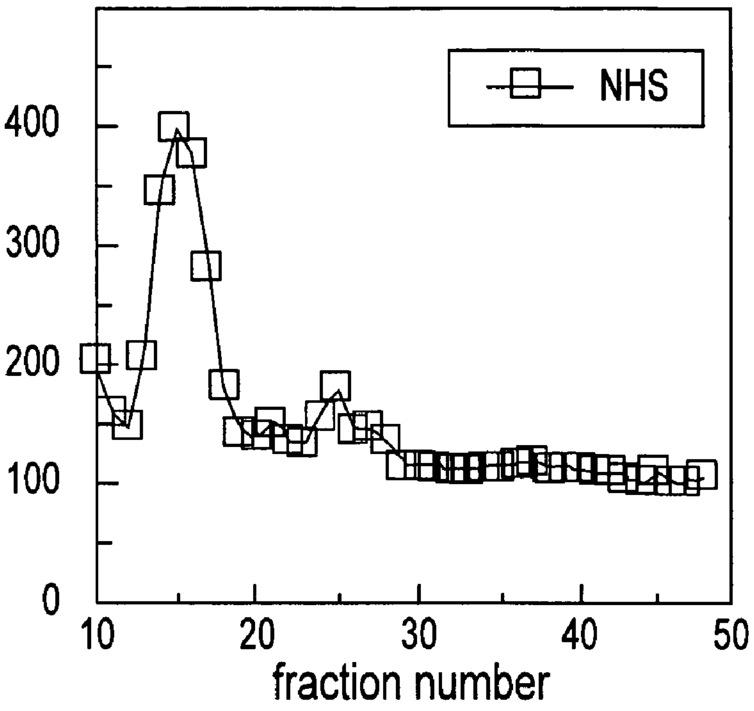
Figure 11B:
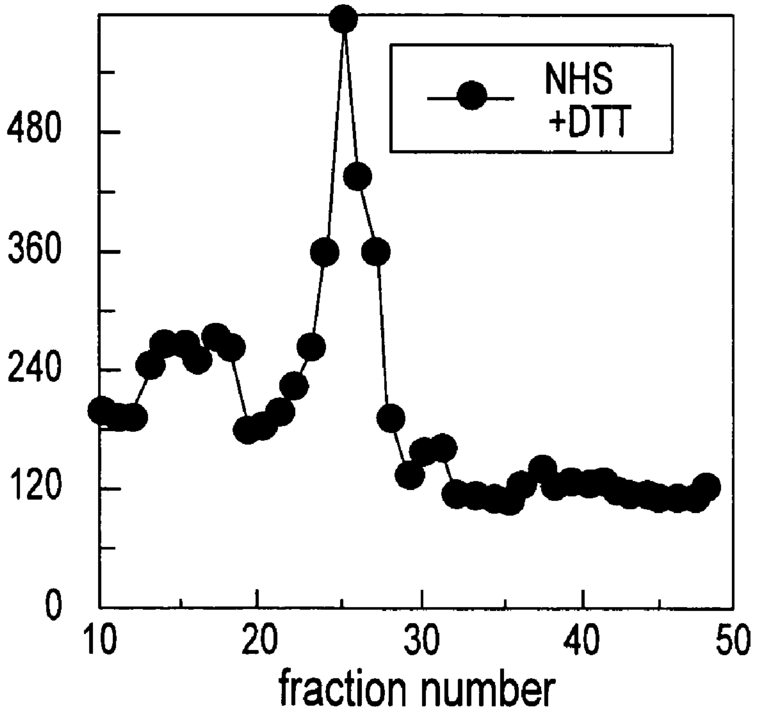

FIGS. 11A and 11B are bar graphs which show the separation of DMP1 from Factor H on a molecular sieve column after treatment with formamide, DTT, and heat, as detected by DMP1 specific polyclonal antisera. FIG. 11A shows normal human serum (NHS) and FIG. 11B shows NHS that has been treated.

SEQUENCE LISTINGS

The nucleic and amino acid sequences listed in the accompanying sequence listing are shown using standard letter abbreviations for nucleotide bases, and three letter code for amino acids. Only one strand of each nucleic acid sequence is shown, but the complementary strand is understood as included by any reference to the displayed strand.

SEQ ID NO: 1: shows the amino acid sequence of human BSP.

SEQ ID NOS: 2–7: show various amino acid sequences which have been used as immunogens for the creation of BSP specific antibodies.

SEQ ID NO: 8: shows a cDNA sequence encoding human BSP.

SEQ ID NO: 9: shows an amino acid sequence that was used as an immunogen for the creation of BSP specific antibodies.

SEQ ID NO: 10: shows the amino acid sequence of a peptide that was used to compete with proteins from the SIBLINGS family of proteins for integrin type binding.

SEQ ID NO: 11: shows the nucleic acid sequence of an OPN encoding sequence (Accesion No. J04765).

SEQ ID NO: 12: shows the amino acid sequence derived from the sequence shown SEQ ID NO:11.

SEQ ID NO: 13: shows the nucleic acid sequence of an OPN encoding sequence (Accesion No. X13694).

SEQ ID NO: 14: shows the amino acid sequence derived from the sequence shown SEQ ID NO:13.

SEQ ID NO: 15: shows the nucleic acid sequence of a DMP1 encoding sequence (Accession No. NM_004407).

SEQ ID NO: 16: shows the amino acid sequence derived from the sequence shown in SEQ ID NO: 15.

SEQ ID NO: 17: shows the nucleic acid sequence of a DSPP encoding sequence (Accession No. AF163151).

SEQ ID NO: 18: shows the amino acid sequence derived from the sequence shown in SEQ ID NO: 17.

DETAILED DESCRIPTION

I. Abbreviations and Definitions

Abnormal: Deviation from normal characteristics. Normal characteristics can be found in a control, a standard for a population, etc. For instance, where the abnormal condition is a disease condition, such as a tumor, a few appropriate sources of normal characteristics might include an individual who is not suffering from the disease (e.g., breast cancer), a population standard of individuals believed not to be suffering from the disease, etc.

Likewise, abnormal may refer to a condition that is associated with a disease. The term "associated with" includes an increased risk of developing the disease as well as the disease itself. For instance, a certain abnormality (such as an increase in the expression of one or more SIBLINGS proteins) can be described as being associated with the biological condition of breast cancer; thus, the abnormality is predictive both of an increased risk of developing breast cancer and of the presence of breast cancer.

Abnormal protein expression, such as abnormal SIBLINGS protein expression, refers to expression of a protein that is in some manner different from expression of the protein in a normal (wildtype) situation. This includes but is not necessarily limited to: (1) a mutation in the protein such that one or more of the amino acid residues is different; (2) a short deletion or addition of one or a few amino acid residues to the sequence of the protein; (3) a longer deletion or addition of amino acid residues, such that an entire protein domain or sub-domain is removed or added; (4) expression of an increased amount of the protein, compared to a control or standard amount; (5) expression of an decreased amount of the protein, compared to a control or standard amount; (6) alteration of the subcellular localization or targeting of the protein; (7) alteration of the temporally regulated expression of the protein (such that the protein is expressed when it normally would not be, or alternatively is not expressed when it normally would be); (8) alteration in post translational processing; and (9) alteration of the localized (e.g., organ or tissue specific) expression of the protein (such that the protein is not expressed where it would normally be expressed or is expressed where it normally would not be expressed), each compared to a control or standard.

Controls or standards appropriate for comparison to a sample, for the determination of abnormality, include samples believed to be normal as well as laboratory values, even though possibly arbitrarily set, keeping in mind that such values may vary from laboratory to laboratory. Laboratory standards and values may be set based on a known or determined population value and may be supplied in the format of a graph or table that permits easy comparison of measured, experimentally determined values.

Implant

A non-self object that is placed in contact with a subject. For example, the object can be an artificial limb, an intraosseous, or intravascular implant or a dental prosthesis. Such objects can comprise molecules that are generated through biosynthetic pathways, such as hydroxyapatite, or collagen, or the object can contain molecules that are generated through non-biosynthetic means, such as metal alloys or plastics. Furthermore, such objects can contain a mixture of molecules such that some of the molecules are biosynthetically generated and some of the molecules are generated through non-biosynthetic means.

Small Integrin-Binding Ligand, N-Linked Glycoproteins (SIBLINGS): The family of secreted phophoproteins that includes, for example, bone sailoprotein (BSP), osteopontin (OSP), dentin matrix protein (DMP1), and dentin sialophosphoprotein (DSPP). It is also likely that other member of the SIBLINGS family of proteins will be identified in the future, and that these additional members of the SIBLINGS family will also bind to Factor H. Hence, when the term SIBLINGS protein is used it refers to not only to the four family members described above, but also to additional family members that will be identified in the future.

The genes encoding the four members of the SIBLINGS family are located on human chromosome 4. Members of the SIBLINGS family of protein are shown, infra, to be capable of binding Factor H. The SIBLINGS/Factor H complex can cause the SIBLINGS protein to be nearly undetectable unless the complex is first disrupted. Hence, the discovery that members of the SIBLINGS family of proteins binds to Factor H allows for more accurate and sensitive quantification of the concentration of SIBLINGS proteins. The discovery that SIBLINGS proteins bind Factor H has also led to the development of methods of using SIBLINGS proteins to selectively protect cells from complement mediated lysis.

Biologically Active SIBLINGS Proteins: Biologically active SIBLINGS proteins are characterized by their ability to protect cells from complement mediated lysis. This activity can be readily assessed using the MEL cell assay described below. These proteins can be "derived" from SIBLINGS proteins such that the endogenous SIBLINGS protein's amino acid sequence is altered to contain amino acid substitutions, deletions and/or additions. If, however, the endogenous SIBLINGS protein sequence is altered it will continue to display its ability to inhibit complement-mediated lysis and the derived SIBLINGS protein sequence will be additionally characterized by having at least 50%, 60%, 70%, 80%, or 90% sequence identity to the endogenous sequence.

As mentioned above, the inhibition of complement-mediated lysis can be detected using the MEL cell based assay described below. A SIBLINGS protein will be found to be "biologically active" if when tested in the MEL assay it confers protection to cells compared to a control sample that does not contain the SIBLINGS protein.

BSP

The normal endogenous population of bone sialoprotein. This population contains a wide range of BSP proteins, some that are not extensively post-translationally modified, as well as some of which are extensively post-translationally modified. Furthermore, this normal population contains within it at least two distinct sub-populations. The first sub-population is relatively non-acidic, and it is the sub-population that is most prominent in the serum of normal subjects (subjects without tumors). The second sub-population of BSP is relatively acidic and found in subjects with tumors, for example in subjects with breast, lung, prostate, and thyroid tumors.

Relatively Acidic BSP

The term relatively acidic BSP refers to a sub-population of BSP found primarily in the serum of subjects who have various types of tumors. There are multiple methods that can be used to detect the presence of this sub-population in a subject. These methods include column chromatography methods and electrophoresis. Therefore, for clarity the relatively acidic BSP is defined through its behavior on the specific ion exchange column assay described in section IV, below. Briefly, this section details the use of a Toyopearl QAE column for the separation of the relatively non-acidic BSP from the relatively acidic BSP. Characterized in this way, and using the assay provided, the relatively acidic BSP will elute from the column at a salt concentration of greater than 0.5 M NaCl.

While not wishing to be bound to a particular theory, it is believed that the relatively acidic BSP is post-translationally modified to contain sialic acids, phosphate, and/or sulfate. In that case, the relative concentration of each sub-population of phosphorylated or sulfated BSP can be determined by assays that quantify the concentration of sulfur and/or phosphate.

Specific Binding Agent

An agent that binds substantially only to a defined target. Thus, a SIBLINGS protein specific binding agent binds substantially only a particular SIBLINGS protein. For example, the term "BSP specific binding agent" includes anti-BSP and other agents that bind substantially only to BSP. Similarly, the term "relatively acidic BSP specific binding agent" includes antibodies that are specific for the relatively acidic BSP and other agents that bind substantially only to the relatively acidic BSP. The term "relatively non-acidic BSP specific binding agent" includes antibodies that are specific for the relatively acidic BSP and other agents that bind substantially only to the relatively non-acidic BSP. The term "exposed portion of SIBLINGS protein specific binding agent" includes antibodies and other agents that are specific for the exposed portion of a SIBLINGS protein when it is complexed with Factor H.

The discussion below specifically mentions anti-BSP antibodies, however it also applies to anti-relatively acidic BSP antibodies, anti-relatively non-acidic BSP antibodies, as well as anti-exposed portion of SIBLINGS protein antibodies.

The term anti-SIBLINGS protein antibodies encompasses monoclonal and polyclonal antibodies that are specific for SIBLINGS proteins, i.e. which bind substantially only to BSP when assessed using the methods described below, as well as immunologically effective portions (fragments) thereof. Preferably, the anti-SIBLINGS protein antibodies used in the present invention are monoclonal antibodies (or immunologically effective portions thereof) and may also be humanized monoclonal antibodies (or immunologically effective portions thereof). Immunologically effective portions of monoclonal antibodies include Fab, Fab', $F(ab')_2$ Fabc and Fv portions (for a review, see Better and Horowitz, *Methods Enzymol.* 178:476–496, 1989). Anti-BSP antibodies may also be produced using standard procedures described in a number of texts, including Antibodies, A Laboratory Manual by Harlow and Lane, Cold Spring Harbor Laboratory (1988).

The determination that a particular agent binds substantially only to the desired immunogen may readily be made by using or adapting routine procedures. One suitable in vitro assay makes use of the Western blotting procedure (described in many standard texts, including Antibodies, A Laboratory Manual by Harlow and Lane, Cold Spring Harbor Laboratory, 1988). Western blotting may be used to determine that a given specific binding agent, such as an anti-SIBLINGS protein monoclonal antibody, binds substantially only to a SIBLINGS protein, as described in Fisher et al., *JBC,* 262:9702–08, 1987.

Vector

A nucleic acid molecule as introduced into a host cell, thereby producing a transformed host cell. A vector may include nucleic acid sequences that permit it to replicate in the host cell, such as an origin of replication. A vector may also include one or more selectable marker genes and other genetic elements known in the art.

Transformed

A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Sample

The term sample includes any artificially generated or biological specimen that is of interest and is being tested for the presence of SIBLINGS proteins. More specifically, the term biological specimen includes any specimen that was generated by a living cell. Therefore, samples derived from cells in a tissue culture setting, including the cells themselves fall within the definition or biological specimen. Furthermore, samples taken from a subject, such as tissue samples and bodily fluids (such a blood plasma or serum) also fall within the definition of biological specimen.

Tumor

Tumors are abnormal growths which can be either malignant or benign, solid or liquid (for example, hematogenous). This term particularly includes malignant tumors which can be either solid (such as a breast or prostate carcinoma) or non-solid (such as a leukemia). Tumors can also be further divided into subtypes, such as adenocarcinomas (e.g. of the breast, prostate or lung).

Metastasis

A tumor implant discontinuous with a primary tumor. Any cancer may metastasize to bone, but metastases from carcinomas are the most common. There is a subset of carcinomas that is clinically recognized as more likely to metastasize to bone, and this subset includes carcinomas of the breast, lung, prostate, kidney and thyroid. Even if a tumor is not presently recognized as being particularly likely to metastasize to bone, it can be so categorized by a diagnosis in a particular subject that a skeletal metastasis has occurred (for example by scintigram and biopsy), or by studies of populations of subjects presenting with a particular histological sub-type of cancer.

Isolated

An isolated biological component (such as a nucleic acid or protein) has been substantially separated or purified away from other biological components in the biological specimen in which the component naturally occurs, i.e., other chromosomal and extrachromosomal DNA and RNA, and proteins. Nucleic acids and proteins which have been isolated thus include nucleic acids and proteins purified by standard purification methods. The term also embraces nucleic acids and proteins prepared by recombinant expression in a host cell as well as chemically synthesized nucleic acids and proteins.

Purified

The term purified does not require absolute purity; rather, it is intended as a relative term. Thus, for example, a purified BSP protein preparation is one in which the BSP is more enriched than the protein is in its natural environment. That environment being either in serum or within a cell. Preferably, a preparation of BSP is purified such that BSP represents at least 50% of the total protein content of the preparation.

Operably Linked

A first nucleic acid sequence is operably linked with a second nucleic acid sequence when the first nucleic acid sequence is placed in a functional relationship with the second nucleic acid sequence. For instance, a promoter is operably linked to a coding sequence, if the promoter affects the transcription or expression of the coding sequence. Generally, operably linked DNA sequences are contiguous and, where necessary to join two protein coding regions, in the same reading frame.

Recombinant

A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Subject

This term includes both human and non-human mammals. Similarly, the term subject includes both human and veterinary subjects.

Sequence Identity

The term "sequence identity" is used to describe the similarity between two nucleic acid sequences or between two amino acid sequences. Sequence identity is typically expressed in terms of percentage identity; the higher the percentage, the more similar the two sequences.

Methods for aligning sequences for comparison purposes are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444–2448, 1988; Higgins and Sharp, *Gene* 73:237–244, 1988; Higgins and Sharp, *CABIOS* 5:151–153, 1989; Corpet et al., *Nucleic Acids Research* 16:10881–10890, 1988; Huang et al., *Computer Applications in the Biosciences* 8:155–165, 1992; and Pearson et al., *Methods in Molecular Biology* 24:307–331, 1994; Altschul et al., *J. Mol. Biol.* 215:403–410, 1990, presents a detailed consideration of sequence alignment methods and homology calculations.

The NCBI Basic Local Alignment Search Tool (BLAST™, Altschul et al., *J. Mol. Biol.* 215:403–410, 1990) is available from several sources, including the National Center for Biotechnology Information (NCBI, Bethesda, Md.) and on the Internet, for use in connection with the sequence-analysis programs blastp, blastn, blastx, tblastn and tblastx.

For comparisons of amino acid sequences of greater than about 30 amino acids, the "Blast 2 sequences" function in the BLAST™ program is employed using the default BLOSUM62 matrix set to default parameters, (gap existence cost of 11, and a per-residue gap cost of 1). When aligning short peptides (fewer than about 30 amino acids), the alignment should be performed using the Blast 2 sequences function, employing the PAM30 matrix set to default parameters (open gap 9, extension gap 1 penalties). Proteins having even greater similarity to the reference sequences will show increasing percentage identities when assessed by this method, such as at least 45%, at least 50%, at least 60%, at least 70%, at least 75%, at least 80%, at least 85%, at least 90%, or at least 95% sequence identity.

A first nucleic acid is "substantially similar" to a second nucleic acid if, when optimally aligned (with appropriate nucleotide insertions or deletions) with the other nucleic acid (or its complementary strand), nucleotide sequence identity occurs in at least about 60%, 75%, 80%, 85%, 90% or 95% of the nucleotide bases. (As used herein, "optimally aligned" sequences exhibit a maximal possible sequence identity). Sequence similarity can be determined by comparing the nucleotide sequences of two nucleic acids using the BLAST™ sequence analysis software (blastn) available from The National Center for Biotechnology Information. Such comparisons may be made using the software set to default settings (expect=10, filter=default, descriptions=500 pairwise, alignments=500, alignment view=standard, gap existence cost=11, per residue existence=1, per residue gap cost=0.85). Similarly, a first polypeptide is substantially similar to a second polypeptide if it shows sequence identity of at least about 75%–90% or greater when optimally aligned and compared using BLAST™ software (blastp) using default settings.

Conservative Amino Acid Substitutions

Conservative amino acid substitutions usually have minimal impact on the activity of the resultant protein. Such substitutions are described below.

Conservative substitutions replace one amino acid with another amino acid that is similar in size, hydrophobicity, etc. Such substitutions generally are conservative when it is desired to finely modulate the characteristics of the protein. Examples of amino acids which may be substituted for an original amino acid in a protein and which are regarded as conservative substitutions include: Ser for Ala; Lys for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

More substantial changes in enzymatic function or other features may be obtained by selecting substitutions that are less conservative than those above, i.e., selecting residues that differ more significantly in their effect on maintaining: (a) the structure of the polypeptide backbone in the area of the substitution, for example, as a sheet or helical conformation, (b) the charge or hydrophobicity of the molecule at the target site, or (c) the bulk of the side chain. Substitutions that generally produce the greatest changes in protein properties are those in which: (a) a hydrophilic residue, e.g., seryl or threonyl, is substituted for (or by) a hydrophobic residue, e.g., leucyl, isoleucyl, phenylalanyl, valyl, or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine. The effects of these amino acid substitutions or deletions or additions may be assessed for SIBLINGS protein derivatives by analyzing the ability of the respective modified polypeptide to inhibit complement-mediated cell lysis.

Variant SIBLINGS protein encoding cDNAs or genes may be produced by standard DNA mutagenesis techniques, for example, M13 primer mutagenesis. Details of these techniques are provided in Sambrook et al. (ed.), *Molecular Cloning: A Laboratory Manual,* 2nd ed., vol. 1–3, Ch. 15, Cold Spring Harbor Laboratory Press, Cold Spring Harbor, N.Y., 1989, and Ausubel et al. (ed.) *Current Protocols in Molecular Biology*, Greene Publishing and Wiley-Interscience, New York (with periodic updates), 1987. By the use of such techniques, variants may be created that differ slightly from the endogenous SIBLINGS protein encoding cDNA or gene sequences, yet that still encode a biologically active SIBLINGS protein. DNA molecules and nucleotide sequences that are derivatives of those specifically disclosed herein and that differ from those disclosed by the deletion, addition, or substitution of nucleotides while still encoding a biologically active SIBLINGS protein are comprehended by this invention. In their simplest form, such variants may differ from the disclosed sequences by alteration of the coding region to fit the codon usage bias of the particular organism into which the molecule is to be introduced.

Additionally, as mentioned above new members of the SIBLINGS family of proteins can be identified by searching various DNA databases, such as the database maintained at the National Center for Biotechnoloy Information in Bethesda, Md. Searches can be done such that sequences that are conserved between existing members of the SIBLINGS family of proteins are used to identify other members of the family. Once identified these members can be used to the assays described below to determine if they maintain SIBLINGS protein biological activity.

Throughout the specification and claims, reference to the singular (such as "a" or "the") includes the plural, unless clearly indicated otherwise by context.

II. Identification and Characterization of SIBLINGS/Factor H Complex

Initial experimentation, which is described below, led to the identification of a BSP/Factor H complex. The population of BSP in serum from subjects displaying tumors was additionally found to contain a sub-population of relatively acidic BSP. Subsequent experimentation showed that both OPN and DMP1 bound to Factor H and it is likely that the detection of these SIBLINGS proteins, as well as other members of the protein family, will be enhanced by disrupting the SIBLINGS/Factor H complex prior to quantifying protein levels.

A. Identification and Characterization of the BSP/Factor H Complex

BSP is an acidic protein, containing not only many acidic amino acids particularly glutamic acid) but also phosphate, sulfated tyrosines and oligosaccharides, as well as many sialic acid groups. As such it should bind to an anion exchange column under conditions of low salt (<0.1 M NaCl) and neutral pH (6–8). This is indeed the case, and BSP from bone extracts and from culture medium has been found to elute off of a DEAE column at about 0.4 M NaCl in 7 M urea at pH 6.

Surprisingly, serum BSP failed to behave in the same manner as BSP from bone extracts and cell culture medium as described above. In fact, injecting normal human serum onto a DEAE or QAE HPLC column resulted in all of the detectable BSP eluting in the unbound fraction, therefore it behaved as a neutral or positively charged protein. This indicated that the BSP was bound to something that masked its many negative charges, hence attempts were made to disrupt the complex. These attempts involved using denaturants, such as 50% formamide or 8 M urea, reducing agents such as 1 mM DTT or 10 mM β-mercaptoethanol, and heating to 100° C. for 5 minutes. None of these approaches was independently successful in disrupting the complex, as indicated by the failure of the BSP to bind to an anion exchange columm.

However, a combination of a denaturant, a reducing agent and heating finally did separate the BSP from the complex. This separation was noted by the increased binding of the BSP to an anion exchange column with subsequent elution in a salt gradient and detection with polyclonal antisera. The anti-sera used was raised in rabbit against human BSP or fragments thereof, and termed LF-6, LF-83, LF-84, LF-100, LF-101, LF-119, LF-120, and LF-125 (see Table 2), which were tested for specificity via either ELISA assay or Western blotting. (Acta Orthop. Scand, (Suppl. 266) 66:61–65, 1995. The LF-142 (Table 2) polyclonal antisera was raised in rabbit against a synthetic BSP peptide which contained several sulfated tyrosines.

The previously uncharacterized protein described above, that was found to mask the otherwise acidic BSP, was subsequently identified as being Factor H. The identity of the protein was determined by several different assay techniques, and these techniques, as well as the results are described below.

1) Factor H specific monoclonal antibodies were obtained from Quidel, San Diego, Calif., USA. These antibodies were used to precipitate Factor H from human sera. One sample was left untreated while another was heated to 100° C. for 5 minutes in the presence of 1 mM DTT and 50% formamide. These samples were then separated on a SDS gel and subjected to western blotting analysis using a BSP specific antibody LF-100. Results from the Western blot analysis showed a high molecular weight band (Mr ~200,000 Da) in the lane without DTT, and the more typical BSP size of 75,000 Da in the lane treated with DTT and formamide.

Furthermore, a similar high molecular weight band was also seen when a Western blot was performed using as a sample purified human Factor H (Quidel) complexed with BSP. This artificially created complex was immunoprecipitated by the same Factor H antisera (see above), and analyzed with the same results as with the whole human serum described above. This showed that BSP was bound to Factor H.

Figure 1A:
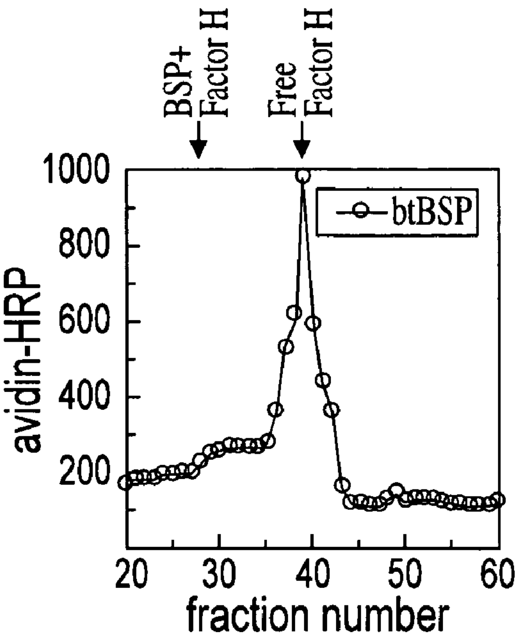
FIGS. 1A–C are graphs which show the binding of BSP to Factor H as detected with HP-conjugated avidin after separation on a molecular sieve column.
Figure 1B:
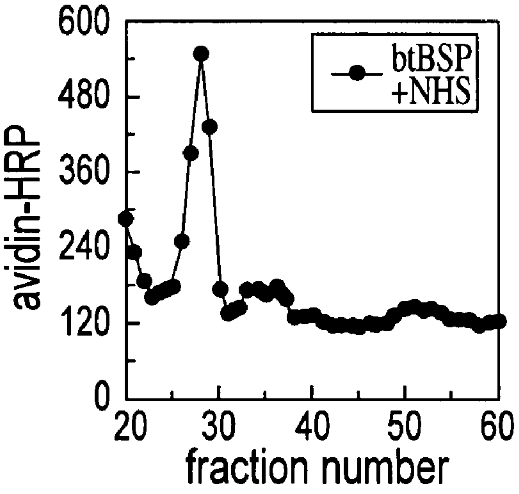
Figure 1C:
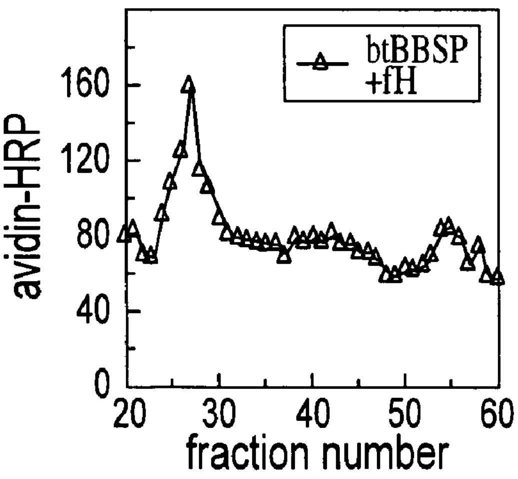

2) Biotinylated human BSP was added to normal human serum and the material was chromatographed on a calibrated molecular sieve column (Superose 6, Pharmacia, FIG. 1B). A separate chromatogram with the biotinylated BSP alone was also generated. The biotinylated products were subsequently detected using HRP-conjugated avidin on a 96-well direct ELISA (FIG. 1A). The BSP alone chromatographed to the expected approximate 75,000 Da position, while the BSP added to the human serum chromatographed to a position consistent with being complexed to Factor H (about 200,000 Da, FIG. 1B, detected with HRP-conjugated avidin). Furthermore, no 75,000 Da, (i.e. free) BSP could be detected, suggesting that all was bound to the Factor H (Factor H is found at concentration of about 500 μg/mL human serum). An additional chromatograph was generated with biotinylated BSP added to Factor H (FIG. 1C). This chromatograph showed that the product eluted at the same size at the sample containing biotinylated BSP and normal human serum (FIG. 1B).

Figure 2A:
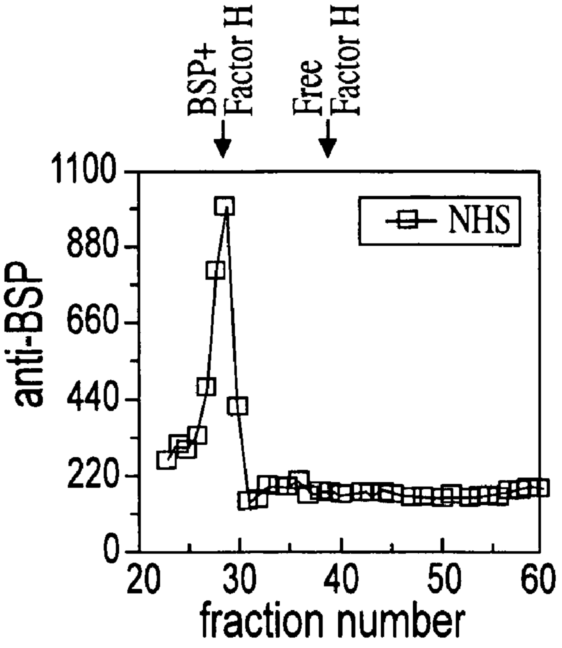
FIGS. 2A–C are graphs which show the separation of BSP from Factor H after treatment with formamide, DTT, and heat, as detected with LF-100 antisera after separation on a molecular sieve column.
Figure 2B:
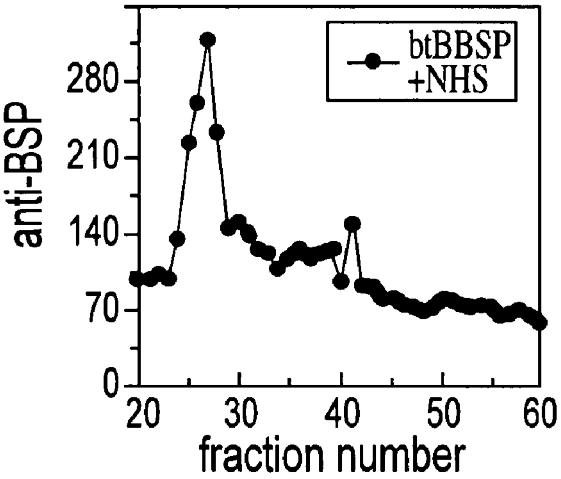
Figure 2C:
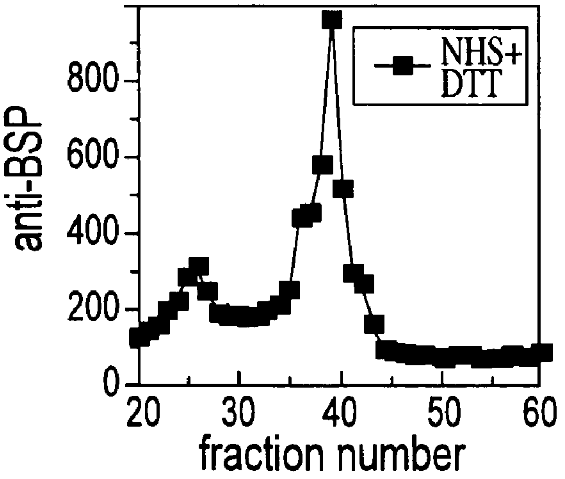

The effect of treatment with DTT and 50% formamide was observed using a molecular sieve column and detecting the products with the polyclonal antibody LF-100. This antibody was previously found to bind to both the bound and unbound form of BSP, however, this binding is probably due to the fact that the SIBLINGS/Factor H complex is at least partially disrupted. Results showed that the BSP from untreated normal human serum eluted at about 200,000 Da (FIG. 2A). Similarly, biotinylated BSP with normal human serum showed a major peak at about 200,000 Da, the expected size of the BSP/Factor H complex, and a second small peak about 75,000 Da (FIG. 2B). Finally, a sample of normal human serum incubated in the presence of 50% formamide and 1 mM DTT at 100° C. for five minutes resulted in a peak corresponding to BSP (FIG. 2C).

3) Biotinylated human BSP bound normally to the anion exchange column. Addition of human serum prior to loading on the anion exchange column caused the biotin activity to elute in the unbound fraction. Pretreating with purified human Factor H gave the same results. These results showed that Factor H could render the BSP unable to bind to the column, a property of the BSP found naturally in human serum.

4) Fluorescence spectroscopic analysis of the tryptophanes of Factor H (BSP does not contain tryptophane) during the binding of BSP shows that the two rapidly form a strong interaction that is stoichiometric (1:1) and saturable (FIGS. 3A and 3B).

B. Characterization of OPN and DMP1/Factor H Binding

The salient structural features of Factor H include 20 short consensus repeats (SCRs) that contain four cysteine residues forming two disulfide bonds per repeat. In addition, each SCR contains one conserved tryptophan residue per repeat and Factor H is known to interact with several sialic acid-containing proteins. Therefore, binding interactions between members of the SIBLINGS family of proteins and Factor H can be studied by steady state fluorescence.

Steady state fluorescence studies were accomplished by titrating purified human complement Factor H with rBSP, rOPN, and rDMP1 followed by excitation at 295 nm and monitoring emission between 300 and 450 nm. The emission profile of Factor H alone yields a peak at 347 nm. The addition of rBSP, rOPN, or rDMP1 in nm increments causes a relative fluorescent intensity quenching. Conversion of the fluorescent intensity titration into a binding curve by determining the fraction of binding sites occupied as the fractional change in fluorescence quenching at 347 nm yields a saturable binding curve. By steady state fluorescence, the binding of BSP, OPN, and DMP1, by Factor H are saturable and possess a 1:1 stoichiometry and the binding constants are in the nM range. Given that normal serum concentration of Factor H is ~0.5 mg/mL it is probable that virtually all BSP, OPN, and DMP1 in serum will be complexed with Factor H.

III. Detection of Elevated Levels of Members of the SIBLINGS Family of Proteins in Serum Recent observations have shown that BSP and OPN are expressed by malignant tissue. BSP is expressed in primary breast cancers (Gillespie et al., *Int. J. Cancer* 73(6):813–815, 1997; Bellahcene et al., *Cancer Res.* 54(11): 2823–2826, 1994; Bellahcene et al., *Int. J. Cancer* 69(4): 350–353, 1996; Seibel et al., J. Clin. Endocrinol Metab. 81(9):3289–3294, 1996), prostate cancer (Waltregny et al., *J. Natl. Cancer Inst.* 90(13):1000–1008, 1998), lung cancer (Bellahcene et al., *Calcif. Tissue Int.* 61(3):183–188, 1997), thyroid cancer (Bellahcene et al., *Thyroid* 8(8):637–641, 1998), malignant bone disease (Chen et al., *Histochem.* 30(1):1–6, 1998), and by neoplastic odonotoblasts (van der Pluijm et al., *Cancer Res.* 56(8): 1948–1955, 1996). In addition, BSP peptides are potent inhibitors of breast cancer cell adhesion to bone (van der Pluijm et al., *Lab Invest.* 77(6):665–675, 1997; Tunio et al., *Arch. Pathol. Lab. Med.* 122(12):1087–1090, 1998). OPN is expressed in breast cancer (Gillespie et al., *Int. J. Cancer.* 73(6):812–815, 1997; Sung et al., *Exp. Cell Res.* 241(2):273–284, 1998; Bellahcene and Castronovo, *Bull. Cancer.* 84(1):17–24, 1997; Tuck et al., *Int. J. Cancer* 79(5):502–508, 1998), as well as in prostate cancer (Koeneman et al., *Prostate* 39(4):246–261, 1999), thyroid cancer (Wright et al., *Int. J. Cancer.* 46(1):39–49, 1990), skin cancer (Senger et al., *CBiochim. Biophys. Acta* 996(1–2):43–48, 1989) and several other types of cancer (Senger et al., *AntiCancer Res.* 56(8): 1948–1955, 1996; Chambers et al., *Anticancer Res.* 12(1):43–47, 1992; Mevoracj et al., *J. Exp. Med.* 188(12): 2313–2320, 2331, 1998). Given that these two SIBLINGS proteins are expressed in cancer tissue it is likely that other members of the family will also be found to be over expressed in tumors. Hence, it is desirable to develop sensitive assays for detecting the presence of SIBLINGS proteins.

As described above, it has been shown the BSP, OPN, and DMP1 bind to Factor H. Hence, it is likely that these members of the SIBLINGS family of proteins as, well as the yet untested DPP1 protein, are bound to Factor H in vivo. Therefore, in order to accurately detect the concentration of these proteins in serum the SIBLINGS/Factor H complex should be disrupted prior to quantifying the SIBLINGS protein level.

Serum levels of BSP have been quantified previously via radioimmunoassays (RIAs). These assays, which involve incubation for a 24 hour period in the presence of antibody, have led to the determination that the circulating levels of BSP in normal subjects are between 5 ng/mL and 24 ng/mL (Karmatschek, *Clinical Chemistry* 43:2076–82, 1997). However, using the experimental procedures detailed below, which exploit the finding that BSP is at least partially undetectable when bound to Factor H, it has been determined that the circulating concentration of BSP in normal subjects may extend across a much broader range, for example between 200 ng/mL serum and 1000 ng/mL serum. Thus, the discovery that BSP is bound to Factor H allows BSP levels to be more accurately determined.

The direct detection of BSP as well as other SIBLNGS proteins in serum is hampered by the fact that it is effectively bound by Factor H and is not expected to be easily detected by most antisera. For example, serum samples where eluted from an ion exchange column, and ELISA assays (described below) were preformed using polyclonal antisera LF-6 and LF-83 (Table 2). These antisera were the same polyclonal antisera that were used by Bellahcene et al., *Cancer Research* 54:823–826, 1994; Bellahcene et al., *Calcif. Tissue Int.* 61:183–188, 1997; Bellahcene et al., *Calcif. Tissue Int.* 61:183–188, 1998a; and Bellahcene et al., *Thyroid* 8:637–641. 1998b, to detect the extopic expression of BSP in various tumor types. However, these antisera, as well as several others failed to detect the BSP/Factor H complex found in serum. Therefore, disrupting the BSP/Factor H complex prior to quantitating serum BSP levels allows for a more accurate assessment of serum BSP concentration.

There are several different methods which could be used to disrupt the SIBLINGS/Factor H complex and detect serum SIBLINGS protein levels. However, the methods used ideally take into account: 1) the properties of the SIBLINGS/Factor H complex compared to the SIBLINGS protein once it is freed from Factor H; 2) the possible problems resulting from denaturing other serum proteins, such as albumin (for example, denatured serum in 50% formamide is acceptable, but if the denaturant present is subsequently removed, the serum forms a gel even if diluted 1:10 in normal saline buffer); and 3) the SIBLINGS protein should also end up in a medium that is suitable for conducting immunoassays after the SIBLINGS/Factor H complex is disrupted.

One particularly useful method of detecting SIBLINGS proteins involves separating the SIBLINGS protein from Factor H, inactivating the contaminants, such as DTT and BME, and then diluting the sample such that the sample is in a media that allows for immunoassay techniques to be used. This assay method is more feasible, in part, because of the considerably higher concentration of SIBLINGS protein that is available after separation form Factor H.

Another example of a method for quantifying serum levels of BSP as well as other SIBLINGS proteins involves: 1) separating the SIBLINGS/Factor H complex from most other serum components, particularly albumin; 2) disrupting the complex (by substantial separation of Factor H from the SIBLINGS protein); and 3) introducing the SIBLINGS protein into buffer conditions compatible with binding to antibodies. The initial separation step involved diluting 50 μl serum with 150 μl PBS. The resulting diluted serum was then placed on a disposable anion exchange column (Toyopearl QAE column available from Taso-Haas, a part of Rhom&Hass, Montgomeryville, Pa.). The albumin present in the serum was then bound to the column and the Factor H-SIBLINGS protein complex passed through. The complex was then separated via incubating at 100° C. in the presence of DTT and formamide. The denaturants and reducing agents were then removed by placing the sample on a sephadex G25 column available from Amersham Pharmacia, Piscataway, N.J., which was previously equilibrated with normal saline or some other ELISA- or RIA-compatible buffer. The eluted SIBLINGS protein was then detected by ELISA assay.

Used in this way the invention allows for the development of screening assays for the detection of SIBLINGS protein in serum. These assays involve separating the SIBLINGS protein from the SIBLINGS protein/Factor H complex and identifying the free SIBLINGS protein. Therefore, these assays can be used in conjunction with several already existing monoclonal and polyclonal antisera, as well as other antibodies developed in the future. This will allow for the more accurate assessment of SIBLINGS protein levels as well as the ability to assess the presence of several disease states in subjects. For example, the presence of tumors, Paget's disease, rheumatoid arthritis and hyperparathyroidism can be detected via the above-described assay.

A. Identification of a Highly Acidic Form of BSP in Subjects Known to Have Tumors As described above, subjects with certain types of tumors have a population of BSP which ranges from a peak which elutes at a salt concentration that is similar to that of normal subjects, to a peak which elutes later than BSP from a normal subjects. Therefore, in subjects with tumors (particularly certain types of tumors, such as those that often metastasize to bone) the serum BSP tends to be not only increased in total amount but also differs from that of a normal subject. This difference, between the BSP populations of normal subjects and subjects with tumors, can be exploited for the development of an assay for detecting tumors. One such assay is described below.

Differences in elution profiles between subjects with tumors and subjects without tumors was illustrated by taking 50 μl of serum from normal volunteers and from patients with tumors prior to surgery (no special treatment is required for drawing or holding the serum). Subsequently, 50 μl of fresh formamide and 1 μl of 100 mM DTT were added to the serum sample, and it was heated in a sand-filled heating block (100° C.) for 5 minutes, thereby separating the BSP from Factor H. The sample was then microfuged for 1 minute at 15,000×g and injected onto a 1 mL packed volume Toyopearl QAE (Toso-Haas) column, that had been pre-equilibrated with 0.05 M sodium phosphate, 50% fresh formamide, pH 7.4. The column was then washed using a flow rate of 2 mL/minutes for 5 minutes in the same low salt buffer that was used for equilibration, and then the salt concentration was linearly increased to 2 M NaCl (in the same buffer, formamide is optional) over 80 minutes (FIGS. 4A–F). Finally, the salt concentration was at 2 M NaCl for the final 15 minutes.

Similar results were seen in five different subjects with breast tumors. The method used is described above with the exception that a steeper salt gradient was used (25 minutes) followed by 2 M NaCl for the final 15 minutes (FIGS. 5A–E).

Then 100 μl of each fraction was placed in a corresponding well of a microtiter plate. It was found that Greiner High-binding plates or Nunc Maxisorp worked well for binding both the relatively non-acidic form of BSP and the relatively acidic form of BSP. The microtiter plates were incubated for between 1 and 18 hours at 4° C. The plates were then washed three times (5 minutes each) with >200 μL/well Tris-buffered saline plus 0.05% Tween 20 (TBS-T) and exposed to 100 μL of rabbit polyclonal antiserum (LF-100) raised against human BSP in TBS-T for 1 hour at room temperature. The plates were then washed again as described above, and exposed to 100 μL 1:2000 HRP-conjugated goat anti-rabbit IgG (human serum adsorbed, Kirkegaard & Perry, Gaithersburg, Md.) in TBS-T for one hour at room temperature. Finally, the plates were washed a third time and the color was developed using 3,3', 5,5' tetramethylbenzidine and $H_2O_2$ for 10–30 minutes at room temperature. Color development was stopped by that addition of 25 μL 1 N $H_2SO_4$ and analyzed at 450 nm.

Results from the above described HPLC separation technique indicated that the relatively acidic BSP was detected only in sera from subjects with various tumors and was eluted from the column generally at salt concentrations greater than 1 M NaCl. It was readily apparent that subjects with these various tumors not only had increased levels of BSP, but also that they had a different population of BSP compared to that of normal subjects.

The use of the semi-quantitative method described above allowed for the detection of a relatively non-acidic form of BSP that eluted early in the gradient (≦1 M NaCl). Of course, altering the chromatography procedure used, such as by changing the type of resin, could lead to elution of the peak at a different salt concentration, however, regardless of the separation method used there will be a sub-population of detected BSP which is less negatively charged, and will elute separately from the more negatively charged fraction. In normal subjects this relatively less negatively charged sub-population would be the only or at least the dominant population which is detected. However, in the case of normal subjects it is still possible that there will be at least a trace amount of the relatively acidic BSP. It is believed that the relatively non-acidic BSP can be used to measure bone turnover generally.

Furthermore, the relatively non-acidic BSP population has been detected in both normal subjects, as well as in subjects known to have tumors. Subjects who have prostate tumors may have elevated levels of the relatively non-acidic BSP compared to normal, which possibly indicates that there is an elevated level of bone turnover.

The above-described assay is designed to detect any tumor that makes BSP and has a sufficiently high tumor load. Using the techniques described herein, it can be determined whether any particular tumor type is associated with increased BSP levels, and particularly acidic forms of BSP. Furthermore, the identification of the relatively acidic form also provides a more sensitive assay than those based on merely assessing total serum BSP levels.

Furthermore, the above-described assay could be simplified so that only three steps are needed. These steps are, removal of the albumin by binding de-complexed BSP in low salt (≦0.2 M NaCl), eluting the relatively non-acidic BSP with 1 M NaCl and subsequently eluting the relatively acidic BSP with 2 M NaCl. Samples can then be placed in a solution that allows for antibody binding and the BSP recovered can be detected by ELISA.

B. Creation of Specific Binding Agents which Recognize Free BSP, as well as Bound BSP Nine rabbit (polyclonal) antisera against human BSP or fragments (LF-6, LF-83, LF-84, LF-100, LF-101, LF-119, LF-120 and LF-125) (including peptides) have been made. These include eight polyclonal antibodies whose activity is summarized in the Acta Orthop. Scand, (Suppl. 266) 66:61–65, 1995, as well as one made since (LF-142) that has not been published. The immunogens used to produce these antisera is provided below in Table 2.

TABLE 2

| Gene Product | Antiserum | Antigen | Known Species |
|---|---|---|---|
| Human BSP | LF-6 | human bone BSP | H,M,D,R,Mou |
| Human BSP | LF-83 | YESENGEPRGDNYRAYED- (LPH) (SEQ ID NO: 2) | H,M,D,R,Mou,C |
| Human BSP | LF-84 | YESENGEPRGDNYRAYED- (LPH) (SEQ ID NO: 2) | H,M,D,R,Mou,C |
| Human BSP, | LF-100 | AIQLPKKAGDIC-(LPH) (SEQ ID NO: 3) | 'H,M,D,R |
| Human BSP | LF-101 | AIQLPKKAGDIC-(CSA) (SEQ ID NO: 3) | H,M,D,R,P,B |
| Human BSP | LF-119 | recomb.RGDdomain (AA257-317) (SEQ ID NO: 4) | H,M,D,C |
| Human BSP | LF-120 | recomb. Frag I (AA 129-281) (SEQ ID NO: 5) | H,M,D,P,R |
| Human BSP | LF-125 | recomb. (36-61) (SEQ ID NO: 6) | H,M,P,R,S |
| Human BSP | LF-142 | CTVEY*EGEY*EY*TGANDY*DNGY*EIY*ESENY*(SEQ ID NO: 7) | H |

H = human, M = monkey, D = dog R = rat, Mou = mouse, C = chicken, P = pig, S = sheep, B = bovine, LPH = horseshoe crab hemocyanin, CSA = chicken serum albumin
*indicates sulfated tyrocine Of these 9 polyclonal antisera only LF-100 can immunoprecipitate natural BSP, and even LF-100 only binds to a portion of the BSP (<5%) when it is complexed with Factor H in human serum as detected by Western blot analysis. The other antisera precipitate little or no BSP/Factor H complex.

A similar finding was made when an artificial complex was made by incubating an excess of purified Factor H with biotinylated BSP. Once again, only the LF-100 antisera was capable of precipitating even a small portion of the BSP/Factor H complex.

The ability of polyclonal antisera against LF-100 to precipitate both bound and unbound BSP makes it highly likely that a monoclonal antibody to the same fragment would behave in the same manner. This monoclonal equivalent to LF-100 can be made by injecting into mice the identical or similar peptide-carrier conjugate, as discussed in Example 2. Clones derived from these mice can also be screened for the ability to recognize both bound and unbound BSP.

It is also believed that a monoclonal antibody against the amino-terminus or carboxy-terminus of BSP will work because these domains may remain free of the BSP-Factor H complex.

Alternatively, a monoclonal antibody may be made by first obtaining the BSP/Factor H complex, and then using the complex itself as an immunogen. The BSP/Factor H complex is obtained either through isolating it from serum or through artificially creating it using isolated Factor H and recombinant BSP. For example, 5 mg of purified human Factor H (from Quidel, LaJolla Calif.) can be complexed in vitro with 2 mg of purified human BSP from the adenoviral system described below. The complex can then be passed through a QAE column without denaturants to remove any unbound BSP. The complex can then be chromatographed on a molecular sieve column (Superose 6, Pharmacia) to separate the complex from any unbound Factor H. The resulting complex is injected into mice for monoclonal production. All clones that can bind to recombinant BSP in the initial screening can then be assayed to see if they can immunoprecipitate the BSP/Factor H complex. Even those that can not immunoprecipitate the intact complex will be useful as BSP monoclonals for the detection of BSP after it has been separated from Factor H, or for use in screening for ectopic expression as described below.

The method of using the BSP/Factor H complex as an immunogen described above can also be used with other SIBLINGS protein. Thus, monoclonal antibodies which bind to other SIBLINGS/Factor H complexes can be generated.

C. Creation of Specific Binding Agents which Recognize the Relatively Acidic Form of BSP Monoclonal antibodies that recognize the relatively acidic form of BSP can be made by using the relatively acidic BSP isolated from human serum; using relatively acidic BSP isolated from tumor tissue; using synthetic peptides which are highly phosphorylated or sulfated; or by using recombinant BSP. A particularly promising method of producing monoclonal antibodies to the relatively acidic form of BSP is by complexing relatively acidic BSP to Factor H and using the complex as an immunogen. This offers the possibility of recovering an antibody which recognizes both the bound and unbound forms of the relatively acidic BSP.

Methods of obtaining the recombinant BSP for use as an immunogen are described below, and methods of obtaining the BSP/Factor H complex for use as an immunogen are described above.

The relatively acidic form of BSP can be isolated directly from human tumors using the denaturing procedures provided in Fisher et al., *J. Biol. Chem.* 258:12723–727, 1983. Furthermore, methods of generating such monoclonal antibodies are well known to those of skill in the art and these methods are additionally detailed below. Briefly, subsequent to injection of the immunogen and fusion, the clones are screened for binding to the relatively acidic form of BSP, and then subsequently screened for binding to the relatively non-acidic form of BSP. Monoclonal antibodies that specifically detect the relatively acidic form of BSP are selected for subsequent identification of this substance in biological specimens.

D. Detection of Elevated Levels of Serum BSP in Subjects Known to Have Breast Cancer or Prostate Cancer Sera were obtained from clinically defined normal, prostate and breast cancer patients (East Coast Biologics, Inc., North Burwick, Me. and Johns Hopkins Bayview Medical Center, General Clinical Research Center) under informed consent with IRB approval and quenched samples were taken for analysis.

The day before serum was collected a 20 μg/mL solution of recombinant BSP (rBSP) was diluted out from a 1 mg/mL stock solution in 4 M guanidine HCl. 100 μl of the dilute BSP was added each well of a Greiner high binding (product number 655061) 96 well plate. The plate was then covered and incubated overnight at 4° C., however, shorter incubation periods are possible.

A solution of TBS-Tween containing 0.05 M Tris-HCl, pH 7.5, 0.15 M NaCl, 0.05% Tween 20, was prepared. A blocking buffer containing Tris buffered saline (TBS)+1% BSA+5% powdered milk was also prepared.

Samples were diluted 1:10 in a 30% formamide 40 mM phosphate buffer, pH 7.4. The samples were then reduced with 2 mM dithiothreitol (1/100 of stock,=2.5 μL) at 100° C. for 5 minutes. Residual reducing agent was inactivated by the addition of equimolar $H_2O_2$. BSP standards containing 2000, 400, 80, 16, 3.2, 0.64, and 0.13 ng/mL rBSP were then diluted out.

LF-100 antibody was then diluted 1:2,000 in TBS-Tween and 100 μl/well of Ab solution was added to polypropylene 96 well 0.5 mL volume plate (USA Scientific which is same as Nunc version). 100 μl of standard, or sample was then added to each well. The lid was then placed on the plate and reacted at room temp, 1 hour.

During incubation of the samples the rBSP coated plate, described above, was removed from the cold and 250 μl blocking buffer was added to each well. The blocking buffer was allowed to react for 5 minutes and then it was removed. The plate was then washed three times with TBS-Tween.

100 μl reaction mixture was added to each wen of the rBSP-coated plate. The plate was then incubated for 1 hour at room temp. After incubation the plate was washed three times using a buffer containing ~250 μL/well TBS-Tween, and then blotted and drained.

The secondary antibody (Goat anti-rabbit IgG (H&L), peroxidase-labeled antibody conjugate, that was human serum adsorbed) which is available from Kirkegaard & Perry, Gaithersburg, Md., was diluted 1:20,000 in TBS-Tween. 100 μL of the secondary antibody was then added to each well and the plates were incubated for 1 hour at room temp. After incubation, the plates were washed three times with ~250 μL/well TBS-Tween, blotted and then drained.

The results were visualized by providing 100 μL/well TMB (3,3', 5,5"-tetramethylbenzidine) microwell peroxidase substrate (BioFX Laboratories, Randallstown, Md.) and incubating the plates for 30 minutes. The reaction was then stopped through the addition of 100 μL stop solution/well and the plates were read at 450 nM.

The results are shown in FIG. 7, and Table 3 below. The mean concentration of BSP for the 32 subjects with breast cancer was 1170 ng/mL, the mean concentration of BSP for the 22 subjects tested with prostate cancer was 1320 ng/mL, and finally the mean concentration of BSP for the 72 normal subjects was 490 ng/mL. Clearly, most subjects tested in both the prostate group and the breast cancer group have elevated levels of BSP. Some have BSP levels that are within the normal range, however, this is expected because not all tumors are thought to express BSP.

E. Detection of Elevated Levels of Serum BSP in Subjects Over Age 50

A group of 36 individuals over the age of 50, and a group of 32 individuals under the age of 50 were tested to determine their serum BSP levels. The results are shown in FIG. 6, and Table 3, below. The mean of the group under the age of 50 was clearly less than that of the over 50 group. This assay, therefore, shows that serum levels of BSP and possibly other members of the SIBLINGS family of proteins can be used to measure bone turnover or other age-related changes.

TABLE 3

| | <50 years Normal | >50 years Normals | prostate | breast | All Normals |
|---|---|---|---|---|---|
| BSP mean (ng/mL) | 344.266 | 619.787 | 1320 | 1170 | 490.13 |
| Standard Deviation | 41.318 | 179.953 | 289.582 | 364.396 | 192.096 |
| Number of Individuals Sampled | 32 | 36 | 32 | 22 | 68 |

F. Creation of Cell Cultures Expressing Human BSP in the Highly Acidic Form

Full-length human BSP cDNA (GenBank accession number J05213; Seq. ID NO: 8) was excised from the original plasmid with EcoRI and subcloned into the EcoRI site of the pAC-EF1 adenovirus construct plasmid. This construct contained the EF-1 promoter and the bovine growth hormone (BGH) 3' polyadenylation message stabilization sequences, which is a modification of the original pAC vector (Gluzman et al., Eucaryotic Viral Vectors, Cold Spring Harbor Laboratory Press, Cold Spring Harbor, N.Y., 187–192, 1982). Selection for double cross-over within the replication-deficient adenovirus genome results in replication-deficient adenovirus that can infect most cell types but can be amplified only in specific cell culture lines. Infected cells produce the human BSP, modify it according to their specific ability, and secrete the product into the culture media.

A similar cloning scheme allowed for the production of adenovirus constructs that encode OPN and DMP1 allowing choice of all lines.

One method of producing the relatively acidic BSP involves human marrow stromal fibroblasts. These cells in primary culture modify the BSP and can produce the BSP under serum-free conditions for several days. A small percentage of the BSP made in these marrow fibroblasts elutes in the high salt portion of the anion exchange column. Additionally, this relatively acidic BSP produced by the fibroblasts infected with the adenoviral vector described above stains a darker blue (characteristic of being more acidic) than other fractions of BSP that are eluted off of the anion exchange columns earlier, when using StainsAll dye for detection ((1-ethyl-2-[3-(1-ethylnaptho[1,2d]-thiazolin-2-ylidene)-2-methyl propenyl]naptho[1,2d]thiazolium bromide, made by Eastman Kodak, Rochester, N.Y.).

Additional adenoviral constructs were also made that contain coding regions for OPN and DMP1. These constructs also can be used to express OPN and DMP1 in various cell types. It is also believed that SIBLINGS proteins, such as OPN and DMP1, also will be found to be postranslationaly modified such as has been seen in the case of BSP. Hence, the adenoviral vectors that are used to produce OPN and DMP1 can be used to produce different varieties of postranslationaly modified OPN and DMP1 by simply infecting different cell types. The expressed OPN and DMP1 can then be used in various assays for controls and to generate antibodies.

Transformation of normal fibroblasts with the BSP encoding vector (~100,000,000 cells on a total of eight 15 cm plates) allowed for the purification 20–40 mg of human BSP.

Amino terminal sequencing verified that the amino-terminus corresponds to that of human BSP. Additionally, LF-83 bound to the product, hence the carboxy-terminus of the recombinant BSP is complete at least through amino acid 295 (of 317).

Furthermore, it is believed that other primary cell lines, as well as other cancer cell lines, transformed with the vector described above produce one or both sub-populations of BSP in cell culture. Several cancer cell lines are readily available from ATCC and other sources (for example: MCF-7, CRL-1435, CRL-1470, SAOS-2, MG63 etc.).

G. Uses of Specific Binding Agents Directed Against the Relatively Acidic BSP

BSP specific binding agents, as well as other SIBLINGS protein specific binding agents, such as those made by the methods described herein, can be used for immunostaining of biopsies and sections of various tumor types, which can assist in diagnosing and determining the severity of disease. BSP levels may also be used to determine possible treatments that would be most suitable for a particular patient. For example, a very strong BSP positive breast cancer biopsy can be used as an indicator that more aggressive treatment is required following surgery (such as adjuvant chemotherapy or radiation therapy). Furthermore, monoclonal antibodies to human BSP may also be useful as immunostaining agents for determining that an otherwise inconclusive biopsy is, in fact, cancer.

Examples of BSP specific binding agents are the 13 monoclonal antibodies that were produced through the use of a synthetic 27-amino acid peptide (256T-282N). Of the 13 monoclonal antibodies produced 4 are IgG type and 9 are IgM type. This peptide was derived from the human BSP sequence, and it was designed such that it contained five tyrosine sulfates and was conjugated to a carrier protein through an amino terminal Cys keyhole limpet hemocyanin, KLH). Monoclonal antibodies from mice injected with this construct were selected if they bound to 1) the same peptide conjugated to a different carrier protein (bovine serum albumin); 2) the same peptide, but without the tyrosines sulfation conjugated to the second carrier protein; and 3) recombinant BSP made from human marrow fibroblasts infected with the virus construct described above.

H. Use of Specific Binding Agents that Bind to the Portion of BSP that does not Contribute to Increased Activity This method allows for the detection of the relatively acid BSP. The BSP/Factor H complex is disrupted and the decomplexed BSP is allowed to bind to an anti-BSP antibody coated plate or bead that specifically binds to regions of BSP that are not involved in increased acidity. (Examples of such regions are epitopes with the domains used for LF-100 or LF-125, but many other likely areas can be easily chosen.) Then a second binding agent can be added, such as an antiserum, lectin, or other chemical reagent (including those commercially available) which can detect various chemical groups that may contribute to the increased relative acidity of the BSP in cancer patient serum (phosphoserine, phosphothreonine, sulfated tyrosine, various sialic acids, various sulfated sugar groups, etc.). This second binding agent binds to the BSP that was previously bound by the first antiserum. The second antiserum or chemical reagent is then quantified using standard direct or indirect methods. This approach allows development of a quantitative assay more specific for the relatively acidic BSP without necessarily relying on a single antibody system that is specific to the BSP protein. For example, if the increased acidity is determined to be caused by a sialic acid group the BSP can be trapped by an antiserum, such as LF-100 or a monoclonal antibody devised to that domain, and then the sialic acid can be detected and quantified. The post-translational modification itself may be common in many proteins in the serum (or urine etc.), however the detection of the modification on the captured BSP makes the assay useful for the detection of a disease.

IV. Inhibition of Complement Cascade Via Expression of SIBLINGS Proteins

A. Results

The key role of Factor H is the regulation of complement and alternate complement activity. Factor H can also be 'hijacked' by invading organisms to permit pathogen evasion of complement mediated lysis. Pathogens such as *Streptococcus pyogenes* (Kotarsky et al., *J. Immunol.* 160 (7):3349–3354, 1998; Jarvis and Vedros, *Infect. Immun.* 55(1):174–180, 1987), *Neisseria gonorrhoeae* (Ram et al., *J. Exp. Med.* 188(4):671–680, 1999; Ram et al., *J. Exp. Med.,* 187(5):743–752, 1998; Diaz and Sim, *J. Immun.* 80(3): 473–482, 1995), and *Echinococcus granulosus* (Diaz and Sim, *J. Immun.* 158(8):3779–3786, 1997; Wiles et al., *J. Mol. Biol.* 272(2):253–265, 1997) bind Factor H to their cell surface and are resistant to complement-mediated cell lysis. In addition, molecular mimicry of Factor H occurs when a pathogen makes a protein that is similar in sequence to Factor H to defend against attack by the host complement system as described in Vaccinia virus (Isaacs et al., *Proc. Natl. Acad. Sci.* 89(2):628–632, 1992; Huemer et al., *Immunology* 79(4):639–647, 1993), Herpes simplex virus (Donelson et al., *Molecular Biol.* 91(1):51–66, 1998), and *Trypanosoma cruzi* (Hall and Joiner, *J. Eukaryot Microbiol.* 40(2):207–213, 1993; Kipnes and daSilva, *Braz. J. Med. Biol. Res.* 22(1):1–16, 1989; Ryden et al., *Eur. J. Biochem.* 184(2):331–336, 1989). The following data demonstrates that BSP, DMP1, and OPN play a similar role in tumor cell complement evasion.

The first model system employed was a murine erythroleukemia (MEL) cell line which when incubated with normal human serum can be readily assayed for alternate complement pathway (ACP)-mediated cell lysis (Varnet et al., *Curr. Opin. Cell Biol.,* 8(5):724–730, 1996). Cell survival was measured by both trypan blue dye exclusion and by thiazolyl blue (MTT) reduction by living mitochondria. Titration with dilutions of normal human serum and time courses were carried out to define optimal incubation conditions. At 1:10 dilution, human serum totally lysed the MEL cells as measured by both assay systems (FIG. 8A). The addition of purified recombinant BSP to MEL cells followed by treatment with normal human serum completely protected the cells from lysis (FIG. 8B). Treatment of MEL cells with recombinant OPN (FIG. 8B) or DMP1 also conferred protection from ACP-mediated cell lysis. The protection of MEL cells from alternate complement pathway-mediated cell lysis by BSP, OPN, and DMP1 exhibited dose related responses.

Figure 9B:
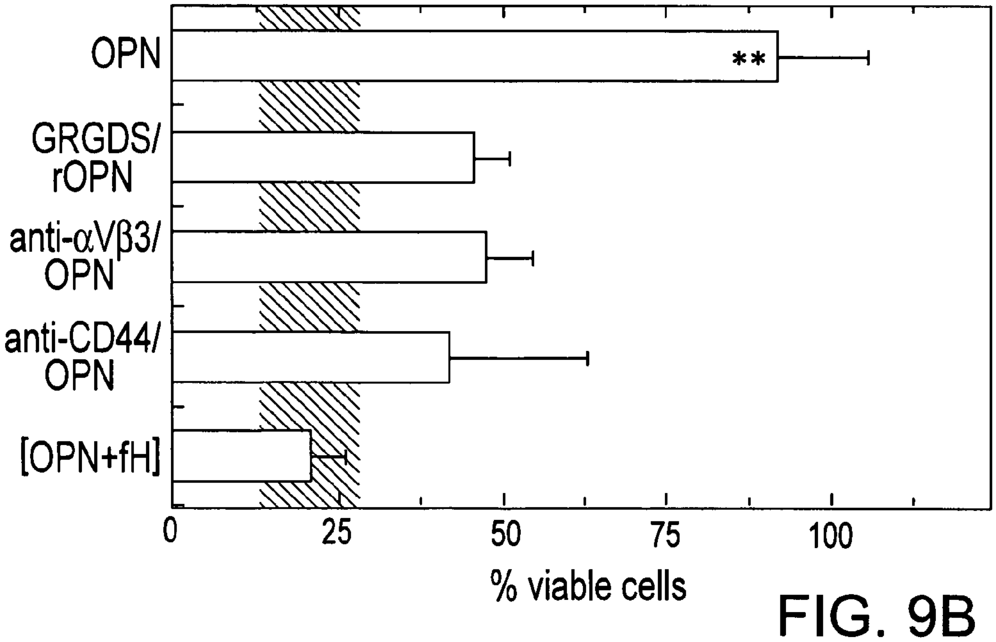

The mechanism of protection from complement-mediated lysis was investigated. Preincubation of MEL cells with rBSP in which the RGD sequence had been mutated to KAE completely removed the protective affects of this protein (FIG. 9). Furthermore, preincubation of MEL cells with either GRGDS (SEQ ID NO: 10) peptide or an $\alpha V\beta 3$ antibody (which blocks that integrin's binding activity) negated the protective effect of rBSP. Up-regulation of the $\alpha V\beta 3$ integrin has also been shown to correlate with invasive potential (Culty et al., *J. Cell Biol.* 111(6 Pt 1):2765–2774, 1990). For OPN, pretreatment with GRGDS (SEQ ID NO: 10) peptide or the $\alpha V\beta 3$ antibody reduced cell survival, though the magnitude of reduction was not as great as that seen for BSP (FIG. 9B). OPN has multiple potential receptors including αVβ1,β3, β5-containing integrin receptors as well as CD44, a receptor implicated in attachment, homing and aggregation of lymphocytes as well as neoplastic cells. Pretreatment of MEL cells with hyaluronan, a natural ligand for CD44 (Faulk and Temple, *Nature* 262 (5571):799–802, 1976), as well as with an anti-CD44 antibody also reduced the protective effect of added rOPN (FIG. 9). Treatment of MEL cells with a pre-formed complex of either rBSP-Factor H or rOPN-Factor H abolished the protection from complement-mediated lysis. For BSP, this is consistent with immunoprecipitation data that indicates that the RGD moiety is inaccessible in the solution phase Factor H complex. Hence, both of these proteins are believed to be entirely masked by Factor H shortly after being secreted by a cell.

Additional assays were conducted to determine if DMP1 could also confer protection against complement. DMP1 was found to protect the cells from complement-mediated lysis. Preincubation of the cells with antisera to either αVβ3 integrin or CD44 diminished the DMP1 protection and together they abolished it (p>0.001). Addition of the synthetic GRGDS (SEQ ID NO: 10) peptide diminished but did not abolish the protective properties of DMP1. DMP1 appears to protect the cells from attack by complement by bridging the major complement control protein, Factor H, to cell surface integrins through its RGD motif and through CD44.

To verify that the protective effect of BSP and OPN is exhibited in human cancer cells, MCF-7 breast cancer cells selected for non-adherent growth and U-266 myeloma cells were used in the alternate complement pathway cell lysis assay with guinea pig serum as the source of complement activity. Both cell types exhibited enhanced survival and protection from complement-mediated cell lysis when rBSP or rOPN were present (FIG. 10). Increasing concentration of guinea pig serum led to decreasing cell viability, while the pretreatment with either 10 μg/mL rBSP or rOPN resulted in increased cell viability.

Collectively the above described results show that DMP1, OPN, and BSP bridge Factor H to integrins and inactivate the destructive complement pathway. Theses results also confirm that OPN and DMP1 bind to CD44. Furthermore, it is likely that other members of the SIBLINGS family will have the same biological activity.

B. Experimental Procedures

1. Reagents

Rabbit Anti-human BSP antibodies LF-83, LF-100, LF-119, LF-120, LF-125 have been previously described (Fisher et al., *Bacta Orthop. Scand. Suppl.* 266(1):61–65, 1995). Rabbit Anti-BSP peptide-derived antibody LF-142 and mouse monoclonal antibodies LFmAb-11, LFmAb-2, LFmAb-12, and LFmAb-13 were raised against the sequence EY*EY*TGVNEY*DNGY*EIY*ESENGEP (amino acids 258–285; SEQ ID NO: 9) conjugated to horseshoe crab hemocyanin, where the Y* denotes tyrosine-sulfates. Normal human serum, purified human complement Factor H protein and mouse monoclonal antibody against Factor H were obtained from Quidel Corporation (San Diego, Calif.). Polyclonal antibodies against CD44 and a "functional" antibody against αVβ3 were obtained from Chemicon Co. (Temecula, Calif.). Synthetic purified glycine-arginine-aspartate-serine peptide (GRGDS; SEQ ID NO: 10) was obtained from Calbiochem-NovaBiochem Corp. (La Jolla, Calif.). Pre-immune serum, human serum adsorbed goat anti-rabbit IgG conjugated to horse radish peroxidase (HRP) as well as goat anti-mouse IgG conjugated to HRP were obtained from Kirkegaard & Perry (Gaithersburg, Md.). HRP-conjugated strepavidin and sulfosuccinimidobiotin were obtained from Pierce Chemical Co. (Chicago, Ill.). Alpha-Minimal Essential Medium (MEM), Dulbecco's Modified Essential Medium (DMEM), RPMI 1640, Eagle's Minimal Essential Medium (EMEM), Earle's Balanced salt solution, Hank's balanced salt solution and heat inactivated fetal bovine serum (FBS) were obtained from BioFluids, Inc. (Rockville, Md.).

2. Western Blotting

Samples diluted in gel sample buffer were resolved by SDS-PAGE 4–20% gradient gels (Novex Corp, San Diego, Calif.), transferred to nitrocellulose following standard conditions (Towbin et al., *Proc. Natl. Acad. Sci.* 76(9):4350–4354, 1979). Nitrocellulose membranes were rinsed with Tris-buffered saline (0.05 M Tris-HCl, pH 7.5, 0.15 M NaCl) containing 0.05% Tween 20 (TBS-Tween). After a 1 hour incubation in blocking solution (TBS-Tween+5% non-fat powdered milk) at room temperature on rotary shaker, 1:5000 primary antibody was added and incubated overnight at 4° C. The nitrocellulose sheet was washed in TBS-Tween four times for 5 minutes each time with TBS-Tween and then 1:50,000 HRP conjugated second antibody in TBS-Tween+5% milk was added and incubated for 2 hours at room temperature. Following removal of the second antibody solution the membrane was washed three times with TBS-Tween and rinsed a final time in enzyme substrate buffer for 5 min. Enhanced chemiluminescence reagents were employed for signal detection (Pierce Chemical Co., Chicago, Ill.) with x-ray film.

3. High Performance Liquid Chromatography

A Shimadzu LC10AS binary gradient system was employed for chromatographic separations. A 1.0 mL packed volume ToyoPearl QAE (TosoHaas, Montgomeryville, Pa.) column was pre-equilibrated with 0.05 M sodium phosphate, pH 7.4, containing 50% fresh formamide. A linear salt gradient increasing to 2.0 M NaCl at 2.0 mL/minute flow rate over 50 minutes was employed collecting 1 minute fractions. Size exclusion chromatography utilized a 1.0×30 cm Superose 6 column (Amersham Pharmacia, Piscataway, N.J.) equilibrated in 0.05 M sodium phosphate, pH 7.4, containing 50% fresh formamide at a flow rate of 0.5 mL/min. The column was calibrated using commercially available protein standards of known molecular weight (Amersham Pharmacia, Piscataway, N.J.).

4. Direct ELISA

Greiner high-binding 96 well plates were coated with 100 μl HPLC fractions overnight at 4° C. Plates were washed three times (5 minutes each) with TBS-Tween and exposed to 100 μl of 1:2000 primary antibody for 1 hour at room temperature. Plates were washed three times and exposed to 100 μl of 1:2000 HRP-conjugated goat anti-rabbit IgG. Following a one hour incubation at room temperature, plates were washed again three times with TBS-Tween and color was developed using 3,3', 5,5', tetramethylbenzidine and $H_2O_2$ for 10 minutes at room temperature. Color development was stopped by the addition of 25 μL 1N $H_2SO_4$ and analyzed at 450 nm.

5. Immunoprecipitation

Aliquots of normal human serum diluted 1:100 in immunoprecipitation buffer (0.1 M Tris, pH 7.2, 0.15 M NaCl, 0.05% Tween 20, and 1% aprotinin) were incubated sequentially with 0.1 mL each of (a) Protein G agarose (Kirkegaard & Perry; Gaithersburg, Md.), (b) normal rabbit serum IgGs bound to Protein G agarose; (c) rabbit anti-BSP antibodies bound to Protein G agarose. After incubation for 1 hour at 4° C. the reaction was terminated by centrifugation at 10,000×g for 5 minutes and the supernatant taken to the next immunoprecipitation. The first two incubations removed proteins binding non-specifically to agarose and to normal rabbit serum. The anti-BSP incubation immunoprecipitate was dissolved in gel sample buffer and analyzed by 4–20% gradient SDS-PAGE.

6. Production of Recombinant SIBLINGS Proteins

Adenoviral constructs encoding BSP (rBSP), DMP1 (rDMP1), and OPN (rOPN) were generated by subcloning BSP (Fisher et al., *J. Biol. Chem.* 265(4):2347–2351, 1990), BSP-KAE or OPN (Young et al. *Genomics* 7:491–502, 1990; and Kiefer et al., *Nucleic Acid Research* 17:3306, 1989) cDNA into high expression, replication-deficient adenovirus (Ad5) using EF-1 (BSP) and CMV (BSP-KAE, OPN, DMP1) promoters, respectively. The RGD->KAE constructs were made using in situ mutagenesis and the entire insert checked for fidelity. Adenoviruses were plaque-selected and propagated on HEK 293 cells (ATCC #CRL1573). Cells were harvested when cytopathic effects were present and lysed by 5 freeze-thaw cycles. Cellular debris was removed and viral particles were purified by banding twice on CsCl. After dialysis in Tris/$MgCl_2$/Glycerol Buffer at 4° C., viruses were aliquoted and frozen at −70° C. Evaluation of viral titers was carried out by plaque formation of virus dilutions on HEK293 cells (Becker et al., *Methods Cell Biol.* 43(Pt A):161–189, 1994). Typically ~2–4×$10^{11}$ pfu/mL were obtained from one viral preparation. Recombinant proteins were generated by infecting subconfluent normal human marrow stromal fibroblasts with 10,000 pfu/cell. Cells were maintained in alpha-MEM, 20% FBS and 100 IU/mL penicillin/100 μg/mL streptomycin in a humidified atmosphere of 95% air and 5% CO2 at 37° C. Medium was changed to serum-free conditions after 48 hours. Subsequently, medium was collected every 24–48 hours and frozen at −70° C. Aliquots were assayed by SDS-Gel electrophoresis and Western blot for BSP, DMP1, and OPN expression. Expression was found to be at highest levels at ~168 hours post infection. The proteins were purified by routine column chromatography. Native BSP, BSP-KAE, DMP1, and OPN proteins were purified by diluting medium from normal human marrow stromal fibroblast cells 1:1 with 40 mM phosphate buffer pH 7.4 and loading directly on a 5.0×2.0 cm column packed with ToyoPearl TSK QAE resin. A linear salt gradient to 2.0 M NaCl was employed to purify the BSP, DMP1, and OPN to ~95% purity as measured by SDS PAGE.

7. Biotinylated BSP

12 μg of recombinant human BSP was dissolved in 50 μL of PBS. 2 μL of a fresh 1 mg/mL solution of NHS-LC-Biotin (Pierce Chemical Co., Chicago, Ill.) was added and the reaction incubated at room temperature for 45 min. The unreacted biotin was removed by repeated washing with TBS-Tween and centrifugation in a Microcon 30 (Amicon, Beverly, Mass.). A final volume of 50 μL was retained.

8. Alternate Complement Mediated Cell Lysis Assay

Murine erytliroleukemia (MEL) cells (a gift of Dr. Marilyn Farquhar, Univ. CA San Diego.) grown in DMEM containing 10% fetal bovine serum and 4 mM glutamine were rinsed three times with gelatin veronal buffer with $Mg_2^+$ and EGTA (GVB-MgEGTA, Sigma, St. Louis, Mo.). Cells were resuspended in GVB-MgEGTA at a density of 5×$10^6$ cells/mL and incubated at 37° C. with different concentrations of normal human serum diluted in GVB-MgEGTA. After 2 h, cells were harvested for trypan blue exclusion assay by removing a 50 μL aliquot, incubating for 15 minutes in 0.4% trypan blue, and counting viable cells under an inverted microscope. The thiazolium blue assay was carried out at identical serum dilutions by incubating a 50 μL aliquot of the cell suspension in an equal volume of 1 mg/mL thiazolyl blue (MTT) for 45 min. Cell viability was determined spectrophotometrically by absorbance at 560 nm. Cells in GVB-MgEGTA buffer were pre-incubated with 10 μg of either rBSP, rDMP1, or rOPN in 1 mL for 10 minutes at 37° C. Normal human serum collected for good complement activity was then added at a dilution of 1:10 and the cells returned to 37° C. for 2 hours and cell viability was determined by trypan blue-exclusion and MTT assays. For the assay of human cancer cell lines, loosely adherent MCF-7 cells were selected for by sequential growth in EMEM with 2 mM L-glutamine and Earle's balanced salt solution adjusted to contain 1.5 g/L sodium bicarbonate, 0.1 mM non-essential amino acids and 1.0 mM sodium pyruvate and 10%; fetal bovine serum, while U-266 cells were cultured in RPM 1640 medium containing 15% fetal bovine serum. Cells were collected by centrifugation and rinsed three times with GVB-MgEGTA buffer and subsequently treated exactly as for MEL cells, substituting guinea pig serum (Sigma, St. Louis, Mo.) for human serum.

EXAMPLES

Example 1

Isolation of SIBLINGS Proteins and the Relatively Acidic form of BSP

A. Disruption of SIBLINGS/Factor H Complex

A variety of methods of disrupting protein—protein interactions are well known in the art. Such methods can involve treatment with harsh chemicals and/or severe temperatures. Typically protein complexes such as the SIBLINGS/Factor H complex can be disrupted through the use of reducing agents, denaturants and/or increased temperatures. The SIBLINGS/Factor H complex also can be disrupted using a combination of reducing agents, denaturants, and increased temperatures. The particular method of disrupting the complex is not critical, as long as the complex is disrupted.

Reducing agents are agents that are capable of donating hydrogen atoms, and as such serve to disrupt disulfide bonds between amino acids. These agents particularly disrupt disulfide bonds that commonly link two proteins or portions of the same protein together. Commonly used reducing regents are β-mercaptoethanol, 1,4-dithiothieitol (DTT) and trialkyl phosphines. Additionally, the ability of a reducing agent to facilitate the separation of SIBLINGS proteins from Factor H will be increased by increasing the temperature at which the solution containing the reducing agent and SIBLINGS/Factor H complex is incubated.

Denaturants serve to relax the conformational structure of proteins, and there are a variety of denaturants that can be employed to effectuate the separation of SIBLINGS proteins from Factor H. Examples of denaturants that are particularly useful in conjunction with ion exchange columns are urea and formamide. However, denaturants such as guanidine hydrochloride or guanidine thiocyanate also may be useful for separating Factor H from SIBLINGS proteins in non-ion exchange based methods. The ability of the denaturant to relax the protein will also be enhanced by increasing the temperature at which the sample containing the SIBLINGS/Factor H complex is incubated.

SIBLINGS proteins, such as BSP can also be separated from Factor H by adding competitive binding agents to the sample containing the BSP/Factor H complex. Upon addition to the sample, a competitive binding agent binds to Factor H and displaces BSP. Ideally, the agent used binds to Factor H selectively and not to BSP. Examples of such competitive binding agents are, recombinant fragments of BSP, sialic acids, and synthetic BSP fragments.

Since a variety of methods can be employed to separate Factor H from SIBLINGS proteins, the invention also provides a method of determining when the proteins have become separated. As mentioned above, when Factor H is complexed to SIBLINGS proteins, the relatively acidic BSP, or to the relatively non-acidic BSP, it masks the ionic charge normally associated with protein. Therefore, when the complex is placed on an anion exchange column, it readily flows through the column and the complex fails to bind. Hence, after treatment with one or more denaturants and reducing agents, the sample can be tested for the its ability to bind to an anion exchange column. This assay can confirm whether separation of Factor H from the complex has occurred.

It is also possible to simultaneously confirm that a SIBLINGS protein has been separated from Factor H and measure the SIBLINGS protein level using column chromatography. This can be done by first mixing a sample with an anion exchange resin under conditions that disrupt the Factor H/SIBLINGS complex and then allowing the SIBLINGS protein to bind to the anion exchange resin. The un-complexed SIBLINGS protein will then bind to the resin, denaturants and other contaminants can be washed away, and the SIBLINGS-resin complex can then be directly assayed using SIBLINGS protein specific binding agents.

Additionally, the column conditions can be modified such that either the relatively acidic BSP or the relatively non-acidic BSP remains bound. Thus, BSP specific binding agents used to detect the BSP resin complex will actually be detecting either the relatively non-acidic BSP or the relatively acidic BSP.

B. Separation of the Total Bound SIBLINGS Protein from Factor H and the Separation of the Relatively Non-Acidic BSP from the Relatively Acidic BSP The separation of the total bound SIBLINGS protein from Factor H, and the subsequent separation of the relatively acidic and the relatively non-acidic BSP, can be accomplished using multi-step procedures that include various chromatographic techniques (Robyt and White, Biochemical Techniques Theory and Practice, Waveland Press, Inc, 1990). Such multi-step procedures will commonly operate to separate the proteins by exploiting their different physical characteristics. There are many different methods that can be used to effectively separate SIBLINGS protein from Factor H, as well as to separate the relatively acidic BSP from the relatively non-acidic SIBLINGS protein. Therefore, the following discussion provides a broad description of various chromatography techniques that can be used in either a single step process or in multi-step process. Furthermore, it is possible that a single variety of chromatography be repeatedly used to effectuate either the isolation of the relatively acidic SIBLINGS protein, or the entire population of SIBLINGS protein present in the sample.

1. Column Chromatography

One method of isolating the SIBLINGS protein and/or relatively acidic BSP is through adsorption chromatography. This method involves the exploitation of the differential affinity of the protein for the medium in the column, and the affinity of the protein to the eluting solvent. An example of a suitable medium for use in the column is hydroxyapatite, which is a crystalline form of calcium phosphate. This medium tends to adsorb acidic proteins (such as BSP), which can subsequently be eluted with phosphate ions, which have a high affinity for the calcium ions present in the hydroxyapatite.

Ion exchange chromatography can also be used to isolate SIBLINGS protein, and/or the relatively acidic BSP. This approach is a variation of adsorption chromatography, in which the solid adsorbent has charged groups chemically linked to an inert solid. The ionic charge of the SIBLINGS protein then causes the SIBLINGS protein to become linked to the chemically charged groups on the solid support, and the SIBLINGS protein is subsequently released by passing a solution containing an ion gradient over the solid adsorbent. Examples of solid supports that can be used in this technique include DEAE-cellulose, DEAE-Sephadex, DEAE-Bio-Gel, DEAE cellulose, DEAE sepharose, DEAE sephacryl, DEAE trisacryl, Q sepharose, ecteola cellulose, QAE cellulose, express ion exchanger Q, PEI cellulose, and other polystyrene-based anion exchangers.

Another type of adsorption chromatography which can be used to isolate SIBLINGS protein and/or the relatively acidic form of BSP is affinity chromatography. This method involves covalently linking to an inert solid support a ligand which has binding affinity for the protein of interest, which in this case is either SIBLINGS protein or the relatively acidic BSP. Commonly, the ligand is a specific binding agent, which selectively binds the protein of interest as it contacts the solid support. Alternatively, the SIBLINGS protein and/or the relatively acidic BSP can be separated based upon hydrophobicity. For example, alkyl chains may be linked to the inert support, to supply sites for hydrophobic bonding interactions. The eluting solvent then contains a hydrophobic gradient.

High performance liquid chromatography provides yet another method that can be utilized to isolate SIBLINGS protein and/or the relatively acidic BSP. All of the major classes of chromatographic separations are possible using this method, for example, adsorption, liquid—liquid partition, ion exchange, exclusion, and affinity chromatography can be used in conjunction with HPLC. Additionally, the HPLC method allows for reversed phase and ion pair partition. Reversed phase partition allows for quick elution using a non-polar stationary phase and a polar mobile phase, while ion pair partition involves pairing the charged polar substance with its counter ion to create a less polar species that then flows through the column.

2. Electrophoresis

Electrophoresis is a well-established technique for the separation and analysis of mixtures by differential migration and separation of molecules in an electric field, based on differences in mobility through a support. Many different forms of electrophoresis have been developed to permit the separation of different classes of compounds. These forms include paper and cellulose acetate electrophoresis, thin-layer electrophoresis, gel electrophoresis, immunoelectrophoresis and isoelectric focusing. Paper electrophoresis operates best for the separation of relatively low molecular weight protein molecules, and gel electrophoresis is a much better candidate for use in isolating the relatively acidic BSP. There are a variety of different matrices available for forming gels, but matrices with a relatively smaller pore size are most suitable for the separation of two similar molecules. Furthermore, proteins may be separated based upon size by conducting the electrophoresis under disassociating conditions, for example using SDS. The SDS relaxes the protein and masks the ionic charge of the protein, which leaves protein size as the only distinguishing characteristic. Hence in the case of the relatively acidic BSP, SDS would not be used for separating the two populations of BSP (the relatively acidic versus the relatively non-acidic), because the separation will depend on the ionic charge that would be masked by SDS.

Separation can also be achieved using immunoelectrophoresis, in which proteins are separated on a gel based upon their charge-to-mass ratio and their antigenicity. This is done by first separating the proteins on a gel, and then adding an antibody specific for the protein of interest to a well created in the gel, and allowing the antibody to diffuse through the gel. Precipitate then forms in regions in which the antibody reacts with the protein.

The relatively acidic form of BSP can also be isolated through the use of isoelectric focusing. In this type of electrophoresis the protein is placed on a substrate having a pH gradient, and it will move under the influence of an electrical field until it reaches an equilibrium point with the pH gradient.

Finally, the characterization of the relatively acidic BSP population indicates that other SIBLINGS proteins may exist in multiple forms. Moreover, SIBLINGS proteins may also have relatively acidic population and these populations can be detected using the above described techniques.

Example 2

Identifying SIBLINGS Proteins with Specific Binding Agents

A SIBLINGS protein can be identified using specific binding agents. These specific binding agents may bind for example, BSP generally, or they may selectively bind to the relatively acidic BSP, the relatively non-acidic BSP, or the exposed portion of SIBLINGS protein in the SIBLINGS/Factor H complex. The latter specific binding agent will be particularly useful for more accurately determining the total amount of SIBLINGS protein in the biological specimen without the need to separate the SIBLINGS protein from the Factor H.

A. Antibodies

Antibody preparations prepared according to these protocols are useful in quantitative immunoassays such as ELISAs, Western blotting and RIAs, to determine concentrations of antigen-bearing substances in biological samples; they are also used semi-quantitatively or qualitatively to identify the presence of antigen in a biological specimen.

1. Production of an Antibody to SIBLINGS Proteins

Monoclonal or polyclonal antibodies may be produced to SIBLINGS proteins or portions thereof. Optimally, antibodies raised against a particular SIBLINGS protein, such as BSP will specifically detect BSP. That is, antibodies raised against BSP would recognize and bind BSP and would not substantially recognize or bind to other proteins found in human cells. The determination that an antibody specifically detects a SIBLINGS protein, such as BSP is made by any one of a number of standard immunoassay methods; for instance, the Western blotting technique (Sambrook et al., In Mol. Clon.: A Lab. Man., Cold Spring Harbor, N.Y., 1989). To determine that a given antibody preparation (such as one produced in a mouse against the human BSP) specifically detects BSP by Western blotting, serum is extracted from a subject (for example, to obtain lymphocytes) and electrophoresed on a sodium dodecyl sulfate-polyacrylamide gel. The proteins are then transferred to a membrane (for example, nitrocellulose or nylon) by Western blotting, and the antibody preparation is incubated with the membrane.

After washing the membrane to remove non-specifically bound antibodies, the presence of specifically bound antibodies is detected by the use of an anti-mouse antibody conjugated to an enzyme such as alkaline phosphatase; application of the substrate 5-bromo-4-chloro-3-indolyl phosphate/nitro blue tetrazolium results in the production of a dense blue compound by immuno-localized alkaline phosphatase. Antibodies that specifically detect SIBLINGS protein will, by this technique, be shown to bind substantially only the SIBLINGS protein band (which will be localized at a given position on the gel determined by its molecular weight). Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-SIBLINGS protein binding.

Antibodies that specifically bind to SIBLINGS protein belong to a class of molecules that are referred to herein as specific binding agents. Specific binding agents that are capable of specifically binding to SIBLINGS protein may include polyclonal antibodies, monoclonal antibodies (including humanized monoclonal antibodies) and fragments of monoclonal antibodies such as Fab, F(abγ)2 and Fv fragments, as well as any other agent capable of specifically binding to SIBLINGS proteins.

Depending on the desired specificity of the antibody, different forms of a SIBLINGS protein can be used as immunogens for injection into subjects for the creation of antibodies. To create antibodies which recognize the exposed portion of a SIBLINGS protein when it is bound to Factor H, the entire SIBLINGS/Factor H complex can be used as an immunogen. Similarly, if the creation of an antibody specific for the relatively acidic BSP is desired, the relatively acidic BSP can be isolated and used to inoculate a mouse. Additionally, as mentioned below, fragments of the relatively acidic BSP or fragments of the exposed portion of BSP can be used as immunogens for the creation of specific binding agents.

Regardless of the particular form of SIBLINGS protein used to create the immunogen the concentration of protein in the final preparation is adjusted, for example, by concentration on an Amicon filter device, to the level of a few micrograms per milliliter. Alternatively, as previously mentioned, peptide fragments of the SIBLINGS proteins may be utilized as immunogens. Such fragments may be chemically synthesized using standard methods, or may be obtained by cleavage of the whole SIBLINGS protein followed by purification of the desired peptide fragments. Peptides as short as 3 or 4 amino acids in length are immunogenic when presented to the immune system in the context of a Major Histocompatibility Complex (MHC) molecule, such as MHC class I or MHC class II. Accordingly, peptides comprising at least 3 and preferably at least 4, 5, 6 or more consecutive amino acids of the disclosed SIBLINGS protein amino acid sequences may be employed as immuogens to raise antibodies.

Because naturally occurring epitopes on proteins frequently include amino acid residues that are not adjacently arranged in the peptide when the peptide sequence is viewed as a linear molecule, it may be advantageous to utilize longer peptide fragments from the SIBLINGS protein amino acid sequence in order to raise antibodies. Thus, for example, peptides that comprise at least 10, 15, 20, 25 or 30 consecutive amino acid residues of the BSP amino acid sequence may be employed. Monoclonal or polyclonal antibodies to the intact BSP or peptide fragments of this protein may be prepared as described below.

2. Monoclonal Antibody Production by Hybridoma Fusion

Monoclonal antibody to epitopes of BSP identified and isolated as described can be prepared from murine hybridomas according to the classical method of Kohler and Milstein, Nature 256:495, 1975, or derivative methods thereof. Briefly, a mouse is repetitively inoculated with a few micrograms of the selected protein over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media such as aminopterin (HAT media). The successfully fused cells are diluted and aliquots of the dilution placed in wells of a microtiter plate, where growth of the culture is continued. Antibody-producing clones are identified by detection of antibody in the supernatant fluid of the wells by immunoassay procedures, such as ELISA, as originally described by Engvall, *Enzymol.* 70:419, 1980, and derivative methods thereof. Selected positive clones can be expanded and their monoclonal antibody product harvested for use. Detailed procedures for monoclonal antibody production are described in Harlow and Lane, Antibodies, A Lab. Man., Cold Spring Harbor, N.Y., 1988. In addition, protocols for producing humanized forms of monoclonal antibodies (for therapeutic applications) and fragments of monoclonal antibodies are known in the art.

3. Polyclonal Antibody Production by Immunization

Polyclonal antiserum containing antibodies to heterogeneous epitopes of a single protein can be prepared by immunizing suitable animals with the expressed protein, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appear to be most reliable. An effective immunization protocol for rabbits can be found in Vaitukaitis et al., *J. Clin. Endocrinol. Metab.* 33:988–991, 1971.

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony et al., In Handbook of Experim. Immunol., Wier, D. ed., ch. 19. Blackwell, 1973. Plateau concentration of antibody is usually in the range of 0.1 to 0.2 mg/mL of serum (about 12 M). Affinity of the antisera for the antigen is determined by preparing competitive binding curves, as described, for example, by Fisher, 1980.

4. Antibodies Raised by Injection of SIBLINGS protein cDNA

Antibodies may also be raised against SIBLINGS proteins by subcutaneous injection of a DNA vector that expresses the SIBLINGS protein in laboratory animals, such as mice. Delivery of the recombinant vector into the animals may be achieved using a hand-held form of the Biolistic system (Sanford et al., *Particulate Sci. Technol.* 5:27–37, 1987) as described by Tang et al., *Nature* (London) 356:152–154, 1992. Expression vectors suitable for this purpose may include those that express a cDNA encoding a SIBLINGS protein under the transcriptional control of either the human β-actin promoter or the cytomegalovirus (CMV) promoter. Methods of administering naked DNA to animals in a manner to cause expression of that DNA in the body of the animal are well known and are described, for example, in U.S. Pat. No. 5,620,896 (DNA vaccines against rotavirus infection), U.S. Pat. No. 5,643,578 Immunization by inoculation of DNA transcription unit) and U.S. Pat. No. 5,593,972 (Genetic immunization), and references cited therein.

5. Antibody Fragments

Antibody fragments may be used in place of whole antibodies and may be readily expressed in prokaryotic host cells. Methods of making and using immunologically effective portions of monoclonal antibodies, also referred to as antibody fragments, are well known and include those described in Better and Horowitz, *Advances in Gene Technol.: The Mol. Biol. Of Immune Disease & the Immune Response* (ICSU Short Reports), 1989; Glockshuber et al., *Biochem.* 29:1362–1367 (A Comparison of Strategies to Stabilize Immunoglobulin $F_v$ Fragments), 1990; and U.S. Pat. No. 5,648,237 (Expression of Functional Antibody Fragments), U.S. Pat. No. 4,946,778 (Single Polypeptide Chain Binding Molecules), and U.S. Pat. No. 5,455,030 (Immunotherapy Using Single Chain Polypeptide Binding Molecules), and references cited therein.

6. Humanized Antibodies

Humanized monoclonal antibodies are preferred in clinical applications. Methods of making humanized monoclonal antibodies are well known, and include those described in U.S. Pat. No. 5,585,089 (Humanized Immunoglobulins), U.S. Pat. No. 5,565,332 (Production of Chimeric Antibodies—A Combinatorial Approach), U.S. Pat. No. 5,225,539 (Recombinant Altered Antibodies And Methods Of Making Altered Antibodies), U.S. Pat. No. 5,693,761 (Polynucleotides Encoding Improved Humanized Immunoglobulins), U.S. Pat. No. 5,693,762 (Humanized Immunoglobulins), U.S. Pat. No. 5,585,089 (Humanized Immunoglobulins), and U.S. Pat. No. 5,530,101 (Humanized Immunoglobulins), and references cited therein.

Antibody preparations prepared according to these protocols are useful in quantitative immunoassays to determine concentrations of antigen-bearing substances in biological samples; they are also used semi-quantitatively or qualitatively to identify the presence of antigen in a biological sample.

Example 3

Characterizing SIBLINGS Protein Populations in Biological Specimens

In addition to the assays provided above, the present invention allows for further characterization of SIBLINGS protein populations in biological specimens, and the development of screening assays that can detect tumors, as well as abnormal bone turnover. It is additionally contemplated that tumors such as sarcomas and carcinomas, fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma) may prove to express BSP and be detectable through the use of the disclosed assays.

A. Development of Screening Assays

The invention allows for the development of screening assays that can detect other disease states which are associated with elevated SIBLINGS protein levels, and/or shifts in the population of BSP from the relatively non-acidic BSP to the relatively acidic form of BSP. This can be done by separating the SIBLINGS protein from Factor H and correlating the relative concentration of SIBLINGS protein in the test sample to the relative concentration in a control. The control in many cases is a like sample from a subject that does not have the particular malady in question. For example, a screening assay can be developed to detect abnormal bone turnover in subjects having osteoporosis or osteoarthritis, by taking a sample from the subject that is know to have the particular malady, and characterizing the SIBLINGS protein concentration using the methods provided above. This same procedure can be then be used to characterize a sample from a normal subject and subsequently a correlation can be drawn between the results from the two subjects. If present the correlation can then be used to detect the malady in other subjects.

B. Controls for Assays in which the Relatively Acidic BSP is Used as a Marker

The above data shows subjects suffering with breast, prostate, thyroid, multiple myeloma and lung tumors have readily distinguishable populations of BSP. These differences have permitted the development of an assay that can be used to detect the presence or recurrence of such tumors (such as recurrence following surgical excision of a tumor). Generally, such assays include a control that allows a comparison to be made between a normal individual and the test subject. However, in some cases this control can be recombinantly expressed BSP, or the test sample can be classified as positive for a tumor based upon the ratio of the relatively non-acidic BSP to the relatively acidic BSP. The above separation methods describe different mechanisms for separating proteins based upon ionic charge and these methods can be used to provide information on the relative concentration of the relatively non-acidic form of BSP, as well as the relatively acidic form of BSP. Therefore, used in this way the assay does not require the use of an external control; rather the ratio itself can be used to indicate the presence of a tumor.

Example 4

Use of Members of the SIBLINGS Family of Proteins to Confer Protection Against Complement The above-described methods and results show that when members of the SIBLINGS family of proteins are associated with cells they can serve to protect the cells from complement mediated lysis. In the case of tumor cells it is likely that the expression of SIBLINGS proteins serves to protect the tumor from complement lysis. This protection may be especially important during the process of metastasis when tumor cells are invading other tissue such as bone.

The complement protective activity of SIBLINGS proteins can also be exploited to protect cells and/or implants from complement mediated immune responses. In the case of implants SIBLINGS proteins can be used to coat implants such as described in U.S. Pat. No. 6,024,918 to Hendriks, et al. or they can be delivered from a reservoir that is placed in the body. This protection can be imparted to a cell by either coating the cell with the SIBLINGS protein, or genetically engineering a cell to express the SIBLINGS protein. Used in this way a cell that has been engineered to express a transgene is designed to also express one or more of the members of the SIBLINGS family of proteins. The co-expression of the SIBLINGS protein then facilitates the binding of Factor H to the transgenic cell. This binding results in the cell becoming protected from complement mediated lysis. Expressing the SIBLINGS protein with a membrane localization peptide could further enhance the protection conferred to the transgenic cell.

The complement protective activity of SIBLINGS proteins also could be used to provide protection against non-self cells that are introduced into a subject's body, for example by implantation of a graft. Used in this way a transgene encoding the SIBLING protein could be delivered to the graft via various vectors such as described below.

A. Expression Cassette Transfer

A preferred method of supplying exogenous SIBLINGS proteins is by transferring a vector comprising an expression cassette to cells associated with the region of interest such that the cells express the SIBLINGS protein.

1. Expression Cassettes

Expression cassettes employed in the present inventive methods are of any type appropriate for cells containing the cassette to express the protein of interest. Thus, for example, an expression cassette comprises a polynucleotide encoding BSP operably linked to a promoter.

Any promoter and/or enhancer sequence appropriate for controlling expression of polynucleotides from the vector can be used in constructing an expression cassette. While such promoters/enhancer elements are well known in the art, examples of suitable promoters include prokaryotic promoters or viral promoters, (e.g., ITRs, or LTRs; immediate early viral promoters, such as herpesvirus IE promoters, or cytomegalovirus (CMV) IE promoters; or other viral promoters, such as Rous Sarcoma Virus (RSV) promoters, or Murine Leukemia Virus (MLV) promoters). Other suitable promoters are eukaryotic promoters, such as constitutively active promoters (e.g., the β-actin promoter), signal specific promoters (e.g., inducible promoters, such as a promoter responsive to TNF), or tissue-specific promoters, (e.g., those active in epidermal tissue, dermal tissue, tissue of the digestive organs such as cells of the esophagus, stomach, intestines, or colon), smooth muscles, such as vascular smooth muscles, cardiac muscles, skeletal muscles, lung tissue, hepatocytes, lymphocytes, endothelial cells, sclerocytes, kidney cells, glandular cells (e.g., those in the thymus, ovaries, testicles, pancreas, adrenals, pituitary, etc.), tumor cells, cells in connective tissue, cells in the central nervous system (e.g., neurons, neuralgia, etc.), cells in the peripheral nervous system, or other cells of interest.

Which promoter is used in a given expression cassette will depend, in part, on the choice of vector. Thus, for example, an expression cassette can comprise a native retroviral LTR promoter operably linked to a coding polynucleotide when the vector is a retroviral vector.

In addition to a promoter, an expression cassette will also contain a polynucleotide encoding the protein of interest. Preferably, the polynucleotide is a synthetic DNA, cDNA or genomic DNA fragment encoding the SIBLINGS protein or fragment thereof that imparts protection against complement mediated lysis to the cell that expresses it. Expression cassettes can also include other polynucleotides, such as a polyadenylation sequence. Also, expression cassettes can encode more than one SIBLINGS protein.

2. Vectors

An expression cassette for use in the present inventive methods such as those described supra is contained within a vector. Of course, in addition to the SIBLINGS protein encoding sequence, the vector can include other expression cassettes, such as, for example, cassettes for expressing a selectable marker (e.g., β-gal or a marker conferring resistance to a toxin), a pharmacologically active protein, a transcription factor, or other biologically active substances.

Any vector appropriate for transferring an exogenous expression cassette to a cell is included within the scope of the present inventive methods. Preferably, the vector is a viral vector. Examples of viral vectors employed in accordance with the present inventive method include, but are not limited to, retroviral vectors, adenoviral vectors, adeno-associated viral vectors, herpesviral vectors, SV40 viral vectors, polyoma virus vectors, pappiloma virus vectors, picnoravirus vectors, vaccinia virus vectors, or other suitable vectors.

In addition to viral vectors, any non-viral vector capable of expression upon infection of target cells can be used in the present inventive methods. Preferably, a non-viral vector is a plasmid.

The skilled artisan will be able to incorporate an expression cassette into the nucleic acid sequence of the vector. Methods for incorporating expression cassettes into viral vectors are well known in the art (see e.g., Sambrook, et al. *Molecular Cloning: a Laboratory Manual,* 2d edition, Cold Spring Harbor Press, 1989) and include direct cloning, site specific recombination using recombinases, such as the flp recombinase or the cre-lox recombinase system (reviewed in Kilby et al., *Trends in Genetics,* 9:413–21, 1993), homologous recombination, and other suitable methods of constructing a recombinant vector.

3. Target Cells

The present inventive methods also comprise transferring an expression cassette to cells associated with the region of interest (i.e., a graft). Any suitable cells associated with the region of interest which are capable of supporting expression of the coding polynucleotide of the cassette are encompassed within the present inventive methods. Such cells can be cells in situ, such as cells of the graft tissue.

Following transfer of the vector comprising the expression cassette to the cells in vitro, the cells associated with the region are transferred to the region of interest. Transfer of cells in vitro to a region of interest is accomplished by known means. For example, cells can be transferred to internal tissue of a patient by methods described herein. Further methods of transferring cells containing an expression cassette are described in International Patent Application No. WO 96/00006, (Billiar et al.).

4. Vector Transfer

The present inventive methods comprise transferring a vector comprising an expression cassette, such as those described herein, to cells associated with the region of interest (e.g., graft). Any method of transferring the expression cassette to the cells is appropriate so long as a product of the expression cassette is produced in the cells.

a. Non-Viral Vectors

Any means of introducing non-viral vectors into target cells, such as by direct DNA injection, electroporation, calcium-phosphate mediated cell transfection, lipofectamine, DAEA-dextran-mediated cell transfection, polybrene-mediated delivery, host cell fusion, microinjection, and polylysine-mediated cell transfection is appropriate within the present inventive context. Such methods are well known in the art, and some are described in International Patent Application No. WO 96/00006, (Billiar et al.). A preferred method of transferring the expression cassette within a nonviral vector, such as a plasmid, is via liposome-mediated transfection of the target cells, such as endothelial cells, in vitro or in situ. If the vector is transfected in vitro, the cells associated with the region of interest are subsequently transferred to the patient.

b. Viral Vectors

Transfer of an expression cassette to cells associated with the region of interest where the cassette is within a viral vector is accomplished by infecting the cells with the virus. Where the virus is a retrovirus, the virus can be first transfected into an appropriate packaging cell line for generation of infectious virus. Cells associated with the region of interest can be infected in vitro or in situ. Moreover, the mode of transfer of the expression cassette does not depend on the identity of the coding polynucleotide.

c. In Vitro Delivery

Infectious viruses are used to infect cultured cells in vitro. The precise method for infecting target cells in vitro will depend upon the viral vector used; however, such methods are well known in the art. Some suitable methods are described in International Patent Application No. WO 96/00006, (Billiar et al.).

5. In Situ Delivery

Some applications of the present inventive methods involve transfer of expression cassettes in situ. In situ transfer can be either in vivo (i.e., to a wound or to a graft following implantation), or ex vivo (i.e., to a graft prior to implantation). Any method of delivering the vector comprising the expression cassette to cells associated with the region of interest in situ is within the present methods. Such methods also apply to transfer of exogenous cells to the region of interest. Methods for in situ delivery of vectors preferably involve physically segregating the region of interest from the remainder of the patient's tissue in order to properly target the vector within the region. Upon segregation, the vector is applied to the region of interest in a manner appropriate to transfer the expression cassette into the cells associated with the region of interest.

Tissue ex vivo, such as, for example, a graft, is completely isolated from the patient. For ex vivo vector transfer, the vector can be applied to the tissue in any suitable manner, e.g., in a carrier appropriate for transferring the vector. For example, the tissue can be incubated in a carrier containing the vector particles by any suitable incubation method. Other tissue can be perfused with the solution containing the vector.

The vectors or exogenous cells preferably remain in contact with the wound or tissue for a period of time sufficient to promote the transfer. For example, a carrier comprising a vector will remain in contact with the wound or ex vivo tissue from about one minute to about 2 hours, more preferably between 10 minutes and an hour, and most preferably from about 20 minutes to 40 minutes. In many applications, the carrier will optimally remain in contact with the wound or tissue for about 30 minutes.

6. Internal Delivery

For in situ delivery of a vector internally, the region of interest desirably is further segregated from the remainder of the subject's tissue. Any of a variety of known surgical procedures for physically segregating the region of interest is appropriate. Various endovascular surgical techniques appropriate for segregating a region of interest are available, depending upon the location of the target.

Endovascular surgical procedures include, but are not limited to, balloon angioplasty, intravascular stents, laser-assisted balloon angioplasty, double balloon catheterization, mechanical endarterectomy and vascular endoscopy. For a review of endovascular alternatives, see generally Ahn, "Endovascular Surgery," in Vascular Surgery, A Comprehensive Review, Ed. W. S. Moore, W. B. Saunders & Co., Philadelphia, 1993.

Several catheter designs can be utilized for local delivery of a vector. One catheter design consists of two independently inflated balloons, one proximal and one distal to the vascular delivery site. Inflation of these balloons provides an evacuated isolated arterial segment into which vectors for expression cassette delivery can be infused. This system is, however, limited by absence of distal arterial perfusion. A second catheter design developed by Wolinsky allows the infusion of the SIBLINGS protein-encoding vector through 25–100 μM pores under pressures up to 5 atm. This perfusion pressure increases the depth of penetration by the vectors and additionally increases expression cassette transfer efficiency. Yet another catheter design utilizes an expandable stent which traps the balloon against the arterial wall and allows intramural delivery of the expression cassette through spaces in the stent material. Additionally, these stents can be modified with burrs that create holes deeper in the vessel wall and allow flow of the expression cassette delivery agents to these sites to allow more uniform delivery of the expression cassette throughout the vessel wall.

Another delivery mechanism is to coat the catheter with a hydrophilic polyacrylic acid polymer that acts as a drug-absorbing sponge. By disrupting the vessel during the angioplasty procedure, this hydrogel is deposited within the vessel wall and will allow sustained delivery of the vector at the arterial wound site. Additionally, the iontophoretic balloon catheter is a catheter design that uses low electrical current to change the cell membrane polarity and allow the diffusion of charged DNA particles into the cell. This is a potential delivery mechanism for plasmid DNA expression cassette constructs. Also, biodegradable stents formed from agents such an ethylenevinyl acetic copolymer are appropriate for localized delivery to vascular tissue. Alternatively, an intravascular stent can be utilized wherein the endovascular scaffold of the stent is bathed in a ointment, cream, lotion, colloidal dispersion such as a gel or magma or any other acceptable carrier which comprises the SIBLINGS protein encoding vector for delivery to the targeted portion of a vessel segment. This solution is applicable to either an in situ or ex vivo based vessel delivery.

Example 5

Additional Examples of Methods for Detecting and/or Quantifying SIBLINGS Proteins The following assays describe the detection of BSP, however, these assays, with appropriate modifications (i.e., antibody substitutions), can also be used to detect other SIBLINGS proteins.

A. Chemiluminescent Sandwich Assay for BSP in Human Serum

Pierce Reacti-Bind White Opaque 96-Well EIA plates (product # 15042) are coated with 100 μL of 1 μg/ML Goat anti Mouse IgG (H & L), human serum adsorbed (Kirkegaard & Perry, Gaithersburg, Md.) in PBS. The plates are then covered and incubated overnight at 4° C. The next morning the wells are emptied and 250 μL of 1% bovine serum albumin is added for 15 min. The albumin is then removed and the plates are washed 3 times with ~300 μL PBS-0.05% Tween 20 (PBS-T) for 5 minutes each at room temperature. 100 μL 1:1000 LFMb-2 (monoclonal to human BSP) in PBS-T is added to each well and the plate is incubated again for 1 hour at room temp and then washed three times (PBS-Tween).

The samples are prepared from 25 μL human. 50 μL fresh formamide and 1 μL of 0.1 M Dithiothreitol is added to the sample and the sample is then heated at 100° C. for 5 minutes and diluted to 1 mL with PBS-T containing 0.03% $H_2O_2$. This addition dilutes the fomamide to levels sufficiently low enough to promote normal antibody binding and the $H_2O_2$ inactivates the remaining DTT.

The BSP standard (5 ng to 0.15 ng) and a negative control (without BSP) are prepared in PBS-T and added to individual wells. 100 μL diluted sample is also added to the individual wells. The samples and the standards are then incubated 1 hour at room temperature and then washed 3 times with PBS-Tween. 100 μL of 1:1000 LF-100 polyclonal (rabbit anti-human BSP) antibody in PBS-T plus 1% normal mouse serum is then added to each well and the plate is incubated for 1 hour at room temperature and then washed 3 times. 100 μL of 1:50,000 diluted peroxidase-conjugated goat anti rabbit IgG (H&L), multi-serum adsorbed (Kirkegaard & Perry) is then added to each well and the plate is incubated for 1 hour at room temperature, washed 3 times (PBS-Tween).

The results are then visualized by adding 100 μL of Pierce Supersignal ELISA Pico Chemiluminescent Substrate (product # 37070) and incubating 10 minutes at room temperature. Luminescence can then be detected in a luminometer.

B. Western Blot and Quantitative Immunoanalysis

5 μL of serum is added to 95 μL of sample buffer (0.0625 M Tris, pH 6.8, 2.3% SDS, 5% 2-mercaptoethanol or 1 mM dithiothreitol, 8 M urea or 50% formamide, bromophenol blue tracking dye), the sample is then heated for 5 minutes at 100° C. 10 μL of the sample is then added to each well of a 4–20% or 4–12% gradient acrylamide gel (Novex Corp) and the gel is electrophoresed with 100–200 V constant voltage until the dye front reaches the bottom of the gel. Molecular weight standards (prestained) and BSP standards are also electrophoresed.

The protein is then transferred to nitrocellulose or other western blot membranes under standard conditions. If nitrocellulose is used transfer can be achieved in 60 minutes at 100 volts with cooling in the Novex XCell II Blot Module in Tris/Glycine buffer containing 20% methanol.

Protein is then detected by blocking the membrane with 3% BSA-NGS in PBS for 15 minutes and then adding 1% normal goat serum for 45 minutes. An antibody, for instance the polyclonal antibodye LF-100, or monoclonal LF-Mb-11 is then diluted at 1:2000 and added to the membrane for 1 hour at room temperature. The membrane is then washed 3 times with PBS-Tween 20 (0.05%). 3% BSA-1% NGS is added and then HRP-conjugated second antibody (goat anti-rabbit or goat anti-mouse IgG respectively) at is added to a final concentration of 1:50,000. The membrane is then incubated for 1 hour at room temperature and washed 3 times. Finally, Pierce SuperSIgnal West Pico Chemiluminescent reagent is added for 5 minutes and the membrane is placed in clear plastic bag and exposed to a chilled digital camera (Fuji LAS-100).

In view of the many possible embodiments to which the principles of the invention may be applied, it should be recognized that the illustrated embodiments are only particular examples of the invention and should not be taken as a limitation on the scope of the invention. Rather, the scope of the invention is defined by the following claims. We therefore claim as our invention all that comes within the scope and spirit of these claims.

We claim:

1. A method of detecting a SIBLINGS protein in a biological sample comprising:

disrupting a SIBLINGS protein/Factor H protein complex, wherein the SIBLINGS protein:

(i) binds integrin via an arginine-glycine-aspartic acid (RGD) integrin-binding domain;

(ii) binds Factor H with a 1:1 stoichiometry and with a binding constant of ≦1 nM; and (iii) confers resistance to complement mediated cell lysis, contacting the sample with an antibody, wherein the antibody specifically binds to the SIBLINGS protein; and detecting a complex formed by the SIBLINGS protein and the antibody, thereby detecting the SIBLINGS protein.

2. The method of claim 1 wherein the method further comprises separating a Factor H protein from the SIBLINGS protein.

3. The method of claim 2 wherein separating the Factor H protein from the SIBLINGS protein comprises the use of chromatography, electrophoresis, or a combination thereof.

4. The method of claim 2, further comprising quantitating the SIBLINGS protein.

5. The method of claim 1 wherein disrupting the SIBLINGS protein/Factor H protein complex comprises an addition of heat, a reducing agent, a denaturing agent, a competitive binding agent, or a combination thereof.

6. The method of claim 5 wherein the reducing agent comprises DTT (1,4-dithiothreitol), β-mercaptoethanol, trialkyl phosphines, or a combination thereof.

7. The method of claim 1 wherein the SIBLINGS protein is bone sialoprotein (BSP).

8. The method of claim 7, wherein bone sialoprotein comprises a relatively acidic bone sialoprotein and a relatively non-acidic bone sialoprotein, and wherein the method further comprises separating the relatively acidic bone sialoprotein from the relatively non-acidic bone sialoprotein prior to contacting the sample with the antibody that specifically binds to the SIBLINGS protein.

9. The method of claim 1 wherein the sample is from a subject.

10. The method of claim 9, wherein the subject is a human.

11. The method of claim 1 wherein the SIBLINGS protein is osteopontin, dentin matrix protein, or dentin sialophosphoprotein.

12. The method of claim 1 wherein the sample is used to screen for abnormal bone turnover in a subject.

13. The method of claim 12 wherein the subject is a human.

14. The method of claim 1 wherein the sample comprises a body fluid.

15. The method of claim 1 wherein the sample comprises blood, serum, or saliva.

16. The method of claim 1, wherein the sample comprises a cell from a tumor.

17. The method of claim 16, wherein the tumor is a multiple myeloma, a breast tumor, a lung tumor, a thyroid tumor, or a prostate tumor.

18. The method of claim 16 wherein the tumor produces a relatively acidic bone sialoprotein.

19. The method of claim 1, wherein the sample comprises bone.

20. The method of claim 1, wherein the antibody is a polyclonal antibody, a monoclonal antibody, or an immunologically effective portion of a monoclonal antibody.

21. The method of claim 1, wherein the SIBLINGS protein is encoded by a gene located on chromosome 4.

22. The method of claim 1, wherein the SIBLINGS protein comprises an amino acid sequence having at least 90% sequence identity to the amino acid sequence as set forth as SEQ ID NO: 1, SEQ ID NO: 12, SEQ ID NO: 14, SEQ ID NO: 16, or SEQ ID NO: 18, the SIBLINGS protein characteristics of:

(i) binding integrin;

(ii) binding Factor H with a 1:1 stoichiometry and a binding constant of $\leqq$1 nM; and (iii) confering resistance to complement mediated cell lysis.

23. The method of claim 22, wherein the SIBLINGS protein is encoded by an isolated nucleic acid molecule comprising at least 85% sequence identity to the nucleic acid sequence as set forth as SEQ ID NO: 8, SEQ ID NO: 11, SEQ ID NO: 13, SEQ ID NO: 15, or SEQ ID NO: 17, and which encodes a SIBLINGS protein that retains SIBLINGS protein characteristics of:

(i) binding integrin via an arginine-glycine-aspartic acid (RGD) integrin-binding domain;

(ii) binding Factor H with a 1:1 stoichiometry and a binding constant of $\leqq$1 nM; and (iii) confering resistance to complement mediated cell lysis.

24. A method of screening for a tumor in a subject comprising:

separating a Factor H protein from a relatively acidic bone sialoprotein, wherein the Factor H protein and the relatively acidic bone sialoprotein are in a Factor H/bone sialoprotein complex in a biological sample from the subject;

contacting the sample with an antibody that specifically binds the relatively acidic bone sialoprotein to form a complex; and detecting the complex, thereby determining a concentration of the relatively acidic bone sialoprotein in the sample, thereby screening for a tumor.

25. The method of claim 24, wherein the tumor is a breast tumor, a lung tumor, a thyroid tumor, a multiple myeloma, or a prostate tumor.

26. The method of claim 24, further comprising comparing the concentration of the relatively acidic bone sialoprotein to a control.

27. The method of claim 24 wherein the antibody comprises a polyclonal antibody or a monoclonal antibody or an immunologically effective portion thereof.

28. The method of claim 24, wherein screening for the tumor further comprises separating the relatively acidic bone sialoprotein from a relatively non-acidic bone sialoprotein prior to contacting the sample with the antibody.

29. The method of claim 28, further comprising detecting a relatively non-acidic form of bone sialoprotein in the sample and comparing the amount of relatively non-acidic bone sialoprotein in the sample to an amount of relatively acidic bone sialoprotein in the sample.

30. The method of claim 24, wherein the subject is a human.

31. A method of detecting a SIBLINGS protein in a biological sample comprising:

disrupting a SIBLINGS protein/Factor H protein complex;

contacting the sample with an antibody, wherein the antibody specifically binds to the SIBLINGS protein; and detecting a complex formed by the SIBLINGS protein and the antibody, wherein the SIBLINGS protein has the following characteristics:

(i) binds integrin via an arginine-glycine-aspartic acid (RGD) integrin-binding domain;

(ii) binds Factor H with a 1:1 stoichiometry and with a binding constant of $\leqq$1 nM; and (iii) confers resistance to complement mediated cell lysis, wherein detecting the complex, detects the SIBLINGS protein.

* * * * *

UNITED STATES PATENT AND TRADEMARK OFFICE

CERTIFICATE OF CORRECTION

PATENT NO. : 6,995,018 B1
APPLICATION NO. : 09/958617
DATED : February 7, 2006
INVENTOR(S) : Fisher et al.

It is certified that error appears in the above-identified patent and that said Letters Patent is hereby corrected as shown below:

Title Page;

On the Cover, Section (54) TITLE OF INVENTION:

Page 1, left column, "(SIBLINGS)AND" should read --(SIBLINGS) AND--.

On the Cover, Section (56) OTHER PUBLICATIONS:

Page 2, left column, "Fisher et al," should read --Fisher et al.,--.

In the Specification:

Column 1, line 2, "(SIBLINGS)AND" should read --(SIBLINGS) AND--.

Column 1, line 52, "(Fisher et el.," should read --(Fisher et al.,--.

Column 1, line 61, "258:12723-727. 1983)," should read --258:12723-727, 1983),--.

Column 2, line 17, "N-inked" should read --N-linked--.

Column 2, line 37, "10:632-440, 1995)" should read --10:632-640, 1995)--.

Column 2, line 47, "Tbsp" should read --IBSP--.

Column 3, line 2, "(Bellachcene et al." should read --(Bellahcene et al.,--.

Column 3, line 45, "or in vito," should read --or *in vitro*,--.

Column 4, line 31, "response a subject." should read --response in a subject.--.

Column 5, line 7, "Factor $H(C_s)$," should read --Factor H $(C_s)$,--.

Column 5, line 53, "(10 g/mL)," should read --(10 μg/mL),--.

Column 6, line 56, "shown SEQ ID NO:11." should read --shown in SEQ ID NO: 11.--.

Column 6, line 60, "shown SEQ ID NO:13." should read --shown in SEQ ID NO: 13.--.

Signed and Sealed this

Fourth Day of May, 2010

David J. Kappos

David J. Kappos
*Director of the United States Patent and Trademark Office*

Column 7, line 35, "expression of an deceased" should read --expression of a deceased--.

Column 8, line 4, "phophoproteins" should read --phosphoproteins--.

Column 8, line 5, "sailoprotein" should read --sialoprotein--.

Column 8, line 7, "other member" should read --other members--.

Column 8, line 11, "refers to not only to" should read --refers not only to--.

Column 8, line 16, "SIBLINGS family of protein" should read --SIBLINGS family of proteins--.

Column 10, line 21, "definition or biological specimen." should read --definition of biological specimen.--.

Column 10, line 23, "(such a blood" should read --(such as blood--.

Column 11, line 53, "parameters, (gap" should read --parameters (gap--.

Column 13, line 39, "particularly glutamic acid)" should read --(particularly glutamic acid)--.

Column 14, line 4, "(Acta. Orthop. Scand," should read --(Acta. Orthop. Scand.--.

Column 14, line 21, "western blotting" should read --Western blotting--.

Column 15, line 48, "J. Clin. Endocrinol Metab." should read --J. Clin. Endocrinol. Metab.--.

Column 15, line 60, "Cancer." should read --Cancer--.

Column 15, line 62, "Cancer." should read --Cancer--.

Column 15, line 65, "Cancer." should read --Cancer--.

Column 16, line 2, "Anticancer" should read --AntiCancer--.

Column 16, line 12, "proteins as," should read --proteins, as--.

Column 16, line 43, "8:637-641." should read --8:637-641,--.

Column 17, line 3, "separation form" should read --separation from--.

Column 17, line 45, "a normal subjects." should read --normal subjects.--.

Column 19, line 16, "Scand," should read --Scand.,--.

Column 20, line 12, "(from Quidel, LaJolla CA)" should read --(from Quidel, La Jolla, CA)--.

Column 21, line 7, "was added each well" should read --was added to each well--.

Column 21, line 33, "each wen" should read --each well--.

Column 22, Table 3, line 10, "Normals" should read --Normal--.

Column 25, line 43, "Theses results" should read --These results--.

Column 25, line 51, "Bacta" should read --Acta--.

Column 27, line 12, "(Young et al. *Genomics*" should read --(Young et al., *Genomics*--.

Column 27, line 33, "CO2" should read --$CO_2$--.

Column 27, line 58, "San Diego.)" should read --San Diego)--.

Column 28, line 17, "10%; fetal" should read --10% fetal--.

Column 28, line 18, "RPM 1640" should read --RPMI 1640--.

Column 28, line 47, "regents" should read --reagents--.

Column 29, line 4, "binding agents are, recombinant" should read --binding agents are recombinant--.

Column 29, line 16, "for the its ability" should read --for its ability--.

Column 29, line 45, "Waveland Press, Inc," should read --Waveland Press, Inc.,--.

Column 29, line 54, "in multi-step process." should read --in a multi-step process.--.

Column 31, line 23, "relatively acidic population" should read --relatively acidic populations--.

Column 33, line 53, "ch. 19." should read --ch. 19,--.

Column 34, line 9, "5,643,578 Immunization" should read --5,643,578 (Immunization--.

Column 35, line 23, "know to have" should read --known to have--.

Column 37, line 30, "Sambrook, et al." should read --Sambrook et al.--

Column 37, line 64, "DAEA-dextran-mediated" should read --DEAE-dextran-mediated--.

Column 39, line 57, "anti Mouse" should read --anti-Mouse--.

Column 40, line 19, "goat anti rabbit" should read --goat anti-rabbit--.

Column 40, line 41, "western blot" should read --Western blot--.

Column 40, line 48, "polyclonal antibodye" should read --polyclonal antibody--.

Column 40, line 53, "at is added" should read --is added--.

Column 40, line 56, "SuperSIgnal" should read --SuperSignal--.

In the Claims:

Column 79, Claim 22, line 25, "SEQ ID NO: 18, the SIBLINGS protein" should read --SEQ ID NO: 18, and which retains the SIBLINGS protein--.

Column 79, Claim 22, line 30, "confering" should read --conferring--.

Column 79, Claim 23, line 43, "confering" should read --conferring--.